*(12)* United States Patent
Mochly-Rosen et al.

(10) Patent No.: US 10,578,610 B2
(45) Date of Patent: Mar. 3, 2020

(54) PEPTIDE REGULATORS OF MITOCHONDRIAL FUSION AND METHODS OF USE

(71) Applicants: The Board of Trustees of the Leland Stanford Junior University, Stanford, CA (US); Washington University, St. Louis, MO (US)

(72) Inventors: Daria Mochly-Rosen, Menlo Park, CA (US); Gerald W. Dorn, II, Hamilton, OH (US)

(73) Assignees: Washington University, St. Louis, MO (US); Stanford University, Stanford, CA (US)

( * ) Notice: Subject to any disclaimer, the term of this patent is extended or adjusted under 35 U.S.C. 154(b) by 0 days.

(21) Appl. No.: 15/710,696

(22) Filed: Sep. 20, 2017

(65) Prior Publication Data

US 2018/0080926 A1    Mar. 22, 2018

Related U.S. Application Data

(60) Provisional application No. 62/521,910, filed on Jun. 19, 2017, provisional application No. 62/491,168, filed on Apr. 27, 2017, provisional application No. 62/488,647, filed on Apr. 21, 2017, provisional application No. 62/397,110, filed on Sep. 20, 2016.

(51) Int. Cl.
| | |
|---|---|
| *C07K 7/08* | (2006.01) |
| *C07K 14/705* | (2006.01) |
| *G01N 33/50* | (2006.01) |
| *C12N 9/14* | (2006.01) |
| *G01N 33/547* | (2006.01) |
| *G01N 33/566* | (2006.01) |
| *G01N 33/58* | (2006.01) |
| *A61K 38/00* | (2006.01) |

(52) U.S. Cl.
CPC .......... *G01N 33/5079* (2013.01); *C07K 7/08* (2013.01); *C07K 14/705* (2013.01); *C12N 9/14* (2013.01); *C12Y 306/05* (2013.01); *C12Y 310/01* (2013.01); *G01N 33/547* (2013.01); *G01N 33/566* (2013.01); *G01N 33/582* (2013.01); *A61K 38/00* (2013.01); *C07K 2319/10* (2013.01); *G01N 2500/00* (2013.01)

(58) Field of Classification Search
None
See application file for complete search history.

(56) References Cited

U.S. PATENT DOCUMENTS

| | | | |
|---|---|---|---|
| 8,466,140 | B2 | 6/2013 | Altieri et al. |
| 2015/0168379 | A1 | 6/2015 | Luo et al. |

FOREIGN PATENT DOCUMENTS

| | | |
|---|---|---|
| WO | WO 1998/055618 A1 | 12/1998 |
| WO | WO 2001/025274 A1 | 4/2001 |

OTHER PUBLICATIONS

Eschenbacher et al., "Two Rare Human Mitofusin 2 Mutations Alter Mitochondrial Dynamics and Induce Retinal and Cardiac Pathology in *Drosophila*", PLOS ONE, vol. 7, Issue 9, No. e44296, pp. 1-10 (2012).
Franco et al., "Correcting Mitochondrial Fusion by Manipulating Mitofusin Conformations", Nature, vol. 540, No. 7631, pp. 74-79 (2016).
Huang, "Molecular Interaction of Mitofusin 2 and its Role in Mitochondrial Fusion", Thesis, University of Rochester, Rochester, New York, pp. 1-140 (2008).
International Search Report and Written Opinion from International Application No. PCT/US2017/052556, 18 pages, dated Dec. 12, 2017.

*Primary Examiner* — John D Ulm

(57) ABSTRACT

Mitofusin modulatory peptides are described which may function as activators or inhibitors of mitochondrial fusion. The sequences and compositions comprising the sequences are useful for treating diseases or disorders associated with mitofusin 1 (Mfn1) and/or mitofusin 2 (Mfn2) and mitochondrial dysfunction. Methods of treatment, pharmaceutical formulations and methods of identifying compounds that mimic the activity of the peptides for use in screening assays are also described.

12 Claims, 27 Drawing Sheets

Specification includes a Sequence Listing.

```
SEQ ID No:1
(hMfn1) 1    MAE-PVSPLKHFVLAKKAITAIFDQLLEFVTEGSHFVEATYKNPELDRIATEDDLVEMQG    59
             MAE   SPLKHFV AKK I  IF+QL  ++ E + F+E TY+N ELD + TE+ +++++G
SEQ ID No:2
(hMfn2) 21   MAEVNASPLKHFVTAKKKINGIFEQLGAYIQESATFLEDTYRNAELDPVTTEEQVLDVKG   80 hMfn1   60   YKDKLSIIGEVLSRRHMKVAFFGRTSSGKSSVINAMLWDKVLPSGIGHITNCFLSVEGTD  119
             Y K+  I EVL+RRHMKVAFFGRTS+GKS+VINAMLWDKVLPSGIGH TNCFL VEGTD
hMfn2   81   YLSKVRGISEVLARRHMKVAFFGRTSNGKSTVINAMLWDKVLPSGIGHTTNCFLRVEGTD  140 hMfn1   120  GDKAYLMTEGSDEKKSVKTVNQLAHALHMDKDLKAGCLVRVFWPKAKCALLRDDLVLVDS  179
             G +A+L+TEGS+EK+S KTVNQLAHALH DK L AG LV V WP +KC LL+DDLVL+DS
hMfn2   141  GHEAFLLTEGSEEKRSAKTVNQLAHALHQDKQLHAGSLVSVMWPNSKCPLLKDDLVLMDS  200 hMfn1   180  PGTDVTTELDSWIDKFCLDADVFVLVANSESTLMNTEKHFFHKVNERLSKPNIFILNNRW  239
             PG DVTTELDSWIDKFCLDADVFVLVANSESTLM TEKHFFHKV+ERLS+PNIFILNNRW
hMfn2   201  PGIDVTTELDSWIDKFCLDADVFVLVANSESTLMQTEKHFFHKVSERLSRPNIFILNNRW  260 hMfn1   240  DASASEPEYMEDVRRQHMERCLHFLVEELKVVNALEAQNRIFFVSAKEVLSARKQKAQGM  299
             DASASEPEYME+VRRQHMERC  FLV+EL VV+   +A +RIFFVSAKEVL+AR QKAQGM
hMfn2   261  DASASEPEYMEEVRRQHMERCTSFLVDELGVVDRSQAGDRIFFVSAKEVLNARIQKAQGM  320 hMfn1   300  PESGVALAEGFHARLQEFQNFEQIFEECISQSAVKTKFEQHTIRAKQILATVKNIMDSVN  359
             PE G ALAEGF R+ EFQNFE+ FEECISQSAVKTKFEQHT+RAKQI   V+ IMDS++
hMfn2   321  PEGGGALAEGFQVRMFEFQNFERRFEECISQSAVKTKFEQHTVRAKQIAEAVRLIMDSLH  380 hMfn1   360  LAAEDKRHYSVEEREDQIDRLDFIRNQMNLLTLDVKKKIKEVTEEVANKVSCAMTDEICR  419
             +AA +++ Y E RE++ DRL FI Q+ LL D K +IK++TEEV +VS AM +EI R
hMfn2   381  MAAREQQVYCEEMREERQDRLKFIDKQLELLAQDYKLRIKQITEEVERQVSTAMAEEIRR  440
```

FIG. 1C

```
hMfn1  420  LSVLVDEFCSEPHPNPDVLKIYKSELNKHIEDGMGRNLADRCTDEVNALVLQTQQEIIEN  479
            LSVLVD++    +PHP+P VLK+YK+EL++HIE+G+GRN++DRC+    +    +  QQ++I+
hMfn2  441  LSVLVDDYQMDPHPSPVVLKVYKNELHRHIEEGLGRNMSDRCSTAITNSLQTMQQDMIDG  500 hMfn1  480  LKPLLPAGIQDKLHTLIPCKKFDLSYNLNYHKLCSDPQEDIVRFSLGWSSLVHRFLGPR   539
            LKPLLP ++ ++   L+P + F L+Y+LN  KLC+DPQEDI F PSLGW+ LV+RPLGP+
hMfn2  501  LKPLLFVSVRSQIDMLVPRQCFSLNYDLNCIDKLCADPQEDIEFHPSLGWTMLVNPPLGPK 560 hMfn1  540  NAQRVLLGLSEPIFQLPRSLASTPTAPTTPATPDNA-SQEELMITLVTGLASVTSRTSMG  598
            N++R L+G ++   Q+ R + TP  P+ P  P   + +QEE M+++VTGLAS+TSRTSMG
hMfn2  561  NSRPALMGYND-----QVQRPIPLTPANPSMPPLPQGSLTQEEFMVSMVTGLASLTSRTSMG 617 hMfn1  599  IIIVGGVIWKTIGWKLLSVSLTMYGALYLVERLSWTTHAKERAFKQQFVNYATEKLRMIV  658
            I++VGGV+WK +GW+L+++S  +YG LY++ERL+WTT AKERAFK+QFV +A+EKL++++
hMfn2  618  ILVVGGVVWKAVGWRLIALSFGLYGLLYVERLTWTTKAKERAFKRQFVEHASEKLQLVI   677 hMfn1  659  SSTSANCSHQVKQQIATTFARLCQQVDITQKQLEEEIARLPKEIDQLEKIQNNSKLLRNK  718
            S T +NCSHQV+Q+++ TFA LCQQVD+T++ LE+EIA  + K+I+ L+ +Q+ +KLLRNK
hMfn2  676  SYTGSNCSHQVQQELSGTPAHLCQQVDVTRENLEQEIAMNKKIEVLDSLQSKAKLLRNK   737 hMfn1  719  AVQLENELENFTKQFLPSSNEES   741
            A  L++EL FT Q+L  S
hMfn2  738  AGWLDSELNMFTHQYLQPSR      756
```

FIG. 1C (cont.)

```
hMfn1  420  LSVLVDEFCSEFHPNPDVLKIYKSELNKHIEDGMGRNLADRCTDEVNALVLQTQQEIIEN  479
            LSVLVD++   +FHP+P VLK+YK+EL++HIE+G+GRN++DRC+   +     +  QQ++I+
hMfn2  441  LSVLVDDYQMDFHPSPVVLKVYKNELHRHIEEGLGRNMSDRCSTAITNSLQTMQQDMIDG  500 hMfn1  480  LKPLLPAGIQDKLHTLIPCKKFDLSYNLNYHKLCSDFQEDIVFRFSLGWSSLVHRFLGPR  539
            LKPLLP  ++  ++   L+P + F L+Y+LN   KLC+DFQEDI F FSLGW+ LV+RFLGP+
hMfn2  501  LKPLLPVSVRSQIDMLVPRQCFSLNYDLNCDKLCADFQEDIEFHFSLGWTMLVNRFLGPK  560 hMfn1  540  NAQRVLLGLSEPIFQLPRSLASTPTAPTTPATPDNA-SQEELMITLVTGLASVTSRTSMG  598
            N++R L+G ++    Q+ R + TP  P+ P   P   +  +QEE M+++VTGLAS+TSRTSMG
hMfn2  561  NSRRALMGYND---QVQRPIPLTPANPSMPPLPQGSLTQEEFMVSMVTGLASLTSRTSMG  617 hMfn1  599  IIIVGGVIWKTIGWKLLSVSLTMYGALYLYERLSWTTHAKERAFKQQFVNYATEKLRMIV  658
            I++VGGV+WK +GW+L+++S   +YG LY+YERL+WTT AKERAFK+QFV +A+EKL++++
hMfn2  618  ILVVGGVVWKAVGWRLIALSFGLYGLLYVYERLTWTTKAKERAFKRQFVEHASEKLQLVI  677 hMfn1  659  SSTSANCSHQVKQQIATTFARLCQQVDITQKQLEEEIARLPKEIDQLEKIQNNSKLLRNK  718
            S T +NCSHQV+Q+++  TFA LCQQVD+T++ LE+EIA  + K+I+ L+  +Q+  +KLLRNK
hMfn2  678  SYTGSNCSHQVQQELSGTFAHLCQQVDVTRENLEQEIAAMNKKIEVLDSLQSKAKLLRNK  737 hMfn1  719  AVQLENELENFTKQFLPSSNEES  741
            A   L++EL  FT Q+L  S
hMfn2  738  AGWLDSELNMFTHQYLQPSR    756
```

FIG. 1D hMfn2-HR2*   NH2-GSNCSHQNQELSGTEAH...QPS-COOH
hMfn2-HR2*   COOH-SFI...NH3

FIG. 2A hMfn2-HR1**  NH3-PQNEERREEC...LITQ-COOH
hMfn2-HR2*   COOH-SYQI...NH3

FIG. 2B

*hMfn2-HR2 = SEQ ID NO:2 fragment, residue 681-756

**hMfn2-HR1 = SEQ ID NO:2 fragment, residue 338-421

PEPTIDE REGULATORS OF MITOCHONDRIAL FUSION AND METHODS OF USE

CROSS-REFERENCE TO RELATED APPLICATIONS

This application claims the benefit of U.S. Provisional Application No. 62/397,110, filed Sep. 20, 2016; U.S. Provisional Application No. 62/488,647, filed Apr. 21, 2017; U.S. Provisional Application No. 62/491,168, filed Apr. 27, 2017; and U.S. Provisional Application No. 62/521,910, filed Jun. 19, 2017, each of which is incorporated by reference herein in its entirety.

STATEMENT REGARDING GOVERNMENT INTEREST

This invention was made with Government support under contracts HL052141, HL059888, and HL107276 awarded by the National Institutes of Health. The Government has certain rights in the invention.

TECHNICAL FIELD

Compositions and methods for regulating mitochondrial function including mitochondrial fusion are described. The compositions and methods are also useful for modulating cellular functions which are affected by mitochondrial dysfunction. Peptides and variants thereof have been designed based on modeling of the structure of mitofusin proteins and designing modifiers of the structures. Peptides shown to activate or inhibit mitochondrial fusion are described. Cells may be treated either by the peptides, including peptide conjugates or fusions, peptoids (compounds that mimic peptides) or by polynucleotide compositions which encode the peptide compositions. Methods for screening for and identifying modulators of mitochondrial fusion are also provided.

REFERENCE TO SEQUENCE LISTING, TABLE OR COMPUTER PROGRAM

A Sequence Listing is being submitted electronically via EFS in the form of a text file, created Sep. 20, 2017, and named "091511-0616_8282seqlist_ST25.txt" (45,401 bytes), the contents of which are incorporated herein by reference in their entirety.

BACKGROUND

Mitochondria are dynamic organelles, remodeling and exchanging contents during cyclic fusion and fission. Mitochondria fuse to transfer genetic information and promote mutual repair through content exchange. Mitochondrial outer membrane tethering and fusion is mediated by mitofusins (Mfn) 1 and 2 (Santel, 2006, Biochim Biophys Acta, 2006, 1763:490-499) is essential for embryonic development (Chen et al., 2003, J Cell Biol, 160:189-200; Kasahara et al., 2013, Science, 342:734-737) and tissue homeostasis (Chen et al., 2007, Cell, 130:548-562; Chen et al., 2010, Cell, 141:280-289; Song et al., 2015, Cell Metab, 21:273-285). In mammalian cells mitochondrial fission increases in response to injury and during programmed cells death. Mitochondrial fusion opposes fission and is essential for cell health (Chan, 2012, Annu Rev Genet, 46:265-287). Multiple mutations that provoke Mfn2 dysfunction can cause the untreatable neurodegenerative condition, Charcot Marie Tooth disease type 2A (CMT2A) (Bombelli et al., 2014, JAMA Neurol, 71:1036-1042). Absence of non-genetic means for regulating mitofusins has limited development of therapeutically effective approaches to treat or prevent CMT2A and other diseases causally linked to disturbances in mitochondrial fusion.

It has not been possible to directly modulate mitochondrial fusion, in part because the structural basis of mitofusin function is incompletely understood. Modeling, and rational design and data presented herein provide evidence that Mfns adopt either a fusion-constrained or a fusion-permissive molecular conformation directed by specific intramolecular binding interactions. Supportive studies demonstrate that Mfn1- and Mfn2-dependent mitochondrial fusion can be positively and negatively regulated by targeting these conformational transitions. Based on this model, a cell-permeant peptide was engineered that destabilizes the fusion-constrained Mfn state and promotes the fusion-permissive Mfn conformation. Application of this peptide construct to cultured cells harboring CMT2A gene defects reverses mitochondrial fragmentation and depolarization. The relationship between Mfn1 and Mfn2 conformational plasticity and mitochondrial dynamism uncovers a central molecular mechanism regulating mitochondrial fusion that can be manipulated to correct mitochondrial pathology in conditions such as CMT2A wherein defective mitochondrial dynamics is a contributory factor. Accordingly, the present disclosure provides compositions and methods for treating disorders related to defective mitochondrial fusion.

BRIEF SUMMARY

As described below, the present disclosure provides compositions and methods for the control of mitochondrial fusion and for the treatment or prevention of diseases or disorders associated with a mitochondrial defect.

In one aspect a peptide which can modulate or regulate mitochondrial fusion is provided. In another aspect, a composition comprising the modulatory peptide is provided.

In some embodiments, the modulatory peptide increases mitochondrial fusion activity in a cell which has been exposed to the modulatory peptide. In other embodiments, the modulatory peptide inhibits or decreases mitochondrial fusion activity in a cell which has been exposed to the modulatory peptide. In still other embodiments, mitochondrial fusion activity is measured as an aspect ratio wherein an increase in the aspect ratio indicates in increase in mitochondrial fusion activity and a decrease in the aspect ratio indicates a decrease in mitochondrial fusion activity.

In some embodiments, the peptide comprises the amino acid sequence $X_1X_2AX_1X_2VX_1GX_1MX_2X_1LX_2X_1X_2AX_1$ (SEQ ID NO:4), $X_1X_2AX_1X_2VX_1GIMX_2X_1LX_2X_1X_2AX_1$ (SEQ ID NO:5), $X_1X_2AX_1X_2VX_1GMX_2X_1LX_2X_1X_2AX_1$ (SEQ ID NO:6), $GIMX_2X_1LX_2X_1X_2AX_1$ (SEQ ID NO:51), or $GMX_2X_1LX_2X_1X_2AX_1$ (SEQ ID NO:52), wherein $X_1$ and $X_2$ represent any amino acid. In other embodiments, $X_1$ is a charged amino acid. In still other embodiments, $X_2$ is a neutral amino acid. In yet other embodiments, $X_1$ is a charged amino acid and $X_2$ is a neutral amino acid.

In some embodiments, $X_1$ is selected from the group consisting of R, K, D, N, Q, E and H.

In some embodiments, $X_2$ is selected from the group consisting of I, L, V, A, M, C, S, T and G.

In some embodiments, the modulatory peptide has a length of 15 to 26, 16 to 22, 16 to 20, 17 to 19, or 17 to 19 amino acids. In other embodiments, the modulatory peptide has a length of about 15, 16, 17, 18, 19, 20, 21, 22, 23, 24 or 25 amino acids.

In some embodiments, the modulatory peptide comprises the sequence QIAEAVRGIMDSLHMAAR (SEQ ID NO:14), where G is not part of the native sequence, or a variant thereof, wherein the variant has 1, 2, 3 or 4 amino acid substitutions compared to SEQ ID NO:14. In other embodiments, the amino acid substitution is selected from the group consisting of Q substituted with N, E substituted with D, R substituted with K, D substituted with E and H substituted with K or R. In still other embodiments, the amino acid substitution is selected from the group consisting of I substituted with V or L, A substituted with G, V substituted with L, M substituted with I, S substituted with T, and L substituted with V. In yet other embodiments, the modulatory peptide comprising SEQ ID NO:14 or a variant thereof as described above is a fusion activating peptide.

In some embodiments, the modulatory peptide comprises the sequence QIAEAVRGMDSLHMAAR (SEQ ID NO:16), wherein the isoleucine following the glycine in SEQ ID NO:12 is deleted to generate SEQ ID NO:16.

In some embodiments, the modulatory peptide is a fragment of SEQ ID NO:14 or variant thereof, wherein the fragment is 9 to 17, 10 to 17, 11 to 17, 12 to 17, 13 to 17, 14 to 17, 15 to 17, 16 to 17, 9 to 15, 9 to 14, 9 to 13, 9 to 12, 10 to 12, or 11 to 12 amino acids or 9, 10, 11, 12, 13, 14, 15, 16 or 17 amino acids in length. In other embodiments, the modulatory peptide is a fragment of SEQ ID NO:14 wherein the fragment comprises GIMDSLHMAAR (SEQ ID NO:48), wherein the fragment activates mitochondrial fusion when administered to a cell or mammal. In still other embodiments, the modulatory peptide comprises a variant of SEQ ID NO:48, wherein one, two or three amino acids are substituted such that the modulatory peptide activates mitochondrial fusion in a cell. In yet other embodiments, the modulatory peptide is a linear peptide comprising SEQ ID NO:48 or variant thereof and a carrier peptide. In other embodiments, the linear peptide further comprises a linker between SEQ ID NO:48 or variant thereof and the carrier peptide.

In some embodiments, the modulatory peptide is a fragment of SEQ ID NO:18 or variant thereof, wherein the fragment is 9 to 17, 10 to 17, 11 to 17, 12 to 17, 13 to 17, 14 to 17, 15 to 17, 16 to 17, 9 to 15, 9 to 14, 9 to 13, 9 to 12, 10 to 12, or 11 to 12 amino acids or 9, 10, 11, 12, 13, 14, 15, 16 or 17 amino acids in length. In other embodiments, the modulatory peptide is a fragment of SEQ ID NO: 18 wherein the fragment comprises GELLAQDYKLR (SEQ ID NO: 43), wherein the fragment inhibits mitochondrial fusion when administered to a cell or mammal. In still other embodiments, the modulatory peptide comprises a variant of SEQ ID NO: 43, wherein one, two or three amino acids are substituted such that the modulatory peptide inhibits mitochondrial fusion in a cell. In yet other embodiments, the modulatory peptide is a linear peptide comprising SEQ ID NO:43 or variant thereof and a carrier peptide. In other embodiments, the linear peptide further comprises a linker between SEQ ID NO:43 or variant thereof and the carrier peptide.

In some embodiments, the modulatory peptide is an activator of mitochondrial fusion and comprises the amino acid sequence GIMXXXXMAAR (SEQ ID NO:73).

In some embodiments, the modulatory peptide is an inhibitor of mitochondrial fusion and comprises the amino acid sequence GELLAQXYKXR (SEQ ID NO:74).

In some embodiments, the modulatory peptide is linked to a carrier moiety. In other embodiments, the carrier moiety is a composition which facilitates transport of the modulatory peptide across a cellular membrane.

In some embodiments, the carrier moiety is a carrier peptide. In other embodiments, the carrier peptide is a Tat peptide comprising SEQ ID NO:25 or a variant thereof. In still other embodiments, the Tat peptide is linked via a peptide bond to a cysteine at its N-terminal or its C-terminal end.

In some embodiments, the modulatory peptide is linked to a carrier peptide via a peptide bond. In other embodiments, the modulatory peptide is a linear peptide which comprises the carrier peptide and the modulatory peptide.

In some embodiments, the modulatory peptide is linked to a linker, wherein the linker is positioned between the modulatory peptide and the carrier peptide. In other embodiments, the linker is a peptide linker which is linked at one end to the modulatory peptide by a peptide bond and is linked at the other end to the carrier peptide by a peptide bond. In still other embodiments, the linker peptide comprises 1, 2, 3, 4, 5, or more amino acids. In yet other embodiments, the linker comprises 1 to 2, 1 to 5, 2 to 5, 2 to 4, 1 to 10, 5 to 10, 3 to 6, or 2 to 10 amino acids. In still other embodiments, the linker is G, GG, GGG, or GGGG (SEQ ID NO:34).

In some embodiments, the modulatory peptide is C-terminal to the carrier peptide. In other embodiments, the modulatory peptide is N-terminal to the carrier peptide.

In some embodiments, the modulatory peptide linked to the carrier peptide directly or via a peptide linker is a linear construct which is modified at the amino terminus, the carboxyl terminus or both the amino and carboxyl termini of the linear construct. In other embodiments, the amino terminal modification is an amine group or an acetyl group. In other embodiments, the carboxyl terminal modification is an amide group.

In some embodiments, the carrier moiety is a carrier peptide and the carrier peptide is linked to the modulator peptide via a disulfide bond, wherein the modulator peptide is linked by a peptide bond to a cysteine residue at its N-terminus or at its C-terminus, wherein the carrier peptide is linked by a peptide bond to a cysteine residue at is N-terminus or at its C-terminus, and wherein the cysteine residue of the modulator peptide is linked to the cysteine residue of the carrier peptide by the disulfide bond.

In some embodiments, the modulator comprises SEQ ID NO:45. In other embodiments, the modulator comprises a variant of SEQ ID NO:45 wherein the variant comprises 1, 2, 3, 4, 5, 6, 1 to 6, 1 to 5, 1 to 4, 1 to 3 or 1 to 2 amino acid substitutions wherein the modulator inhibits mitochondrial fusion in a cell.

In some embodiments, the modulator comprises SEQ ID NO:50. In other embodiments, the modulator comprises a variant of SEQ ID NO:50 wherein the variant comprises 1, 2, 3, 4, 5, 6, 1 to 6, 1 to 5, 1 to 4, 1 to 3 or 1 to 2 amino acid substitutions wherein the modulator activates mitochondrial fusion in a cell.

In some embodiments, the amino terminus, the carboxyl terminus or both the amino and carboxyl termini of the modulatory peptide are modified. In other embodiments, the amino terminal modification is an amine group or an acetyl group. In other embodiments, the carboxyl terminal modification is an amide group.

In some embodiments, the amino terminus, the carboxyl terminus or both the amino and carboxyl termini of the carrier peptide are modified. In other embodiments, the amino terminal modification is an amine group or an acetyl group. In other embodiments, the carboxyl terminal modification is an amide group.

In another aspect, a polynucleotide encoding a modulatory peptide is provided.

In some embodiments, the polynucleotide encodes a peptide comprising the amino acid sequence $X_1X_2AX_1X_2VX_1GX_1MX_2X_1LX_2X_1X_2AX_1$ (SEQ ID NO:4). In other embodiments, $X_1$ is a charged amino acid. In still other embodiments, $X_2$ is a neutral amino acid. In yet other embodiments, $X_1$ is a charged amino acid and $X_2$ is a neutral amino acid. In some embodiments, $X_1$ is selected from the group consisting of R, K, D, N, Q, E and H. In some embodiments, $X_2$ is selected from the group consisting of I, L, V, A, M, C, S, T and G.

In some embodiments, the polynucleotide encodes a linear construct comprising a modulatory peptide and a carrier peptide. In other embodiments, the linear construct further comprises a linker peptide positioned between the modulatory peptide and the carrier peptide. In still other embodiments, the linker peptide comprises 1, 2, 3, 4, 5, or more amino acids. In yet other embodiments, the linker comprises 1 to 2, 1 to 5, 2 to 5, 2 to 4, 1 to 10, 5 to 10, 3 to 6, or 2 to 10 amino acids. In still other embodiments, the linker is G, GG, GGG, or GGGG (SEQ ID NO:34).

In some embodiments, the polynucleotide encodes a peptide comprising any one of SEQ ID NOS. 4 to 52.

In some embodiments, the carrier peptide is a Tat peptide comprising SEQ ID NO:25 or a variant thereof.

In another aspect, a polynucleotide vector is provided comprising the polynucleotide that encodes the modulatory peptide.

In another aspect a method for activating mitochondrial fusion is provided.

In some embodiments, the method comprises exposing a cell to a modulatory peptide according to any one of the foregoing embodiments.

In some embodiments, the method comprises transfecting a cell with a polynucleotide vector comprising the polynucleotide that encodes a modulatory peptide according to any one of the foregoing embodiments.

In another aspect, a method for treating a disease or disorder associated with mitochondrial dysfunction is provided, wherein the method comprises administering to a subject in need thereof a modulatory peptide according to any one of the above embodiments.

In some embodiments, the mitochondrial dysfunction is a dysfunction of mitochondrial fusion and/or fission. In other embodiments, the mitochondrial dysfunction is a dysfunction of mitochondrial fusion.

In some embodiments, the disease or disorder associated with mitochondrial dysfunction is a neurodegenerative disease, ischemia, reperfusion injury, diabetes-induced neuropathy, or heart disease. In other embodiments, the ischemia and/or reperfusion injury is to brain tissue. In still other embodiments, the ischemia and/or reperfusion injury is to cardiac tissue.

In some embodiments, the method for treating a disease or disorder is a method for treating stroke.

In some embodiments, the neurodegenerative disease is selected from the group consisting of Parkinson's disease, Huntington's disease, or Alzheimer's disease.

In another aspect, methods for screening a plurality of candidate molecules for modulators of mitochondrial dysfunction are provided.

In some embodiments, the modulators are activators of mitochondrial fusion. In other embodiments, the modulators increase the mitochondrial aspect ratio in a cell. In still other embodiments, the modulators decrease mitochondrial clumping in a cell.

In some embodiments, the method for screening comprises attaching an Mfn2 protein or HR2-containing fragment thereof to a solid substrate, labeling a modulatory peptide according to any one of the foregoing embodiments with a detectable label, mixing and incubating the Mfn2 protein or fragment thereof with a candidate molecule, and detecting the label at the location of the Mfn2 protein or fragment thereof attached to the solid substrate, wherein a decrease or loss in detection of the label is indicative of an activator of mitochondrial fusion. In some embodiments, the activator of mitochondrial fusion is a candidate molecule that can increase the mitochondrial aspect ratio in a cell.

In some embodiments, the method for screening comprises labeling a first Mfn2 protein or fragment thereof which comprises the HR2 domain with an acceptor fluorophore within or near the HR2 domain to generate a first labeled Mfn2 protein, labeling a second Mfn2 protein or fragment thereof which comprises the HR2 domain with a donor fluorophore to generate a second labeled Mfn2 protein, mixing together the first and second labeled Mfn2 proteins to generate a control mixture, mixing the first and second labeled Mfn2 protein with at least one of the plurality of candidate molecules to generate a test mixture, and measuring the fluorescence of the test mixture and the fluorescence of the control mixture. In other embodiments, the method further comprises comparing the fluorescence of the test mixture with the fluorescence of the control mixture, wherein when the fluorescence of the test mixture is less than the fluorescence of the control mixture, the at least one of the plurality of candidate molecules in the test mixtures is identified as an activator of mitochondrial fusion.

In some embodiments, the method comprises labeling an Mfn2 protein with an acceptor fluorophore within or near the HR1 domain and labeling the Mfn2 protein with a donor fluorophore within or near the HR2 domain to generate a labeled Mfn2 protein, mixing the labeled Mfn2 protein with at least one of the plurality of candidate molecules to generate a test mixture, and measuring the fluorescence of the test mixture and the fluorescence of the control mixture. In other embodiments, the method further comprises comparing the fluorescence of the test mixture with the fluorescence of the control mixture, wherein when the fluorescence of the test mixture is less than the fluorescence of the control mixture, the at least one of the plurality of candidate molecules in the test mixtures is identified as an activator of mitochondrial fusion.

BRIEF DESCRIPTION OF DRAWINGS

FIGS. 1A-1D illustrate the domain organization of mitofusin 1 and 2 proteins (FIG. 1A), domain interactions (FIG. 1B), and domain sequence homologies (FIGS. 1C-1D). FIGS. 1C-1D include boxing of sequence regions for the GTPase, HR1, transmembrane (TM), and HR2 domains.

FIG. 2A-2B illustrates antiparallel interaction of the Mfn2 HR1 and HR2 domains. The bottom sequence for the HR2 domain is written left to right in a C-terminal to N-terminal direction, indicative of the antiparallel interaction of the HR1 and HR2 domains.

FIG. 4A shows representative confocal microscopy images which were analyzed to generate quantitative data provided in FIG. 4B.

FIG. 12A: confocal images in which various MEF cells are treated with mitochondrial fusion regulatory peptides. FIG. 12B: corresponding quantitative data for aspect ratio.

FIG. 13A: a schematic of the transgene construct. FIG. 13B: results of a time course study of mitochondrial fragmentation after adeno-Cre mediated induction of Mfn2 T105m. FIGS. 13C and 13D: Immunoblot analysis of mitochondrial dynamic factors in Mfn2 T105M cells.

FIG. 16A: study design with confirmation of Mfn2 T105M fl/st transgene genotype. FIG. 16B: quantitative analysis of Mfn2 expression. FIG. 16C: merged live confocal images of cultured neurons in the presence and absence of a mitochondrial fusion regulatory peptide. FIG. 16D: confocal images of Mfn2 T105M expressing neurons with and without treatment with a mitochondrial fusion regulatory peptide. FIG. 16E: quantitative data for FIG. 16D.

FIG. 18A shows effects on direct infarct area. FIG. 18B shows effects on direct infarct volume.

FIG. 19A shows effects on indirect infarct area. FIG. 19B shows effects on indirect infarct volume.

BRIEF DESCRIPTION OF THE SEQUENCES

TABLE 1

Figure 1A:
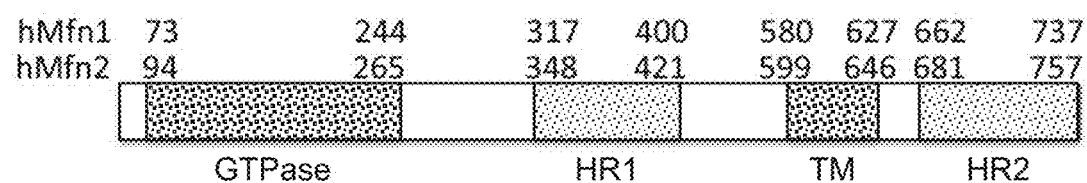

| SEQ ID NO: | Description | Sequence |
|---|---|---|
| 1 | hMfn1 (NP_284941) | MAEPVSPLKHFVLAKKAITAIFDQLLEFVTEGSHFVEATY KNPELDRIATEDDLVEMQGYKDKLSIIGEVLSRRHMKVAF FGRTSSGKSSVINAMLWDKVLPSGIGHITNCFLSVEGTDG DKAYLMTEGSDEKKSVKTVNQLAHALHMDKDLKAGCLVRV FWPKAKCALLRDDLVLVDSPGTDVTTELDSWIDKFCLDAD VFVLVANSESTLMNTEKHFFHKVNERLSKPNIFILNNRWD ASASEPEYMEDVRRQHMERCLHFLVEELKVVNALEAQNRI FFVSAKEVLSARKQKAQGMPESGVALAEGFHARLQEFQNF EQIFEECISQSAVKTKFEQHTIRAKQILATVKNIMDSVNL AEDKRHYSVEEREDQIDRLDFIRNQMNLLTLDVKKKIKE VTEEVANKVSCAMTDEICRLSVLVDEFCSEFHPNPDVLKI YKSELNKHIEDGMGRNLADRCTDEVNALVLQTQQEIIENL KPLLPAGIQDKLHTLIPCKKFDLSYNLNYHKLCSDFQEDI VFRFSLGWSSLVHRFLGPRNAQRVLLGLSEPIFQLPRSLA STPTAPTTPATPDNASQEELMITLVTGLASVTSRTSMGII |

TABLE 1-continued

| SEQ ID NO: | Description | Sequence |
|---|---|---|
| | | IVGGVIWKTIGWKLLSVSLTMYGALYLYERLSWTTHAKER AFKQQFVNYATEKLRMIVSSTSANCSHQVKQQIATTFARL CQQVDITQKQLEEEIARLPKEIDQLEKIQNNSKLLRNKAV QLENELENFTKQFLPSSNEES |
| 2 | hMfn2 | MSLLFSRCNSIVTVKKNKRHMAEVNASPLKHFVTAKKKIN GIFEQLGAYIQESATFLEDTYRNAELDPVTTEEQVLDVKG YLSKVRGISEVLARRHMKVAFFGRTSNGKSTVINAMLWDK VLPSGIGHTTNCFLRVEGTDGHEAFLLIEGSEEKRSAKTV NQLAHALHQDKQLHAGSLVSVMWPNSKCPLLKDDLVLMDS PGIDVTFELDSWIDKFCLDADVFVLVANSESTLMQIEKHF FHKVSERLSRPNIFILNNRWDASASEPEYMEEVRRQHMER CTSFLVDELGVVDRSQAGDRIFFVSAKEVLNARIQKAQGM PEGGGALAEGFQVRMFEFQNFERRFEECISQSAVKTKFEQ HTVRAKQIAEAVRLIMDSLHMAAREQQVYCEEMREERQDR LKFIDKQLELLAQDYKLRIKQITEEVERQVSTAMAEEIRR LSVLVDDYQMDFHPSPVVLKVYKNELHRHIEEGLGRNMSD RCSTAITNSLQTMQQDMIDGLKPLLPVSVRSQIDMLVPRQ CFSLNYDLNCDKLCADFQEDIEFHFSLGWTMLVNRFLGPK NSRRALMGYNDQVQRPIPLTPANPSMPPLPQGSLTQEEFM VSMVTGLASLTSRTSMGILVVGGVVWKAVGWRLIALSFGL YGLLYVYERLTWTTTKAKERAFKRQFVEHASEKLQLVISYT GSNCSHQVQQELSGTFAHLCQQVDTRENLEQEIAAMNKK IEVLDSLQSKAKLLRNKAGWLDSELNMFTHQYLQPSR |
| 3 | hDLP (PDB 2J60) | MVNQVATDRFIQDLERVAQVRSEMSVCLNKLAETINKAEL AGDSSSGKLSLERDIEDITIASKNLQQGVFRLLVLGDMKR GKSTFLNALIGENLLPSDVNPCTAVLTVLRYGPEKKVTIH FNDGKSPQQLDFQNFKYKYTIDPAEAKKLEQEKKQAFPDV DYAVVEYPLTLLQKGIEIVDSPGLNDIEARNELSLGYVNN CHAILFVMRASQPCTLGERRYLENYIKGRGLTVFFLVNAW DQVRESLIDPDDVEELQASENRLRQVFNANLAEYCTVEGQ NIYDERVFELSSIQALRRRLKNPQADLDGTGFPKFMDSLN TFLTRERAIAELRQVRTLARLACNHTREAVARRIPLLEQD VNELKKRIDSVEPEFNKLTGIRDEFQKEIINTRDTQARTI SESFRSYVLNLGNTFENDFLRYQPELNLFDFLSSGKREAF NAALQKAFEQYITDKSAAWTLTAEKDINAAFKELSRSASQ YGASYNQITDQITEKLTGKDVKVHTTTTAEEDNSPGWAKW AMGLLSLSKGNLAGFALAGAGFDWKNILLNYFTVIGIGGI ITAVTGILLGPIGFALLGLGVGFLQADQARRELVKTAKKE LVKHLPQVAHEQSQVVYNAVKECFDSYEREVSKRINDDIV SRKSELDNLVKQKQTREINRESEFNRLKNLQEDVIAQLQK IEAAYSNLLAYYSHH |
| 4 | Consensus | XXAXXVXGXMXXLXXXAX |
| 5 | Consensus variant | $X_1X_2AX_1X_2VX_1GIMX_2X_1LX_2X_1X_2AX_1$ |
| 6 | Consensus variant | $X_1X_2AX_1X_2VX_1GMX_2X_1LX_2X_1X_2AX_1$ |
| 7 | HR1 fragment (Mfn1 317-400) | FQNFEQIFEECISQSAVKTKFEQHTIRAKQILATVKNIMD SVNLAAEDKRHYSVEEREDQIDRLDFIRNQ |
| 8 | HR1 fragment (Mfn2 348-421) | FQNFERRFEECISQSAVKTKFEQHTVRAKQIAEAVRLIMD SLHMAAREQQVYCEEMREERQDRLKFIDKQLELLAQDYKL RIKQ |
| 9 | Mfn1 HR1 N-term helix | FQNFEQIFEECISQSAVKTKFEQHTIRAKQILATVKNIMD SVNLAAE |
| 10 | Mfn1 HR1 C-term helix | HYSVEEREDQIDRLDFIRNQMNLLTLDVKKK |
| 11 | Mfn2 HR1 N-term helix | FQNFERRFEECISQSAVKTKFEQHTVRAKQIAEAVRLIMD SLHMAAR |
| 12 | Mfn2 HR1 C-term helix | VYCEEMREERQDRLKFIDKQQLELLAQDYKLR |
| 13 | Mfn2-367-384 | QIAEAVRLIMDSLHMAAR |
| 14 | Mfn2-367-384 L→G (HR1-367-384Gly) "GoFuse1" | QIAEAVRGIMDSLHMAAR |
| 15 | Mfn2-367-384 L→P | QIAEAVRPIMDSLHMAAR |

TABLE 1-continued

| SEQ ID NO: | Description | Sequence |
|---|---|---|
| 16 | Mfn2-367-384 L→G, ΔI | QIAEAVRGMDSLHMAAR |
| 17 | Mfn2-398-418 | QDRLKFIDKQLELLAQDYKLR |
| 18 | Mfn2-398-418 L→G (HR1-398-418Gly) "TetherX1" | QDRLKFIDKQGELLAQDYKLR |
| 19 | Mfn2-398-418 L→P | QDRLKFIDKQPELLAQDYKLR |
| 20 | Mfn2-428-448 | RQVSTAMAEEIRRLSVLVDDY |
| 21 | Mfn2-428-448 L→G | RQVSTAMAEEIRRGSVLVDDY |
| 22 | Mfn2-428-448 L→P | RQVSTAMAEEIRRPSVLVDDY |
| 23 | Mfn2-367-384Gly-TAT | QIAEAVRGIMDSLHMAARGGYGRKKRRQRRR |
| 24 | Mfn2-398-418Gly-Tat | QDRLKFIDKQGELLAQDYKLRGGYGRKKRRQRRR |
| 25 | Tat carrier moiety | YGRKKRRQRRR |
| 26 | Carrier moiety | RRRQRRKKRGY |
| 27 | Carrier moiety | RKKRRQRRR |
| 28 | Carrier moiety | THRLPRRRRRR |
| 29 | Carrier moiety | GGRRARRRRRR |
| 30 | Carrier moiety | RRQRRTSKLMKR |
| 31 | Carrier moiety | GWTLNSAGYLLGKINLKALAALAKKIL |
| 32 | Carrier moiety | WEAKLAKALAKALAKHLAKALAKALKCEA |
| 33 | Carrier moiety | RQIKIWFQNRRMKWKK |
| 34 | linker | GGGG |
| 35 | linker | GSGGS |
| 36 | linker | GGGS |
| 37 | linker | GGSGG |
| 38 | linker | GSGSG |
| 39 | linker | GSGGG |
| 40 | linker | GGGSG |
| 41 | linker | GSSSG |
| 42 | linker | GGSG |
| 43 | TetherX-C | GELLAQDYKLR |
| 44 | TetherX-N | QDRLKFIDKQG |
| 45 | TetherX-C-linear fusion | GELLAQDYKLRGGYGRKKRRQRRR |
| 46 | TetherX-N-linear fusion | QDRLKFIDKQGGYGRKKRRQRRR |
| 47 | GoFuse-N | QIAEAVRG |
| 48 | GoFuse-C | GIMDSLHMAAR |
| 49 | GoFuse-N-linear fusion | QIAEAVRGGYGRKKRRQRRR |
| 50 | GoFuse-C-linear fusion | GIMDSLHMAARGGYGRKKRRQRRR |

TABLE 1-continued

| SEQ ID NO: | Description | Sequence |
|---|---|---|
| 51 | GoFuse consensus variant | GIMX2X1LX2X1X2AX1 |
| 52 | GoFuse consensus variant | GMX2X1LX2X1X2AX1 |
| 53 | GoFuse fusion activating variant | GIMDDLHMAARGGYGRKKRRQRRR |
| 54 | GoFuse fusion activating variant | GIMD**(p)S**LHMAARGGYGRKKRRQRRR* |
| 55 | GoFuse fusion activating variant | GIMASLHMAARGGYGRKKRRQRRR |
| 56 | GoFuse fusion activating variant | GIMDSAHMAARGGYGRKKRRQRRR |
| 57 | GoFuse fusion activating variant | GIMDSLAMAARGGYGRKKRRQRRR |
| 58 | GoFuse fusion non-activating variant | GIADSLHMAARGGYGRKKRRQRRR |
| 59 | GoFuse fusion non-activating variant | GIMDALHMAARGGYGRKKRRQRRR |
| 60 | GoFuse fusion non-activating variant | GIMDCLHMAARGGYGRKKRRQRRR |
| 61 | GoFuse fusion non-activating variant | GIMDNLHMAARGGYGRKKRRQRRR |
| 62 | GoFuse fusion non-activating variant | GIMDGLHMAARGGYGRKKRRQRRR |
| 63 | GoFuse fusion non-activating variant | GIMDSLHAAARGGYGRKKRRQRRR |
| 64 | TetherX-C fusion-suppressing variant | GELLAQAYKLRGGYGRKKRRQRRR |
| 65 | TetherX-C fusion-suppressing variant | GELLAQDYKARGGYGRKKRRQRRR |
| 66 | TetherX-C fusion non-inhibit variant | GALLAQDYKLRGGYGRKKRRQRRR |
| 67 | TetherX-C fusion non-inhibit variant | GEALAQDYKLRGGYGRKKRRQRRR |
| 68 | TetherX-C fusion non-inhibit variant | GELAAQDYKLRGGYGRKKRRQRRR |
| 69 | TetherX-C fusion non-inhibit variant | GELLAADYKLRGGYGRKKRRQRRR |
| 70 | TetherX-C fusion non-inhibit variant | GELLAQDAKLRGGYGRKKRRQRRR |
| 71 | TetherX-C fusion non-inhibit variant | GELLAQDYALRGGYGRKKRRQRRR |
| 72 | TetherX-C fusion non-inhibit variant | GELLAQDYKLAGGYGRKKRRQRRR |
| 73 | GoFuse fusion activating variant | GIMXXXXIVAAR |
| 74 | TetherX-C fusion-suppressing peptide | GELLAQXYIOCR |
| 75 | GoFuse fusion activating variant | GIMDDLHMAAR |
| 76 | GoFuse fusion activating variant | GIMD**(p)S**LHMAAR* |

TABLE 1-continued

| SEQ ID NO: | Description | Sequence |
|---|---|---|
| 77 | GoFuse fusion activating variant | GIMASLHMAAR |
| 78 | GoFuse fusion activating variant | GIMDSAHMAAR |
| 79 | GoFuse fusion activating variant | GIMDSLAMAAR |
| 80 | GoFuse fusion non-activating variant | GIADSLHMAAR |
| 81 | GoFuse fusion non-activating variant | GIMDALHMAAR |
| 82 | GoFuse fusion non-activating variant | GIMDCLHMAAR |
| 83 | GoFuse fusion non-activating variant | GIMDNLHMAAR |
| 84 | GoFuse fusion non-activating variant | GIMDGLHMAAR |
| 85 | GoFuse fusion non-activating variant | GIMDSLHAAAR |
| 86 | TetherX-C fusion-suppressing variant | GELLAQAYKLR |
| 87 | TetherX-C fusion-suppressing variant | GELLAQDYKAR |
| 88 | TetherX-C fusion non-inhibit variant | GALLAQDYKLR |
| 89 | TetherX-C fusion non-inhibit variant | GEALAQDYKLR |
| 90 | TetherX-C fusion non-inhibit variant | GELAAQDYKLR |
| 91 | TetherX-C fusion non-inhibit variant | GELLAADYKLR |
| 92 | TetherX-C fusion non-inhibit variant | GELLAQDAKLR |
| 93 | TetherX-C fusion non-inhibit variant | GELLAQDYALR |
| 94 | TetherX-C fusion non-inhibit variant | GELLAQDYKLA |

*(p)S indicates a phosphorylated serine residue

DETAILED DESCRIPTION

I. Definitions

As used in this specification, the singular forms “a,” “an,” and “the” include plural referents unless the context clearly dictates otherwise. Thus, for example, reference to a “polymer” includes a single polymer as well as two or more of the same or different polymers, reference to an “excipient” includes a single excipient as well as two or more of the same or different excipients, and the like.

Where a range of values is provided, it is intended that each intervening value between the upper and lower limit of that range and any other stated or intervening value in that stated range is encompassed within the disclosure. For example, if a range of 1% to 8% is stated, it is intended that 2%, 3%, 4%, 5%, 6%, and 7% are also explicitly disclosed, as well as the range of values greater than or equal to 1% and the range of values less than or equal to 8%.

The terms “polypeptide,” “peptide,” and “protein,” used interchangeably herein, refer to a polymeric form of amino acids of any length, which can include genetically coded and non-genetically coded amino acids, chemically or biochemically modified or derivatized amino acids, and polypeptides having modified peptide backbones. The term includes fusion proteins, including, but not limited to, fusion proteins with a heterologous amino acid sequence, fusions with heterologous and homologous leader sequences, with or without N-terminal methionine residues; immunologically tagged proteins; and the like.

The terms “nucleic acid molecule” and “polynucleotide” are used interchangeably and refer to a polymeric form of nucleotides of any length, either deoxyribonucleotides or ribonucleotides, or analogs thereof. Non-limiting examples of polynucleotides include linear and circular nucleic acids, messenger RNA (mRNA), cDNA, recombinant polynucleotides, vectors, probes, and primers.

The terms "modulatory peptide," "mitochondrial modulatory peptide," "regulatory peptide," or "mitochondrial regulatory peptide" are used interchangeably herein to refer to the peptides described herein which function to either activate or inhibit mitochondrial fission as well as to activate or inhibit one or more functions associated with mitochondrial fission as described herein.

The term "FRET" as used herein refers to fluorescence resonance energy transfer between molecules. In FRET methods, one fluorophore is able to act as an energy donor and the other of which is an energy acceptor molecule. These are sometimes known as a reporter molecule and a quencher molecule respectively. The donor molecule is excited with a specific wavelength of light for which it will normally exhibit a fluorescence emission wavelength. The acceptor molecule is also excited at this wavelength such that it can accept the emission energy of the donor molecule by a variety of distance-dependent energy transfer mechanisms. Generally the acceptor molecule accepts the emission energy of the donor molecule when they are in close proximity (e.g., on the same, or a neighboring molecule). See for example U.S. Pat. Nos. 5,707,804, 5,728,528, 5,853,992, and 5,869,255 (for a description of FRET dyes), T Mergny et al., (1994) Nucleic Acid Res. 22:920-928, and Wolf et al., (1988) Proc. Natl. Acad. Sci. USA 85:8790-8794 (for general descriptions and methods for FRET), each of which is hereby incorporated by reference in its entirety.

"Treating" or "treatment" of a condition or disease includes: (1) preventing at least one symptom of the conditions, i.e., causing a clinical symptom to not significantly develop in a mammal that may be exposed to or predisposed to the disease but does not yet experience or display symptoms of the disease, (2) inhibiting the disease, i.e., arresting or reducing the development of the disease or its symptoms, or (3) relieving the disease, i.e., causing regression of the disease or its clinical symptoms.

A "therapeutically effective amount" or "efficacious amount" means the amount of a compound that, when administered to a mammal or other subject for treating a disease, is sufficient, in combination with another agent, or alone (e.g., in monotherapy) in one or more doses, to effect such treatment for the disease. The "therapeutically effective amount" can vary depending on the compound, the disease and its severity and the age, weight, etc., of the subject to be treated.

II. Mitofusins

Mitofusins (Mfn) belong to a class of highly conserved GTPases which are located on the outer membrane of mitochondria in mammals, flies, the worm and budding yeast. Each of Mfn1 and Mfn2, the mitofusins present in mammals, are anchored to the outer membrane by two transmembrane domains such that their N-terminus and C-terminus are exposed to the cytoplasm. Mitofusins on different organelles undergo trans-dimerization through antiparallel binding of their extended carboxy terminal α-helical domains to form mitochondria-mitochondria tethers—the obligate initial step in mitochondrial fusion (Koshiba et al., 2004, Science, 305:858-861). Conventional wisdom is that mitofusins exist constitutively in this "active" extended molecular conformation which supports mitochondrial tethering, although other possible conformations and the likelihood of functionally relevant molecular plasticity have not been rigorously tested. The components involved in mitochondrial tethering involve intermolecular and possibly intramolecular interactions of particular Mfn1 and Mfn2 domains. These interactions were further studied and exploited in the design and testing of compositions which affect the interactions and the resultant mitochondrial function.

Figure 1B:
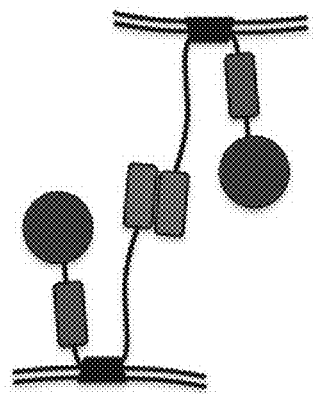

Mfn1 and Mfn2 share a common domain structure, illustrated in FIG. 1A. The amino terminal GTPase domain is followed by a coiled-coiled heptad repeat region (HR1), two adjacent small transmembrane domains, and a carboxyl terminal coiled coiled heptad repeat region (HR2). Amino acid conservation between Mfn1 and Mfn2 varies by domain, being most highly conserved in the GTPase, transmembrane, and HR2 domains (FIGS. 1C-1D, amino acid residue numbering corresponds to numbering in FIG. 1A). HR2 domains extending from Mfn1 molecules located on different mitochondria can bind to each other, forming inter-molecular HR2-HR2 interactions that link the molecules and tether the organelles (FIG. 1B) (Koshiba et al. ibid). HR2 can also bind to HR1 (Huang et al., 2011, PLoS One, 6:e20655), although there has been no determination of whether this is an inter- or intra-molecular interaction.

Figure 3A:
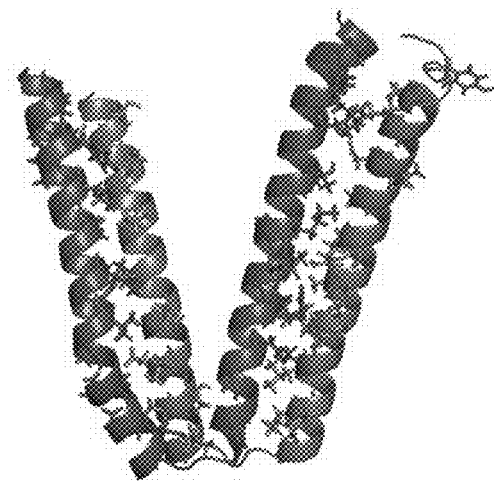
FIGS. 3A-3C provide ribbon structures to show interaction of Mfn HR1 and HR2 domains (FIG. 3A), interaction of Mfn HR1 and HR2 domains in the core of the mature protein (FIG. 3B), and extension of an HR2 domain for tethering (FIG. 3C).
Figure 3B:
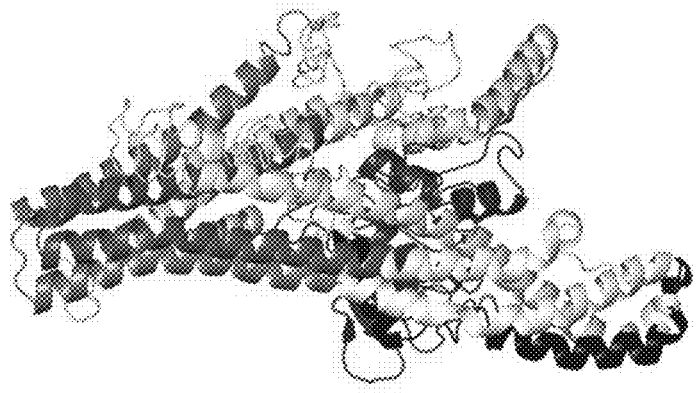
Figure 3C:
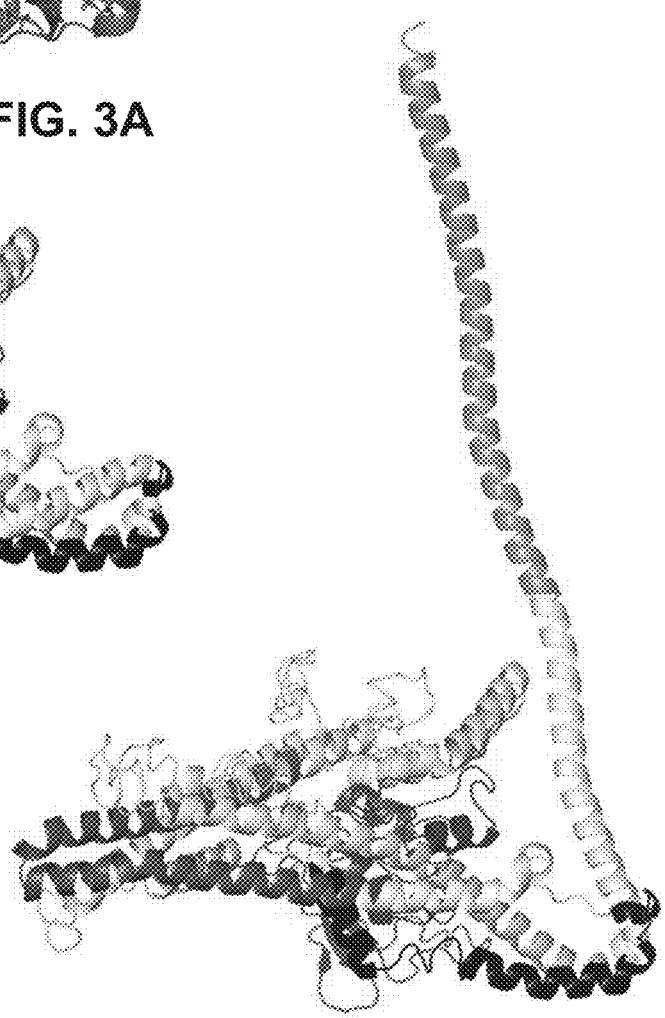

The crystal structure of bacterial dynamin-like protein (DLP) (Low and Lowe, 2006, Nature, 444:766-769; Protein Data Bank (PDB) ID No. 2J69) was used to model Mfn2 structure. The domain sequences of the DLP and Mfn2 proteins were aligned. The alignment and modeling of Mfn2 based on the DLP structure provided a template for the expansion and refining of the identities of HR2 amino acids that mediate inter-molecular HR2-HR2 tethering (Koshiba et al., 2004, Science, 305:858-861). This analysis led to the novel conception that these same amino acids mediate inter-molecular antiparallel binding of HR2 to HR2 (FIG. 2A) and intra-molecular antiparallel binding of HR2 to HR1 (FIG. 2B). FIGS. 3A-3B illustrate the antiparallel interaction by providing the hMfn2-HR2 sequence in a C-terminal to N-terminal direction. Without being bound by theory, it is predicted that the α-helix of HR1 unfolds locally at amino acids 384-387 (REQQ), creating a bend in HR1 that is contained within the core Mfn2 globular structure. Similarly, the α-helix of HR2 unfolds locally at amino acids 712-715 (QEIA), creating a bend in HR2 analogous to the bend in HR1. As illustrated in FIG. 3A, the α-helices of HR1 and HR2, each containing a central bend as described above, are able to interact with one-another in an antiparallel configuration at the Mfn2 core. This HR2-constrained configuration due to the antiparallel binding would not be conducive for mitochondrial tethering, which requires that HR2 be liberated from HR1 and extended into the canonical tethering-permissive structure. FIGS. 3B-3C illustrate a model of the Mfn2 protein structure in two configurations: one in which HR1 and HR2 are interacting or bound to one-another at the Mfn2 core (FIG. 3B) and one in which HR2 has been liberated from HR1 and extends outward as an arm FIG. 3B). Based on the modeling and subsequence prediction of HR1-HR2 interaction and its effect on mitochondrial tethering and fusion, peptides were rationally designed to have modulatory activity whereby the peptides can either facilitate or inhibit mitochondrial fusion.

As described herein, peptides were designed to mimic the structure of HR1 on either side of the REQQ bend in Mfn2 HR1. As described in Example 2, two peptides where designed which essentially flanked the REQQ bend. The first peptide comprises the sequence of human Mfn2 residues 367-384 and is referred to herein as "Mfn2-367-384." The second peptide comprises the sequence of human Mfn2 residues 398-418 and is referred to herein as "Mfn2-398-418." As a control peptide, a peptide comprising human Mfn2 residues 428-448 was also designed and is referred to herein as "Mfn2-428-448." The peptides were designed to be approximately 20 amino acids in length in order to preserve the predicted alpha-helical structure of the HR1 region. Additionally, the peptides were modified by substituting a central leucine (L) residue with a glycine or a proline (P). The glycine can add flexibility to the peptide by causing a local unfolding within the helix yet maintaining the predicted helical structure. Conversely, the proline can significantly or fully disrupt the alpha helical structure of the peptide. The sequences of each peptide are provided in Table 2 below. The position in which the leucine residue substituted in the peptide variants is indicated in bold font.

TABLE 2

| SEQ ID NO: | Description | Sequence |
|---|---|---|
| 8 | HR1 fragment (Mfn2 348-421) | FQNFERRFEECISQSAVKTKF EQHTVRAKQIAEAVRLIMDSL HMAAREQQVYCEEMREERQDR LKFIDKQLELLAQDYKLRIKQ |
| 13 | Mfn2-367-384 | QIAEAVRLIMDSLHMAAR |
| 14 | Mfn2-367-384 L→G | QIAEAVRGIMDSLHMAAR |
| 15 | Mfn2-367-384 L→P | QIAEAVRPIMDSLHMAAR |
| 17 | Mfn2-398-418 | QDRLKFIDKQLELLAQDYKLR |
| 18 | Mfn2-398-418 L→G | QDRLKFIDKQGELLAQDYKLR |
| 19 | Mfn2-398-418 L→P | QDRLKFIDKQPELLAQDYKLR |
| 20 | Mfn2-428-448 | RQVSTAMAEEIRRLSVLVDDY |
| 21 | Mfn2-428-448 L→G | RQVSTAMAEEIRRGSVLVDDY |
| 22 | Mfn2-428-448 L→P | RQVSTAMAEEIRRPSVLVDDY |

Figure 4A:
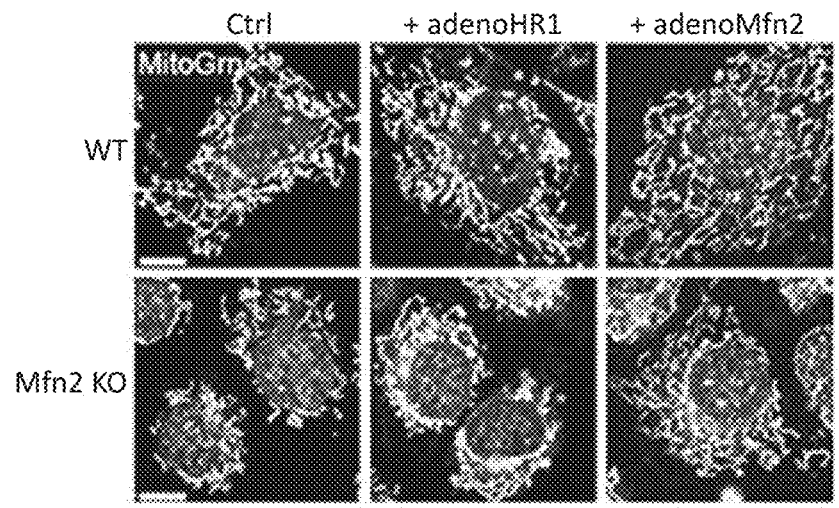
FIGS. 4A-4B show effects of mitochondrial fusion regulatory proteins on aspect ratio and mitochondrial depolarization.

The effect of each of the peptides listed in Table 1 on mitochondrial function was tested in a cell culture system using murine embryonic fibroblasts (MEFs) as described in Example 4. Wild-type MEFs express both Mfn1 and Mfn2. Also used were MEFs in which the Mfn2 gene was knocked out (MEF Mfn2 KO). The details of the experiments are provided in Example 3. In these experiments, the MEFs were infected with adenovirus (AV) engineered to express one of the peptides or full-length Mfn2 as a control. Mitochondrial fusion activity was measured using confocal microscopy and quantitative analysis of the mitochondrial aspect ratio which is a measurement of mitochondria length/width and is an accepted index of mitochondrial fusion. FIG. 4A shows a confocal microscopic image of cells treated as described in Example 3. As with all confocal microscopic images provided herein, treated cells were stained to allow quantitative assessment of mitochondrial aspect ratio and polarization using methods routine in the art. In Examples 4-8, MitoTracker Green is used to stain the mitochondria to allow measurement of mitochondrial length and width to determine the aspect ratio. Red TMRE is used to measure mitochondrial polarization (membrane potential). Blue Hoechst stains nuclei.

Figure 4B:
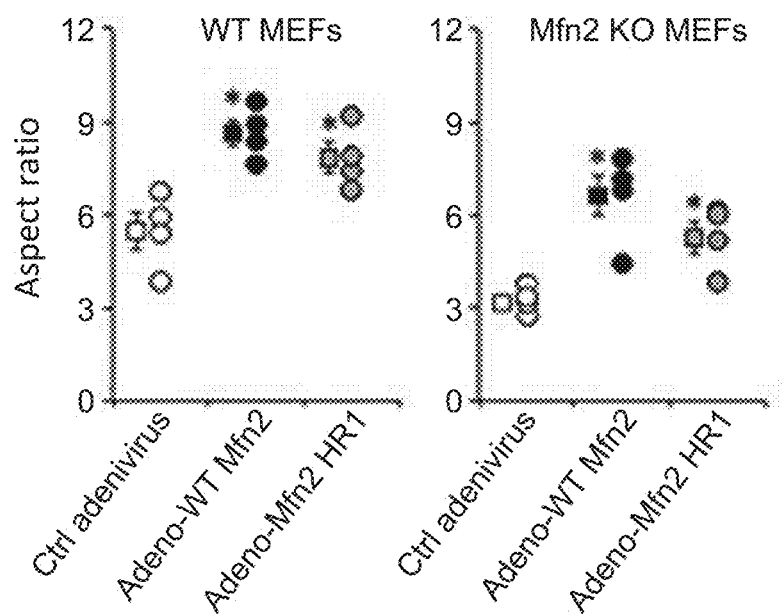

As shown in FIGS. 4A-4B, expression of the HR1 domain in both wildtype (WT) and Mfn2 null cells increased mitochondrial aspect ratio. These results indicate that intramolecular HR1-HR2 binding can be as important as intermolecular HR2-HR2 binding for mitofusin functioning as the Mfn2 null cells express only Mfn1.

Experiments with the various HR1 peptides described in Table 1 were performed to identify specific regions within HR1 that interact with and constrain HR2 as suggested in FIG. 3. Again, WT MEFs and Mfn2 KO MEF cells were infected with adenovirus engineered to express peptides of Table 1 or full-length Mfn2 as described in Example 4.

Figure 5A:
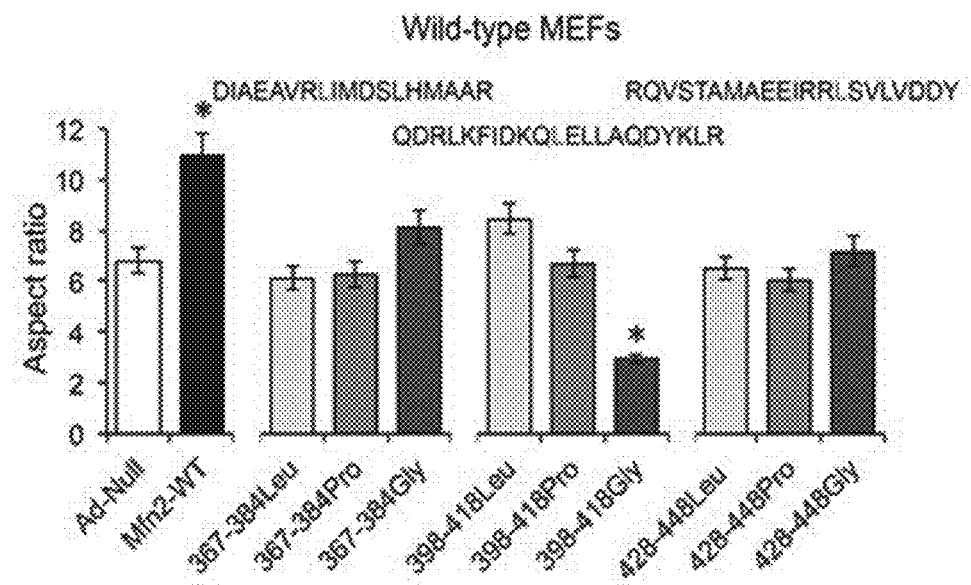
FIGS. 5A-5B show effects of mitochondrial fusion regulatory peptides on mitochondrial aspect ratio in wild-type (WT) MEFs (FIG. 5A) and Mfn2 knock-out (KO) MEFs (FIG. 5B).
Figure 5B:
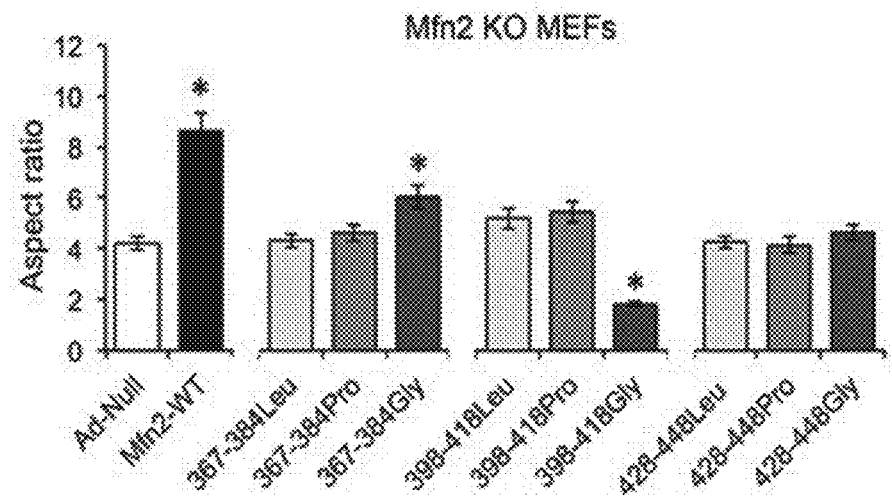

The non-HR1 peptide Mfn2-428-448 and its substitution variants did not affect mitochondrial fusion (mitochondrial aspect ratio (FIGS. 5A-5B). In contrast, Mfn2-367-384Gly (SEQ ID NO:14; alternatively referred to as GoFuse1) and Mfn2-398-418Gly (SEQ ID NO:18, alternatively referred to as TetherX1") consistently altered mitochondrial aspect ratio in both WT MEFs and Mfn2 KO MEFs. Remarkably, Mfn2-367-384Gly promoted fusion whereas Mfn2-398-418Gly potently suppressed fusion (FIGS. 5A-5B).

Figures 6A, 6B:
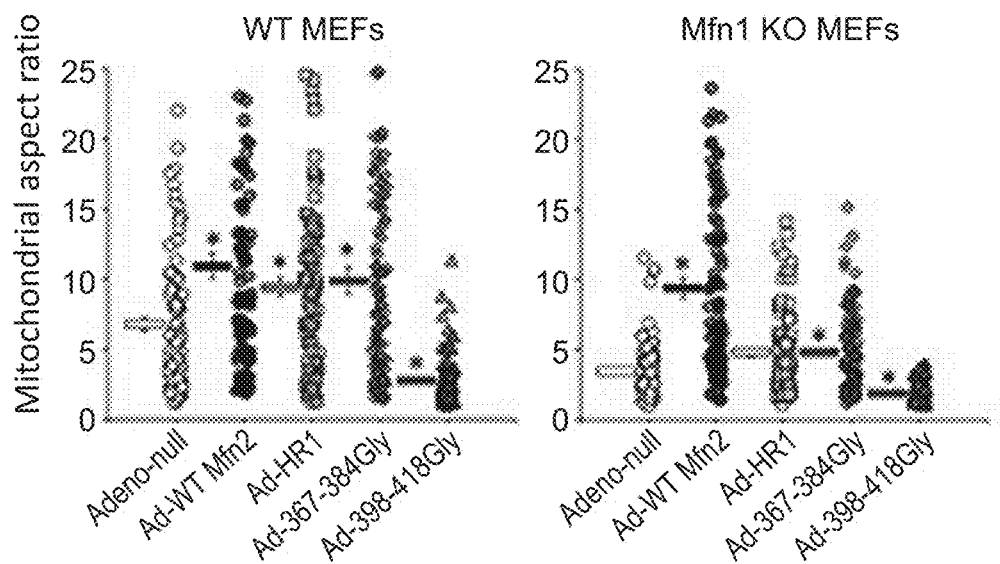
FIGS. 6A-6D show effects of mitochondrial fusion regulatory peptides on mitochondrial aspect ratio in WT MEFs (FIG. 6A), Mfn1 KO MEFs (FIG. 6B), Mfn2 KO MEFs (FIG. 6C) and Mfn1/Mfn2 double knock-out (DKO) MEFs (FIG. 6D).
Figures 6C, 6D:
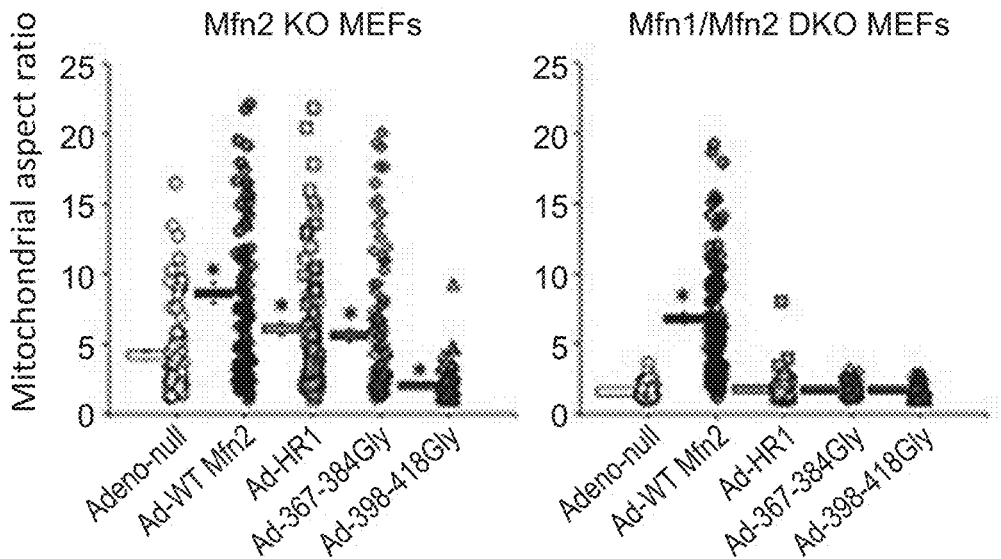

The effects of Mfn2-367-384Gly and Mfn2-398-418Gly on mitochondrial aspect ratio were then tested in MEFs having different Mfn expression profiles: WT MEF, Mfn2 KO MEF, MEFs engineered to knock out Mfn1 expression (Mfn1 KO MEF), and MEFs engineered to knock out both Mfn1 and Mfn2 (Mfn1/Mfn2 DKO). The data are presented in FIGS. 6A-6D and show that mitochondrial elongation provoked by the Mfn2-367-384Gly peptide was comparable to that produced by adeno-HR1 (FIGS. 6A-6D), whereas mitochondrial shortening by Mfn2-398-418Gly was similar to combined deletion of Mfn1 and Mfn2 (FIG. 6D). These data show that Mfn2 HR1-derived Gly peptides modulated mitochondrial fusion mediated by either Mfn1 (in Mfn2 null MEFs) or Mfn2 (in Mfn1 null MEFs). The absence of peptide effects in cells lacking both Mfn1 and Mfn2 (FIG. 6D) demonstrates that fusion modulation by Mfn2 HR1-derived peptides is the specific consequence of their acting on endogenous mitofusins, and are not off-target effects.

Polarization status of the mitochondria was also studied and the data show that modulation of mitochondrial fusion by Mfn2-367-384Gly and Mfn2-398-418Gly did not adversely impact mitochondrial polarization status (FIG. 7A) or Parkin recruitment and mitophagy induced by mitochondrial depolarization which are also impacted by Mfn1 or Mfn2 (Chen et al., 2013, Science, 340:471-475; Gong et al., 2015, Science, 350:aad2459-2451-2459-2459).

Figure 8B:
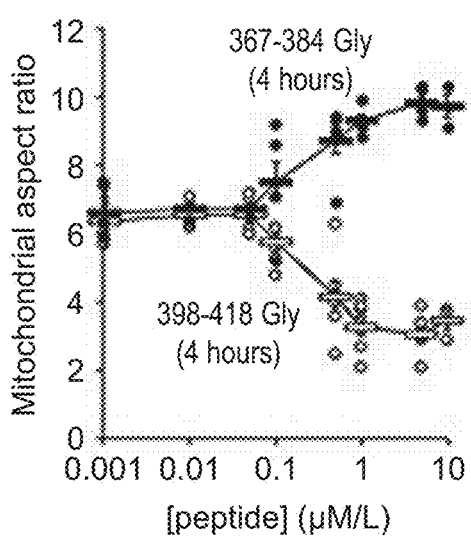
Figure 8C:
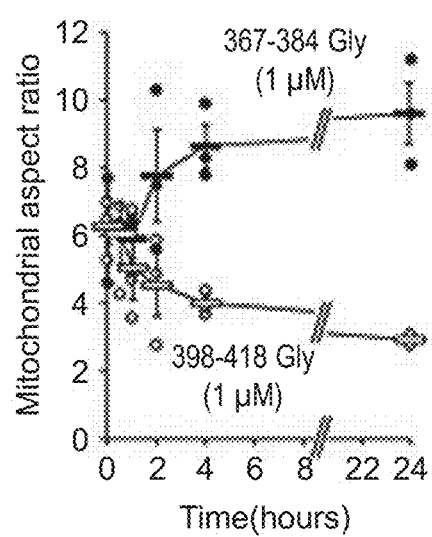
Figures 9A, 9B:
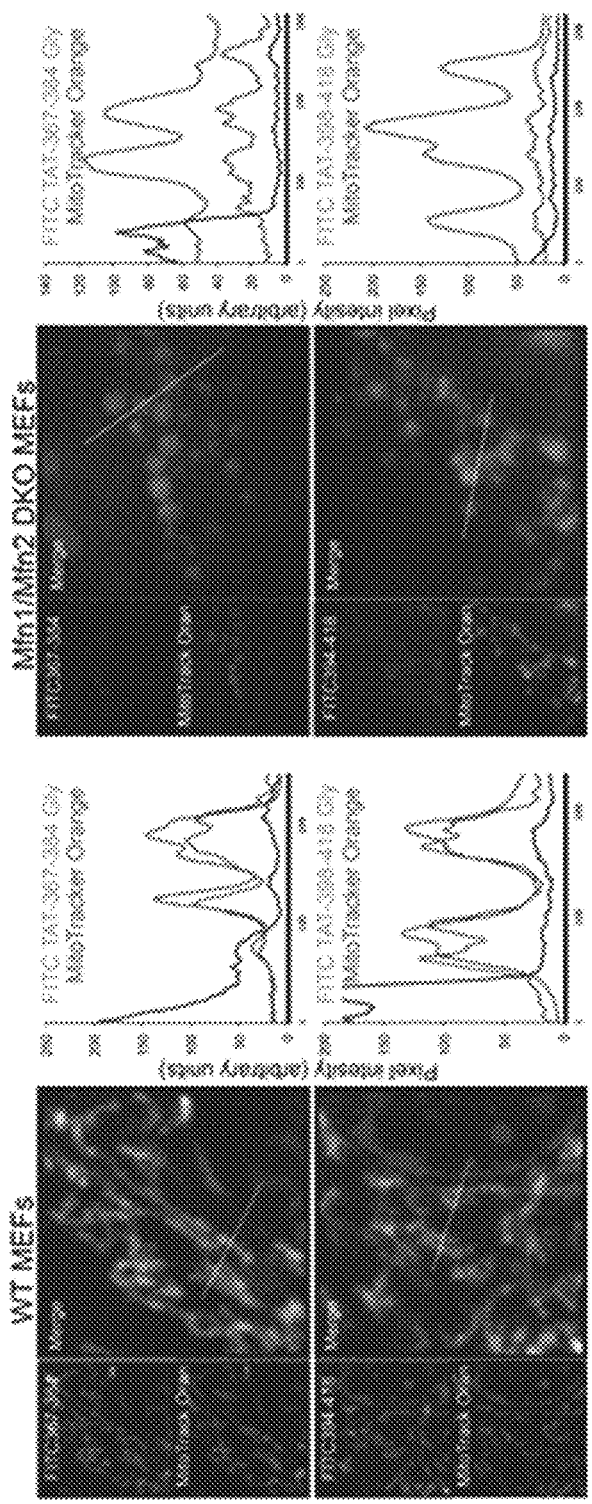
FIGS. 9A-9B show results of a study to demonstrate binding of mitochondrial fusion regulatory peptides to mitochondria in WT MEFs (FIG. 9A) or MEFs completely lacking Mfn1 and Mfn2 (FIG. 9B).
Figure 10:
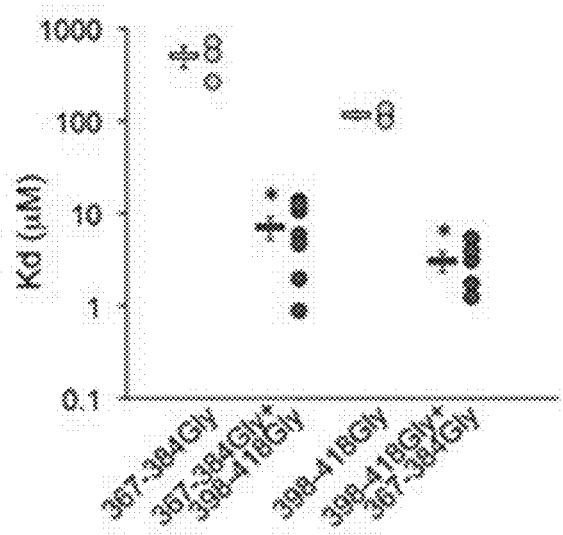
FIG. 10 illustrates results of a study to show binding of mitochondrial fusion regulatory peptides to a mitofusin immobilized on a solid substrate.
Figure 11:
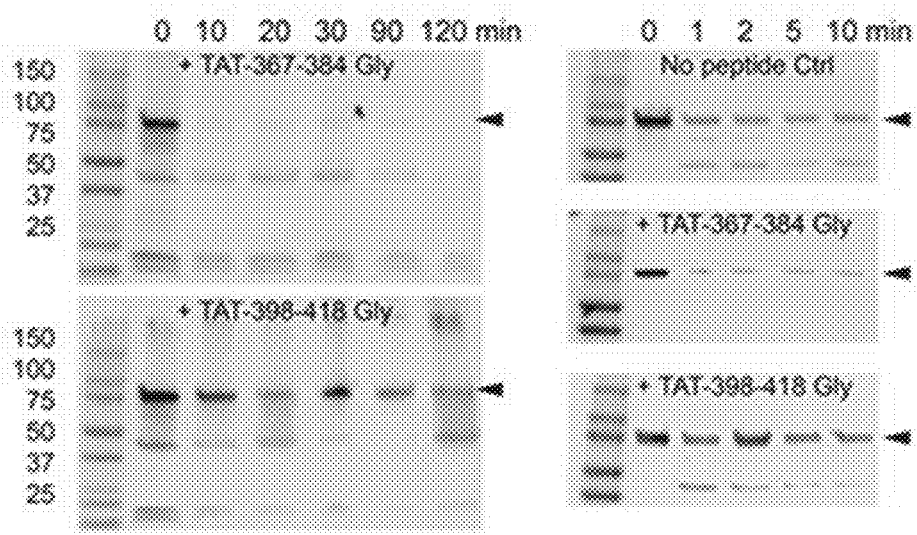
FIG. 11 shows results of a study to demonstrate the effects of mitochondrial fusion regulatory peptides on carboxyl terminal-directed proteolytic digestion of a mitofusin.

Based on the studies described above and in Examples 2-4, mitochondrial fusion modulatory peptide constructs were generated in which modulatory Mfn2 peptides described in Table 1 were conjugated to a carrier peptide which can cause the transport of the peptide construct from the extracellular environment across the cell membrane and into the cell. To do this, the modulatory peptides were conjugated to the TAT carrier peptide, referred to as $TAT_{47-57}$ or TAT and having the amino acid sequence YGRKKRRQRRR (SEQ ID NO:25). In this particular experiment, the TAT peptide was linked to the Mfn2 peptide via a dipeptide GG linker to form a linear peptide comprising, in an N-terminal to C-terminal direction, the Mfn2 peptide, a GG linker, and the $TAT_{47-57}$ peptide. The constructs were applied to cultured MEFs as described in Example 5 and the data showed that both the Mfn2-367-384Gly and Mfn2-398-418Gly Tat conjugates modulated mitochondrial aspect ratio in WT MEFs. Specifically, Mfn2-367-384Gly-TAT (QIAEAVRGIMDSLHMAARGGYGRKKRRQRRR (SEQ ID NO:23)) increased the mitochondrial aspect ratio while Mfn2-398-418Gly-Tat QDRLKFIDKQGELLAQDYKLRGGYGRKKRRQRRR (SEQ ID NO:24)) decreased mitochondrial aspect ratio in both a dose-response (FIG. 8B) and time-course (FIG. 8C) study. Notably, these cell permeant peptides affected mitochondrial morphology without affecting Mfn2 GTPase activity, mitochondrial polarization or cell viability. Studies described in Example 6 were performed to provide insight into mechanism of action. These studies confirmed that the TAT-conjugated Mfn2 HR1 minipeptides bind specifically to mitochondrial mitofusins (FIGS. 9A-9B, FIG. 10). Additionally, carboxypeptidase assays showed that TAT-367-384Gly facilitates physical exposure of the Mfn2 C-terminal HR2 domain whereas TAT-398-418Gly suppressed exposure of the Mfn2 C-terminal HR2 domain (FIG. 11). Accordingly, it can be asserted that the effects of Mfn2 HR1-derived minipeptides on mitochondrial fusion are derived from the ability of these peptides to bind to and to promote or suppress Mfn2 unfolding and HR2 extension.

Studies were also done to show that mitochondrial fusion regulating peptides and compositions described herein are able to regulate mitochondrial morphological abnormalities such as those associated with CMT2A Mfn2 mutations. As described in Example 7 and FIGS. 12-14, Mfn2-367-384Gly-TAT (SEQ ID NO: 23) normalized mitochondrial aspect ratio of Mfn2 knock-out MEFs while Mfn2-398-418Gly-Tat (SEQ ID NO:24) exaggerated mitochondrial shortening in these cells. Moreover, Mfn2-367-384Gly-TAT was able to reverse mitochondrial fragmentation in cells expressing the Mfn2 T105M mutation. Treatment of cells expressing the Mfn2 T105 mutant protein with Mfn2-367-384Gly-TAT also showed greatly improved mitochondrial polarization status and corrected mitochondrial clumping.

Figure 16A:
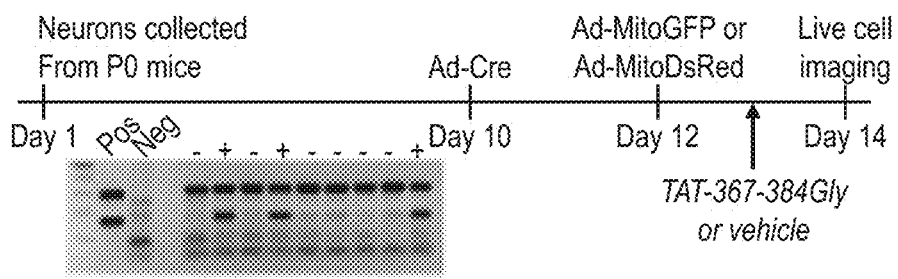
FIGS. 16A-16E show results of experiments to test the effects of mitochondrial fusion regulatory peptides on hippocampal and cortical neurons.
Figure 16B:
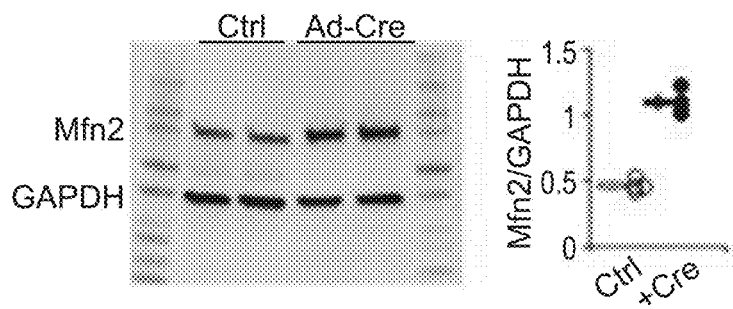
Figure 16C:
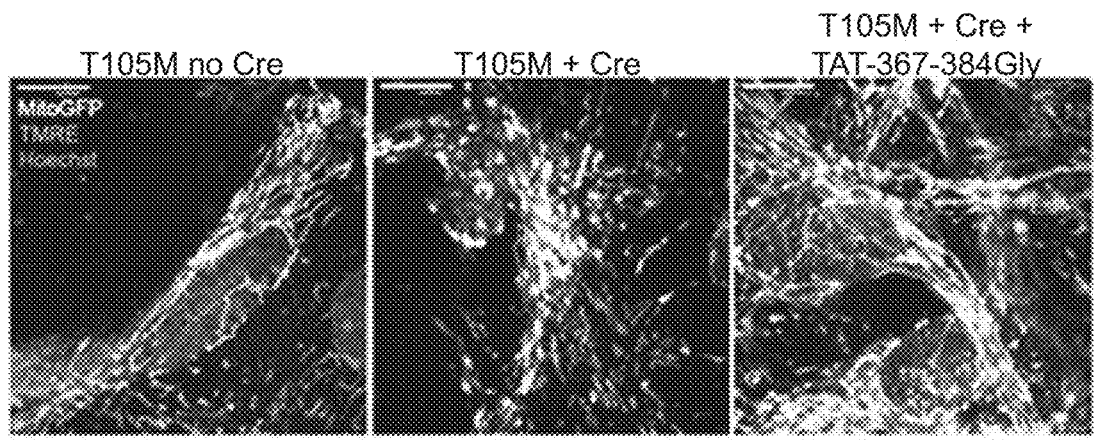

The ability of the minipeptides to repair neuronal CMT2A pathology was also studied as described in Example 8. Cultured rat motor neurons infected with adeno-Mfn2 K109A developed mitochondrial fragmentation that was fully normalized by TAT-367-384Gly (FIGS. 16A-16C). Similarly, hippocampal and cortical neurons cultured from mouse pups carrying the conditional Mfn2 T105M fl/st expression allele were used, having widespread neuronal mitochondrial dysmorphology with fragmentation and partial depolarization. Treatment with TAT-367-384Gly largely reversed these abnormalities (FIGS. 16C-16F).

By combining computational modeling based on the crystal structure of bacterial dynamin-like protein with functional interrogation of intra-molecular interactions using engineered competing peptides we provide evidence for two functionally distinct conformational states of mammalian mitofusins. Opposing effects of the engineered minipeptides on mitochondrial fusion were linked to their reciprocal modulation of mitofusin HR1 folding/unfolding. The canonical representation of Mfn1 and Mfn2 as described by Chan and colleagues (Koshiba et al., 2004, Science, 305: 858-862) is a molecule anchored to the outer mitochondrial membrane by a transmembrane domain and with both amino and carboxyl structures extending perpendicularly into the cytosol. This approximates the unfolded mitofusin conformation optimal for mitochondrial tethering and therefore permissive for fusion. However, the data and analysis described herein suggests that, like bacterial DLP (Low and Lowe, 2006, Nature, 444:766-769), the core globular Mfn molecule is adherent to the mitochondrial membrane. In the resting or tethering non-permissive state HR2 is restrained by its antiparallel intra-molecular binding to HR1; destabilization of HR1-HR2 binding unfolds and extends HR2 into the cytosol, i.e. into a tethering-permissive state. If one considers the extended active Mfn conformation to be like an inter-molecular hand shake, then the inactive folded conformation is like an intra-molecular self-hug.

The folded HR2-constrained and unfolded HR2-extended conformations indicated by our findings do not represent a strictly binary system. Rather, there must be a continuum of mitofusin structural configurations reflecting multiple intermediate transition states. Such conformational plasticity has important implications for mitochondrial gap distance maintained by Mfn-Mfn tethering, variously reported as 78±37A (Picard, et al., 2015, Nat Commun, 6:6259) or 159±30A (Koshiba et al., 2004, Science, 305:858-862). Based on a calculated HR2 arm length of 150 A beginning from the putative Gly "shoulder" at the carboxyl terminus of the transmembrane domain (hMfn1 Gly 623; hMfn2 Gly 642), and accounting for the 60 amino acid overlap of the HR2-HR2 homodimer, the maximal tethered mitochondrial gap distance according to this model would be 245 A. However, flexing of each Mfn HR2 at its shoulder would retract tethered mitochondria into close juxtaposition, narrowing the gap. The crystal structure of bacterial DLP indicates that GTP binding promotes its dimerization at the GTP domains 11. The same GTP-dependent even for Mfn2 would, in the context of concomitant trans-dimerization via HR2 domains, create a miltimeric molecular "zipper" between two adjoining mitochondria, greatly facilitating GTP-dependent outer membrane fusion. Thus, Mfn structural malleability may be important not only to initiate tethering, but to facilitate the progression from organelle tethering to apposition to union. Because conformational remodeling by the minipeptides directly impacts Mfn-mediated organelle tethering, it is likely the minipeptides will also affect tethering-dependent mitochondrial-endoplasmic reticulum calcium cross-talk (de Brito and Scorrano, 2008, Nature, 456:605-610).

It is worth noting that in designing the mitofusin conformation-altering minipeptides described herein, it was considered that it might be difficult to destabilize the constrained Mfn structure using peptide sequences identical to the parent HR1 domains with which they were intended to compete. Accordingly, rotational Gly residues were substituted for Leu residues facing away from the putative HR1-HR2 (367-384Gly) and HR2-HR2 (398-418Gly) interaction sites. The importance of minipeptide flexibility at these sites was confirmed by functional inactivation after substituting rigid Pro resides at the same positions.

The fusogenic cell-permeant peptide, TAT-367-384Gly, reversed mitochondrial dysmorphology and depolarization in otherwise normal MEFs and cultured neurons expressing either the artificial GTPase-deficient K109A Mfn2 mutant or the naturally occurring human CMT2A GTPase mutant, Mfn2 T105M. Because TAT-367-384Gly did not correct mitochondrial pathology induced by Mfn2 K109A in mitofusin null cells, we conclude that rescue of the in vitro CMT2A models accrues from enhanced mitochondrial tethering (and therefore fusion) mediated by endogenous normal Mfn1 and Mfn2. Most cases of CMT2A, including those linked specifically to Mfn2 T105M, are autosomal dominant, i.e. they have one mutant Mfn2 allele, one normal Mfn2 allele, and two normal Mfn1 alleles (Bombelli et al., 2014, JAMA Neurol, 71:1036-1042). These endogenous normal mitofusins provide a substrate for therapeutic intervention. Thus, rather than exclusively relying on genetic engineering to correct or silence Mfn2 gene mutations, an approach of pharmacologically promoting mitofusin unfolding to enhance mitochondrial tethering and fusion could prove beneficial in CMT2A and pathophysiolgically-related diseases.

III. Peptide Modulators of Mitofusin Function and Mitochondrial Fusion

Peptides which modulate mitochondrial fusion are provided herein based on the modeling, rational peptide design and experimental studies described above and in Examples 1-6 below. Specifically, modeling allowed the identification of peptide sequences that correspond to a helical structure within the HR1 domain of a mitofusin protein. Moreover, modeling in view of the Drp protein allowed identification of residues within the helical structures which interact with an HR2 domain. Taken together, it was possible to design peptides which maintain a helical structure capable of interacting with mitofusin HR1 and/or HR2 domains.

The sequence of the HR1 domain of the Mfn1 protein is FQNFEQIFEECISQSAVKTKFEQHTIRAKQILATVKNIMDSVNLAAEDKRHYSVEEREDQIDR LDFIRNQ (SEQ ID NO:7). The sequence of the HR1 domain of the Mfn2 protein is FQNFERRFEECISQSAVKTKFEQHTVRAKQIAEAVRLIMDSLHMAAREQQVYCEEMREERQ DRLKFIDKQ (SEQ ID NO:8). The two sequences are 64% identical along their entire lengths and are predicted to form a helical structure wherein a bend between two α-helices is created by residues EDKR of Mfn1 and REQQ of Mfn2. Based on this new determination of the HR1 α-helical structure with a predicted bend, modulatory peptides were designed to correspond to an α-helix on either side of the bend, specifically FQNFEQIFEECISQSAVKTKFEQHTIRAKQILATVKNIMDSVNLAAE (SEQ ID NO:9) and HYSVEEREDQIDRLDFIRNQMNLLTLDVKKK (SEQ ID NO:10) for Mfn1 and FQNFERRFEECISQSAVKTKFEQHTVRAKQIAEAVRLIMDSLHMAAR (SEQ ID NO:11) and VYCEEMREERQDRLKFIDKQQLELLAQDYKLR (SEQ ID NO:12) for Mfn2.

In a preferred embodiment, a biologically active peptide which can modulate mitochondrial fusion when introduced into a cell or representative in vitro system corresponds to a variant of the HR2 sequence QIAEAVRLIMDSLHMAAR (SEQ ID NO:13; alternatively referred to herein as HR1-367-384). As noted above, it was discovered that substitution of the L at position 8 of SEQ ID NO:14 with a G resulted in a peptide which increased mitochondrial aspect ratio in both wildtype MEFs and MEFs in which Mfn2 has been knocked-out. Accordingly, a preferred peptide for modulating mitochondrial fusion comprises the sequence QIAEAVRGIMDSLHMAAR (SEQ ID NO:14), alternatively referred to herein as HR1-367-384Gly, however, it is understood that the L at position 8 of SEQ ID NO:11 can be substituted by any residue which might increase flexibility of the predicted α-helix without impacting the structure and/or function of the peptide, i.e., in some embodiments, the L at position 8 can be substituted with an A or V.

Based on the studies described herein, an ordinarily skilled artisan can determine amino acid substitutions which may be introduced into the peptide of SEQ ID NO:13 without disrupting the structure of the peptide or impacting the functional effects of the modulatory peptide on mitochondrial fusion. Moreover, in view of the assays described herein, one having ordinary skill in the art could readily identify variants of SEQ ID NO:14 which can activate or increase mitochondrial fusion as measured by mitochondrial aspect ratio.

Based on the structure models using Dlp, peptides and compositions comprising the peptides are provided here which either inhibit or facilitate mitochondrial fusion. These fusion modulatory peptides are 16-22, 17-19, 18-20, or about 16, 17, 18, 19, 20, 21 or 22 amino acids in length and comprise a peptide having the consensus sequence $X_1X_2AX_1X_2VX_1GX_1MX_2X_1LX_2X_1X_2AX$ (SEQ ID NO:4) where $X_1$ can be a charged amino acid such as R, K, D, N, Q, E or H. In some embodiments, $X_1$ is D or E. In other embodiments, $X_1$ is R, K or H. In the above peptide sequence, $X_2$ can be a non-charged (neutral) amino acid selected from the group consisting of I, L, V, A, M, C, S, T and G. In some embodiments, $X_2$ is I, L, V, or A. In some embodiments, the modulatory peptide comprises the sequence of SEQ ID NO:4, wherein amino acids at only 1, 2 or 3 positions within SEQ ID NO:4 are substituted wherein the substitutions are according to the preceding embodiments.

Also provided based on experiments described in Examples 1-6 are peptides which can inhibit mitochondrial fusion. Such peptides are variants of the HR1 sequence C-terminal to the bend in the HR1 sequence (residues 398-418 of Mfn2; QDRLKFIDKQLELLAQDYKLR (SEQ ID NO:16), alternatively referred to herein as HR1-398-418). In a preferred embodiment, the L at position 11 of SEQ ID NO:16 is replaced with a G (QDRLKFIDKQGELLAQDYKLR (SEQ ID NO:18), alternatively referred to herein as HR1-398-418Gly. As with HR1-367-384, it is understood that any one or more of the amino acid residues of SEQ ID NO:18 can be replaced with a residue which represents a conservative substitution. For example, Q can be replaced with R, L or H, L, D can be replaced with Q, L can be replaced with V, I or M, K can be replaced with R or H, F can be replaced with W, I can be replaced with L, V, or M, E can be replaced with D, and/or A can be replaced with G, V or L.

The present studies arose in part from the idea that it would be difficult to "pry open" the constrained structure of Mfn1 or Mfn2 using a peptide that is identical in sequence to the sequence with which it will compete within the protein. This realization gave rise to the identification of peptides which can activate or inhibit mitochondrial fusion through modification of Mfn1 and/or Mfn2 function. The peptides described herein represent surprising and unexpected results regarding the sequence of the active peptides. Importantly, amino acid residues were identified in the HR1 regions which are important for forming contacts with the HR2 domain (e.g., see FIG. 2B). Moreover, it was unexpectedly determined that shortening the alpha helix turn from 5 amino acids to 4 to make it a tighter turn, e.g., by removing Mfn2 I375 which faces away from the interaction site between HR2 and HR1, resulted in a peptide which activates mitochondrial fusion. Also, it was discovered that by substituting L374 (which faces away from the interaction site of HR2 and HR1 with glycine increased flexibility of the peptide to generate a peptide able to activate fusion. The importance of increased flexibility at this position (approximately position 375) was evidenced in part by replace L374 with a proline residue which resulted in a rigid and inactive peptide.

In some aspects of the present disclosure, use of the modulatory peptides to regulate mitochondrial fusion in cells can be studied by linking the modulatory peptide to a transport moiety which can facilitate uptake of the peptide (and peptide-carrier conjugate by a cell. The transport moiety can alternatively be referred to, for example, as a transport peptide, a carrier peptide or a carrier moiety. There are many transport peptides known in the art, any of which are applicable for use with the modulatory peptides.

"Carrier moiety" refers to a polypeptide, polynucleotide, carbohydrate, or organic or inorganic compound that facilitates traversing a lipid bilayer, micelle, cell membrane, organelle membrane, or vesicle membrane. A carrier moiety attached to another molecule facilitates the molecule traversing a membrane, for example going from extracellular space to intracellular space, or cytosol to within an organelle. In some cases, a carrier moiety facilitates crossing the blood-brain barrier. The carrier peptide can be a polypeptide having a length of from about 5 amino acids (aa) to about 50 aa, e.g., from about 5 aa to about 10 aa, from about 10 aa to about 15 aa, from about 15 aa to about 20 aa, from about 20 aa to about 25 aa, from about 25 aa to about 30 aa, from about 30 aa to about 40 aa, or from about 40 aa to about 50 aa.

Exemplary protein transduction domains which may be linked to the mitochondrial fusion modulatory peptide include but are not limited to a minimal undecapeptide protein transduction domain corresponding to residues 47-57 of human immunodeficiency virus-1 (HIV-1) TAT (GenBank Acc. No. AEB53027; or variations thereof including YGRKKRRQRRR (SEQ ID NO:25), RRRQRRK-KRGY (SEQ ID NO:26), RKKRRQRRR (SEQ ID NO:27), THRLPRRRRRR (SEQ ID NO:28); and GGRRARRRRRR (SEQ ID NO:29)). a polyarginine sequence comprising a number of arginines sufficient to direct entry into a cell (e.g., 3, 4, 5, 6, 7, 8, 9, 10, or 10-50 arginines); a VP22 domain (Zender et al. (2002) Cancer Gene Ther. 9(6):489-96); an Drosophila Antennapedia protein transduction domain (Noguchi et al. (2003) Diabetes 52(7):1732-1737); a truncated human calcitonin peptide (Trehin et al. (2004) Pharm. Research 21:1248-1256); polylysine (Wender et al. (2000) Proc. Natl. Acad. Sci. USA 97:13003-13008); an arginine homopolymer of from 3 arginine residues to 50 arginine residues; RRQRRTSKLMKR (SEQ ID NO:30); Transportan GWTLNSAGYLLGKINLKALAALAKKIL (SEQ ID NO:31); KALA WEAKLAKALAKALAKHLAKALAKA-LKCEA (SEQ ID NO:32); and RQIKIWFQNRRMKWKK (SEQ ID NO:33).

There are alternative ways to link the carrier moiety to the mitochondrial fusion modulatory peptide. In some embodiments, a carrier moiety is covalently linked to the amino terminus of the modulatory peptide or to the carboxyl terminus of a modulatory peptide. In preferred embodiments, the carrier moiety is linked to the N-terminus or the C-terminus of the modulatory peptide by a peptide bond.

When the modulatory peptide is linked to a carrier peptide by a peptide bond, there may be a linker between the modulatory and carrier peptides. The linker may be a peptide having any of a variety of amino acid sequences. A linker which is a spacer peptide can be of a flexible nature, although other chemical linkages are not excluded. A linker peptide can have a length of from about 1 amino acid to about 40 amino acids, e.g., from about 1 amino acid (aa) to about 5 aa, from about 5 aa to about 10 aa, from about 10 aa to about 20 aa, from about 20 aa to about 30 aa, or from about 30 aa to about 40, in length. These linkers can be produced using synthetic, linker-encoding oligonucleotides to couple the proteins. Peptide linkers with a degree of flexibility can be used. The linking peptides may have virtually any amino acid sequence, where in some embodiments the linker peptide will have a sequence that results in a generally flexible peptide. The use of small amino acids, such as glycine and alanine, are of use in creating a flexible peptide. The creation of such sequences is routine to those of skill in the art. Various linkers are commercially available and are considered suitable for use.

Suitable linkers can be readily selected and can be of any of a suitable of different lengths, such as from 1 amino acid (e.g., Gly) to 40 amino acids, from 2 amino acids to 15 amino acids, from 3 amino acids to 12 amino acids, including 4 amino acids to 10 amino acids, 5 amino acids to 9 amino acids, 6 amino acids to 8 amino acids, or 7 amino acids to 8 amino acids, and may be 1, 2, 3, 4, 5, 6, or 7 amino acids. In some embodiments, the linker comprises only glycines. In other embodiments, 1, 2 3 or 4 of the glycines are substituted with serines.

Exemplary flexible linker which can be used to join or link a carrier moiety to a mitochondrial fission inhibitor peptide, for example, via peptide bonds, include glycine polymers (G)n, (e.g., where n is an integer from 1 to about 20); glycine-serine polymers (including, for example, (GS)n, GSGGS (SEQ ID NO:35) and GGGS (SEQ ID NO:36), where n is an integer of at least one), glycine-alanine polymers, alanine-serine polymers, and other flexible linkers known in the art. Glycine and glycine-serine polymers are of interest since both of these amino acids are relatively unstructured, and therefore may serve as a neutral tether between components. Glycine polymers are used in some embodiments. See Scheraga, Rev. Computational Chem. 11173-142 (1992). Exemplary flexible linkers include, but are not limited to GG, GGG, GGS, GGSG (SEQ ID NO:41), GGSGG (SEQ ID NO:36), GSGSG (SEQ ID NO:37), GSGGG (SEQ ID NO:38), GGGSG (SEQ ID NO:39), GSSSG (SEQ ID NO:40), and the like.

Non-peptide linker moieties can also be used to join or link a carrier moiety to a mitochondrial fusion modulatory peptide. The linker molecules are generally about 6-50 atoms long. The linker molecules may also be, for example, aryl acetylene, ethylene glycol oligomers containing 2-10 monomer units, diamines, diacids, amino acids, or combinations thereof. Other linker molecules which can bind to polypeptides may be used in light of this disclosure.

In alternative embodiments, the modulatory peptide is linked to the carrier peptide by a disulfide bond. In some embodiments, the disulfide bond is formed between two cysteines, two cysteine analogs or a cysteine and a cysteine analog. In this embodiment, both the modulatory peptide and the carrier peptide contain at least one cysteine or cysteine analog. The cysteine residue or analog may be present as the N-terminal or C-terminal residue or as an internal residue of the modulatory peptide and of the carrier peptide. The disulfide linkage is then formed between the sulfur residues on each of the cysteine residues or analogs. Thus, the disulfide linkage may form between, for example, the N-terminus of the modulatory peptide and the N-terminus of the carrier peptide, the C-terminus of the modulatory peptide and the C-terminus of the carrier peptide, the N-terminus of the modulatory peptide and the C-terminus of the carrier peptide, the C-terminus of the inhibitor peptide and the N-terminus of the carrier peptide, or any other such combination including at any internal position within the inhibitor peptide and/or the carrier peptide.

A modulatory peptide construct according to the present disclosure can refer to a modulatory peptide and a carrier moiety, wherein the modulatory peptide and carrier moiety are linked as described above.

The peptides described herein are modulatory peptides which can activate, enhance, inhibit or eliminate mitochondrial fusion. One accepted method for monitoring mitochondrial fusion is measuring the aspect ratio, which is the ratio between the long and short axes of the mitochondrial ellipses and thus measures mitochondrial elongation and is an index of mitochondrial fusion. In other words, modulatory peptides which cause an increase in the aspect ratio are activators of mitochondrial fusion. Modulatory peptides which cause a decrease in the aspect ratio are inhibitors of mitochondrial fusion. Accordingly, one test for the effects of the modulatory peptides on mitochondrial fusion involves the effects of the peptides on mitochondrial aspect ratio. The mitochondrial aspect ratio can be measured using microscopy (e.g., confocal microscopy) to measure the length and width of mitochondria in a cell treated with a modulatory peptide compared to the same cell not treated with the peptide wherein a change in the aspect ratio indicates an effect on mitochondrial fusion. For example and as described above, addition of the HR1-367-384Gly peptide (SEQ ID NO:14), whether via adenoviral expression (Example 4) or delivery of a Tat-conjugate (Example 5) resulted in an increase in mitochondrial aspect ratio indicating that compositions comprising SEQ ID NO:14 and variants thereof are activators of mitochondrial fusion. In contrast, addition of the HR1-398-418Gly peptide (SEQ ID NO:18), whether via adenoviral expression (Example 4) or delivery of a Tat-conjugate (Example 5) resulted in a decrease in mitochondrial aspect ratio indicating that compositions comprising SEQ ID NO:18 and variants thereof are inhibitors of mitochondrial fusion.

To measure an increase or decrease of an activity or function upon treatment by a composition described herein, it is understood by the person having ordinary skill in the art that the function or activity can be measured, for example, in the presence and in the absence of the composition (e.g., mitochondrial fusion modulatory peptide or construct), and a comparison is made between the levels of the activities in the presence and absence of the composition. Alternatively, the function or activity can be measured, for example, in the presence of two separate compositions, and the levels of the activity or function in the presence of each composition are compared. An inhibition of an activity can be a reduction of about 5% to 10%, 5% to 20%, 2% to 20%, 10% to 20%, 5% to 25%, 20% to 50%, 40% to 60%, 50% to 75%, 60% to 80%, 75% to 95%, 80% to 100%, 50% to 100%, 90% to 100%, or 85% to 95% when comparing the two conditions. Similarly, activation of an activity can be a increase of about 5% to 10%, 5% to 20%, 2% to 20%, 10% to 20%, 5% to 25%, 20% to 50%, 40% to 60%, 50% to 75%, 60% to 80%, 75% to 95%, 80% to 100%, 50% to 100%, 90% to 100%, 85% to 95%, or more than 100% but less than 500%, when comparing the two conditions.

As described in Example 11, alanine scanning of the modulatory peptides was performed in order to identify amino acid residues within the TetherX-C peptide (SEQ ID NO:43) and Go-Fuse peptide (SEQ ID NO:48). The results are provided in Tables 5-8 of Example 11 and show that substitution of D414 and L417 of the TetherX-C peptide does not eliminate the fusion-suppressing activity of the TetherX-C (or TetherX-1) peptide. Also, substitution of the GoFuse D377, S378, L379 and H380 residues does not eliminate the fusion-promoting activity of the GoFuse-C (or GoFuse1) peptide. Accordingly, in some embodiments, a mitochondrial fusion activating peptide is provided, wherein the activating peptide comprises the sequence GIMXXXX-MAAR (SEQ ID NO:73). In other embodiments, a mitochondrial fusion inhibitor peptide is provided, wherein the inhibitor peptide comprises the sequence GELLAQXYKXR (SEQ ID NO:74).

A modulatory peptide or construct as described herein can be prepared by in vitro (e.g., cell-free) synthesis, using conventional methods as known in the art. Various commercial synthetic apparatuses are available, for example, automated synthesizers. By using synthesizers, naturally occurring amino acids may be substituted with unnatural amino acids. The particular sequence and the manner of preparation will be determined by convenience, economics, purity required, and the like.

If desired, various groups may be introduced into the peptide during synthesis or during expression, which allow for linking to other molecules or to a surface, or provide some other desired property such as increased solubility, increased resistance to proteolysis, increased in vivo half-life, and the like. One or more cysteines can be used to make thioethers, histidines for linking to a metal ion complex, carboxyl groups for forming amides or esters, amino groups for forming amides, and the like.

A modulatory peptide or construct as described herein can be isolated and purified in accordance with conventional methods of recombinant synthesis. A lysate may be prepared of the expression host and the lysate purified using high performance liquid chromatography (HPLC), exclusion chromatography, gel electrophoresis, affinity chromatography, or other purification technique. For the most part, the compositions which are used will comprise at least 80% by weight of the desired product, at least about 85% by weight, at least about 95% by weight, or at least about 99.5% by weight, in relation to contaminants related to the method of preparation of the product and its purification. The percentages can be based upon total protein.

A modulatory peptide or construct as described herein may be in the form of a pharmaceutically acceptable salt. Pharmaceutically acceptable salts include acid addition salts, such as hydrochloride, hydrobromide, sulfurate, nitrate, phosphorate, acetate, propionate, glycolate, pyruvate, oxalate, malate, malonate, succinate, maleate, fumarate, tartarate, citrate, benzoate, cinnamate, mandelate, methanesulfonate, ethanesulfonate, p-toluene-sulfonate, salicylate and the like, and base addition salts, such as sodium, potassium, calcium, magnesium, lithium, aluminum, zinc, ammonium, ethylenediamine, arginine, piperazine and the like.

IV. Compositions Comprising Mitofusin Modulatory Peptides

The present disclosure provides compositions comprising a mitochondrial modulatory peptide or construct. The composition can comprise, in addition to a modulatory peptide or construct, one or more of: a salt, e.g., NaCl, MgCl, KCl, $MgSO_4$, etc.; a buffering agent, e.g., a Tris buffer, N-(2-Hydroxyethyl)piperazine-N'-(2-ethanesulfonic acid) (HEPES), 2-(N-Morpholino)ethanesulfonic acid (IVIES), 2-(N-Morpholino)ethanesulfonic acid sodium salt (IVIES), 3-(N-Morpholino)propanesulfonic acid (MOPS), N-tris[Hydroxymethyl]methyl-3-aminopropanesulfonic acid (TAPS), etc.; a solubilizing agent; a detergent, e.g., a non-ionic detergent such as Tween-20, etc.; a protease inhibitor; glycerol; and the like.

Compositions comprising a modulatory construct or peptide may include a buffer, which is selected according to the desired use of the peptide, and may also include other substances appropriate to the intended use. Those skilled in the art can readily select an appropriate buffer, a wide variety of which are known in the art, suitable for an intended use.

In some cases, a modulatory construct or peptide composition is a pharmaceutical composition. A subject pharmaceutical composition can be administered to a subject in need thereof (e.g., a subject in need of inhibition of abnormal (e.g., pathological) mitochondrial fission). A subject pharmaceutical composition comprises: a) a mitochondrial fission inhibitor construct or peptide; and b) a pharmaceutically acceptable excipient, a variety of which are known in the art and need not be discussed in detail herein. Pharmaceutically acceptable excipients have been amply described in a variety of publications, including, for example, "Remington: The Science and Practice of Pharmacy", 19th Ed. (1995), or latest edition, Mack Publishing Co; A. Gennaro (2000) "Remington: The Science and Practice of Pharmacy", 20th edition, Lippincott, Williams, & Wilkins; Pharmaceutical Dosage Forms and Drug Delivery Systems (1999) H. C. Ansel et al., eds 7th ed., Lippincott, Williams, & Wilkins; and Handbook of Pharmaceutical Excipients (2000) A. H. Kibbe et al., eds., 3rd ed. Amer. Pharmaceutical Assoc.

V. Nucleic Acids Encoding the Modulatory Constructs or Peptides

The present disclosure provides synthetic nucleic acids, where a subject synthetic nucleic acid comprises a nucleotide sequence encoding a modulatory peptide or construct, e.g. Tat-fusion construct. A nucleotide sequence encoding a modulatory peptide or construct can be operably linked to one or more regulatory elements, such as a promoter and enhancer, that allow expression of the nucleotide sequence in the intended target cells (e.g., a cell that is genetically modified to synthesize the encoded mitochondrial fission inhibitor construct or peptide). In some embodiments, a subject nucleic acid is a recombinant expression vector.

A nucleotide sequence encoding a mitochondrial fission inhibitor peptide or construct can be present in an expression vector and/or a cloning vector. An expression vector can include a selectable marker, an origin of replication, and other features that provide for replication and/or maintenance of the vector.

Expression vectors generally have convenient restriction sites located near the promoter sequence to provide for the insertion of nucleic acid sequences encoding heterologous proteins (e.g., to provide for insertion of a nucleotide sequence encoding a subject variant ALDH polypeptide). A selectable marker operative in the expression host may be present. Suitable expression vectors include, but are not limited to, viral vectors (e.g. viral vectors based on vaccinia virus; poliovirus; adenovirus (see, e.g., Li et al., Invest Opthalmol Vis Sci 35:2543 2549, 1994; Borras et al., Gene Ther 6:515 524, 1999; Li and Davidson, PNAS 92:7700 7704, 1995; Sakamoto et al., H Gene Ther 5:1088 1097, 1999; WO 94/12649, WO 93/03769; WO 93/19191; WO 94/28938; WO 95/11984 and WO 95/00655); adeno-associated virus (see, e.g., Ali et al., Hum Gene Ther 9:81 86, 1998, Flannery et al., PNAS 94:6916 6921, 1997; Bennett et al., Invest Opthalmol Vis Sci 38:2857 2863, 1997; Jomary et al., Gene Ther 4:683 690, 1997, Rolling et al., Hum Gene Ther 10:641 648, 1999; Ali et al., Hum Mol Genet 5:591 594, 1996; Srivastava in WO 93/09239, Samulski et al., J. Vir. (1989) 63:3822-3828; Mendelson et al., Virol. (1988) 166:154-165; and Flotte et al., PNAS (1993) 90:10613-10617); SV40; herpes simplex virus; human immunodeficiency virus (see, e.g., Miyoshi et al., PNAS 94:10319 23, 1997; Takahashi et al., J Virol 73:7812 7816, 1999); a retroviral vector (e.g., Murine Leukemia Virus, spleen necrosis virus, and vectors derived from retroviruses such as Rous Sarcoma Virus, Harvey Sarcoma Virus, avian leukosis virus, human immunodeficiency virus, myeloproliferative sarcoma virus, and mammary tumor virus); and the like.

In some embodiments, the vector comprising a polynucleotide construct is an adenovirus vector as described in Example 4. In these embodiments, a carrier moiety is not required as the adenovirus comprising a nucleic acid encoding a modulatory peptide is introduced into a host cell where expression of the peptide occurs in vivo.

VI. Methods of Treatment

The peptides, variants thereof and conjugates or fusions thereof described herein can be used in the treatment, prevention, amelioration of diseases or disorders associated with mitochondrial dysfunction. For example, a subject suffering from or diagnosed with a disease or disorder associated with or caused by insufficient mitochondrial fusion as discussed in more detail below can be treated with a therapeutically effective amount of a modulatory peptide as disclosed herein. Clinical indications associated with mitochondrial dysfunction include but are not limited to neurodegenerative diseases such as Alzheimer's disease, Parkinson's disease, Huntington's disease, Amyotrophic lateral sclerosis, hereditary spastic paraplegia, and Friedreich's ataxia (Santel, 2006, Biochim Biophys Acta, 1763:490-499). Also included is Charcot-Marie-Tooth disease (CMT), an inherited neurodegenerative disorder. The neurodegenerative disease may be Parkinson's Disease. Other indications are diseases or disorders associated with oxidative stress and/or ischemia and include diabetes, various cancers, encephalomyopathies and neuropathies. Mfn2 gene expression was observed to be upregulated exercise and weight loss and downregulated under obese and diabetic conditions, suggesting that activators of Mfn2 function may be useful in treating indications such as type 1 or type 2 diabetes (Bach et al., 2005, Diabetes, 54:2685-2693; Mingrone et al, 2005, Diabetologia, 48:2108-2114). Subjects suffering from various cardiovascular diseases and disorders may also be treated. As described in Ong et al. (2015, Eur J Pharmacol, 763:104-114), cardiovascular diseases including coronary atherosclerosis, hypertension and pulmonary arterial hypertension are strongly associated with vascular smooth muscle cell (VSMC) proliferation and hyperplasia. Notably, Mfn2 was originally identified as a novel hyperplasia suppressor gene, capable of inhibiting VSMC proliferation in a variety of vasculo-proliferative conditions (Chen et al., 2004, Nat Cell Biol, 6:872-883). Ong et al. (2015, Eur J Pharmacol, 763:104-114) also lists inhibition of mitochondrial fission or activation of Mfn2 as possible therapeutic approaches to treating acute ischemia/reperfusion in the heart, kidney or brain, heart failure, left ventricular hypertrophy and pulmonary arterial hypertension.

The modulatory peptides as described herein may be used to treat a subject suffering from or at risk of suffering from stroke. For example, the subject may be one who has suffered from a cerebral stroke or cerebral ischemia. Alternatively, the subject has suffered ischemic damage to cardiac tissue due to stroke. As shown in Example 10, administration of a modulatory peptide according to the present embodiments reduced both direct and indirect infarct area and volume in a mammal that was subjected to temporary cerebral ischemia.

VII. Methods for Screening for Compositions which Modulate Mfn Intramolecular or Intermolecular Interactions With the modulatory peptides available which have been shown to activate mitochondrial fusion, including but not limited to a peptide having the sequence of SEQ ID NO:14 or a variant thereof, assays can be designed and performed to screen candidate agents or molecules for specific compositions which can activate mitochondrial fusion. For example, identification of small molecule activators provides an alternate modulatory composition which may be more efficient to synthesize and use. Candidate agents encompass numerous chemical classes, typically synthetic, semi-synthetic, or naturally-occurring inorganic or organic molecules. Candidate agents include those found in large libraries of synthetic or natural compounds. Alternatively, libraries of natural compounds in the form of bacterial, fungal, plant and animal extracts are available from commercial resources or are readily producible. In some embodiments, small molecule activators of mitochondrial fusion identified through these screening assays can become promising therapeutic agents for treating diseases or disorders associated with defects in mitochondrial fusion.

One screening assay can use the HR1-367-384Gly peptide or variant which has been shown to increase mitochondrial aspect ratio. In this assay, the Mfn2 protein or a fragment of the Mfn2 protein which contains the HR2 domain (comprises residues 681-757 of SEQ ID NO:2) is immobilized to a solid substrate such as nitrocellulose or to the well surface of a high throughput screen plate or array substrate. The immobilized protein or fragment is then incubated with the HR1-367-384Gly peptide or variant in a solution conducive to protein-protein interactions. The HR1-367-384Gly peptide is conjugated to a detectable label such as FITC or other fluorescent dye, generating a signal in each well or array position. Detectable labels are well-known in the art and include isotope, colorimetric, fluorescent, photochromic and electrochemical labels. A candidate agent is assessed for its ability to compete with the HR1-367-384Gly peptide for binding to the solid phase-bound Mfn2 protein or HR2 domain. An agent which can compete with the HR1-367-384Gly peptide for binding to Mfn2 protein or HR2 will reduce or eliminate the signal from the label. A candidate agent able compete with the HR1-367-384Gly peptide is an agent which can activate mitochondrial aspect ratio and/or mitochondrial fusion.

In some embodiments, a method for identifying an agent or compound able to bind to the Mfn2 protein is provided. In these embodiments, the compound competes with the HR1-367-384Gly peptide for binding to Mfn2 or to a fragment of Mfn2 comprising the HR2 domain. A test compound is identified as active it if decreases the binding of the peptide, i.e., its effect on the extent of binding is above a threshold level. More specifically, if the decrease in binding of the labeled HR1-367-384Gly peptide to the solid phase bound Mfn2 protein or HR2 domain is a several-fold different between the control and experimental samples, the compound would be considered as having binding activity. Typically, a 2-fold or 4-fold threshold difference in binding between the test and control samples is sought. In some embodiments, this agent increases the mitochondrial aspect ratio when incubated in a cell.

In some embodiments, an alternative assay is provided to identify a composition able to activate intermolecular binding of the HR2 domains of two Mfn proteins. In this assay, a first population of Mfn2 proteins is labeled with an acceptor fluorophore on its HR2 arm and a second population of Mfn2 proteins is labeled with a donor fluorophore on its HR2 arm. Use of fluorophore donors and complementary acceptor molecules for FRET analysis is well known (see, e.g., Jager et al., 2005, Protein Sci, 14:2059-2068; Jager et al, 2006, Protein Sci, 15:640-646). Accordingly, as described above, when an HR2 arm is liberated from the configuration in which it is interacting with the HR1 domain within the core of the Mfn protein, the free HR2 arm is able to interact with the free HR2 arm of a second Mfn2 to facilitate mitochondrial tethering and subsequent fusion. It follows that provided herein is an assay to screen a population of agents or compounds for those that facilitate mitochrondrial tethering and subsequent fusion wherein the population of candidate compounds is added to an array, wherein each well or position in the array contains a test reaction mix which comprises a first population of Mfn2 proteins labeled at or near the HR2 arm with a donor fluorophore and a second population of Mfn2 proteins labeled at or near the HR2 arm with a acceptor fluorophore. The fluorescence is measured in each test reaction mix and compared with a negative control reaction mix containing no HR2-binding peptide and a positive control reaction mix which contains an HR2-binding peptide and no candidate compound. A fluorescence signal which is greater in a test reaction mix containing a candidate compound is identified the candidate compound as an activator of mitochondrial fusion.

In a third screening assay, interaction between the HR1 and HR2 domains of a single Mfn2 protein is assessed. For example, a single Mfn2 protein is labeled with a single FRET donor and acceptor pair, wherein the donor is positioned at or near the HR1 domain and the acceptor is positioned at or near the HR2 domain, or vice versa. Incubation of a peptide which inhibits mitochondrial fusion (decreases mitochondrial aspect ratio) (e.g., the 367-384Gly peptide or variant thereof) will cause the HR2 arm to extend, removing the quenching action of the FRET pair, resulting in fluorescence signal. Accordingly, a library of candidate modulatory molecules can be screened by mixing each with the Mfn2 protein labeled with a FRET donor acceptor pair. Any candidate molecule which increases fluorescences of the labeled Mfn2 protein by at least 50%, 60%, 70% compared to the labeled Mfn2 protein in the absence of a candidate molecule will be identified as an activator of mitochondrial fusion.

EXAMPLES

Example 1

Materials and Methods

Cell Lines—
Wild-type murine embryonic fibroblast cells (MEFs) were prepared from E10.5 C57/b6 mouse embryos. SV-40 T antigen-immortalized Mfn1 null ("Mfn1 KO," ATCC No. CRL-2992), Mfn2 null ("Mfn2 KO," ATCC No. CRL-2993) and Mfn1/Mfn2 double null MEFs ("Mfn DKO," ATCC No. CRL-2994) were purchased from ATCC. MEFs conditionally expressing the human Mfn2 T105M mutation were prepared from E10.5 embryos of C57BL/6-Gt(ROSA)26Sor [tm1(CAG-MFN2*T105M)Dple]/J mice purchased from The Jackson Laboratory (Stock No: 025322). MEFs were maintained in DMEM containing 4.5 g/L glucose (or galactose when specified) supplemented with 10% fetal bovine serum, 1× nonessential amino acids, 2 mM L-glutamine, 100 U/ml penicillin and 100 µg/ml streptomycin.

Adenoviral Stocks—
Empty adenovirus (Ad-CMV-Null; #1300) and adenoviri expressing β-Galactosidase (Ad-CMV-b-Gal; #1080) or Cre recombinase (Ad-CMV-iCre; #1045) were from Vector Biolabs. Adenoviral expression vectors for hMfn2 HR1 and the minipeptides and Gly or Pro mutants were generated and amplified using standard methods. Adenoviral vectors were added to MEFs at 50% confluence at an MOI of 100.

Antibodies and Immunoblotting—

Rabbit polyclonal anti-Mfn1 (sc-50330, 1:200) and mouse monoclonal anti-Mfn2 (ab56889, 1:500) were from Santa Cruz and Abcam, respectively. Cell protein lysates were size-separated on 10% SDS-PAGE gels, transferred onto nylon membranes, incubated with primary antibody and detected with peroxidase-conjugated anti-mouse secondary antibody (Cell Signaling, 7076S, 1:4000) or goat anti-rabbit secondary antibody (Thermo Scientific, 31460, 1:4000) using ECL enhanced chemiluminescence substrate (PerkinElmer, NEL105001EA) on a Li—COR Odyssey system for digital acquisition.

Live Cell Imaging—

MEFs or neurons were grown on chamber slides and infected with recombinant adenoviri for 48-72 hours unless otherwise indicated. MEFs were stained with MitoTracker Green (200 nM, Invitrogen M7514) and Blue Hoechst (10 mg/ml, Invitrogen H3570), with or without tetramethylrhodamine ethyl ester (TMRE; 200 nM, Invitrogen T-669). Neuronal mitochondria were labeled with adenoviral-expressed mitoGFP plus TMRE, or with adeno-mitoDsRed for time-lapse studies. Cover slips were loaded onto a chamber (Warner instrument, RC-40LP) in modified Krebs-Henseleit buffer (138 mM NaCl, 3.7 mM KCl, 1.2 mM $KH_2PO_4$, 15 mM Glucose, 20 mM HEPES and 1 mM $CaCl_2$) at room temperature and visualized on a Nikon Ti Confocal microscope equipped with a 60×1.3 NA oil immersion objective. For mitophagy studies MEFs were stained with MitoTracker Green and infected with adeno-mcherry Parkin or stained with LysoTracker Deep Red (50 nM, Invitrogen L-7528); carbonylcyanide p-trifluoromethoxyphenylhydrazone (FCCP, 10 μM for 1 hour) was applied as a positive control. Mitochondrial fusion was measured at 2 and 6 hours after PEG-mediated cell fusion of MEFs treated 48 hours previously with adeno-mitoGFP or adeno-mitoDsRed (Chen et al., 2005, J Biol Chem, 280:26185-26192). Laser confocal fluorescence was excited at 561 nm (MitoTracker Green, GFP, FITC), 637 nm (TMRE, LysoTracker Red, mcherry-Parkin, MitoTracker Orange) or 408 nm (Blue Hoechst) laser diodes. Image analysis—Mitochondrial aspect ratio was calculated using automated edge detection and Image J software (Song et al., 2015, Cell Metab, 21:273-285). Mitochondrial depolarization was calculated as % of green mitochondria visualized on MitoTracker Green and TMRE merged images, expressed as green/(green+yellow mitochondria)×100. Parkin aggregation was calculated as % of cells with mitochondrial clumping of mcherry-Parkin (Song et al., 2015, Cell Metab, 21:273-285). Lysosomal engulfment of mitochondria was identified by colocalization of LysoTracker Red and MitoTracker Green (Song et al., 2015, Cell Metab, 21:273-285).

GTPase Assay—

Minipeptide effects on Mfn2 GTPase activity were evaluated using a modification of a previously described method (Qi X et al., 2013, J Cell Sci 126:789-802). Briefly, recombinant Mfn2 (100 ng, OriGene, Rockville, Md.) was incubated with 1 M control TAT peptide, TAT-367-384Gly, or TAT-398-418Gly for 15 minutes prior to addition of 0.5 mM GTP for 1 hour at 37° C. GTPase activity relative to no-peptide control was measured using a colorimetric GTPase assay kit (Novus Biologicals, Littleton, Colo.) following the manufacturer's instructions.

Mfn2 FRET Assay— mCerulean1 and mVenus were cloned onto the 5' and 3' ends of hMfn2 cDNA in pcDNA3.1 and confirmed by DNA sequencing. Lipofectamine-transfected biosensor-expressing FMK 293T cells were imaged on an Olympus IX81 ZDC inverted microscope under 40× magnification. mCerulean was excited at 436 nm with emission at 480 nm. mVenus was excited at 500 nm with emission at 535 nm. FRET was imaged with excitation at 436 nm and emission at 535 nm. Studies were performed after adding GTP☐S (1 mM, Sigma-Aldrich) to suppress Mfn2 GTPase activity. Live cell FRET data were acquired as described (Spiering et al., 2013, Methods Cell Biol, 114:593-609) every 60 seconds for 15 minutes before and 90 minutes after addition of TAT-minipeptides (5 ☐M).

Statistical Analyses—

Sample size for mitochondrial studies was established a priori based on published experiments having similar endpoints (Song et al., 2015, Cell Metab, 21:273-285); experimental variance was similar between study groups and cell lines. Data are reported as mean±SEM. Statistical comparisons (two-sided) used one-way ANOVA and Tukey's test for multiple groups or Student's t-test for paired comparisons. $P<0.05$ was considered significant.

Example 2

Computational Modeling of Mfn2 Structure

In order to design peptides which can bind to and modulate Mfn1 and/or Mfn2, computational modeling was performed based on the known structure of the Dpr1 protein which has significant amino acid sequence identity with both Mfn1 and Mfn2. Specifically, the I-TASSER (Iterative Threading ASSEmbly Refinement) hierarchical approach to protein structure was used to determine the structural model of MFN2 (Yang et al., 2015, Nat Methods, 12:7-8). Structural templates were identified from the PDB database through sequence similarity searches (threading). The top ten solutions were based on the bacterial dynamin-like protein (DLP) structures in the Protein Data Bank (PDB ID: 2J69; Low and Lowe, 2006, Nature, 44:766-769). The confidence of each model was quantitatively measured by C-score that was calculated based on the significance of threading template alignments and the convergence parameters of the structure assembly simulations. C-score was typically in the range of [−5, 2], where a C-score of a higher value signified a model with a higher confidence and vice-versa. C-score in the top solution was −1.14. Another measure of the quality of a predicted structure was its estimated TM score. TM-score is a scale for measuring structural similarity and is estimated based on the C-score and protein length following the correlation observed between these qualities. A TM-score >0.5 indicated a model of correct topology and a TM-score <0.17 meant a random similarity. The estimated TM-score of the top solution is 0.57±0.15. Energy minimization and analysis of the structure was performed with MAESTRO tools (Maestro, version 10.5, Schrödinger, LLC, New York, N.Y., 2016). PYMOL (The PyMOL Molecular Graphics System. Version 1.7; Schrödinger, LLC: New York, 2014) was used for preparing images and videos.

Using the DLP crystal structure (PDB ID 2J69) to model Mfn2 structure, the identities of HR2 amino acids that mediate inter-molecular HR2-HR2 tethering were expanded and refined and are shown in FIG. 2A. The DLP crystal structure led to the prediction that these same amino acids mediate intra-molecular antiparallel binding of HR2 to HR1

(FIG. 2B). The HR2 sequence of MFN2 in FIGS. 2A-B is written in a C-terminal to N-terminal direction to illustrate antiparallel interaction between the HR1 and HR2 and HR2 and HR2. Boxes indicate residues which interact. Modeling shows that the α-helix of HR1 unfolds locally at amino acids 384-387 (REQQ), creating a bend in HR1 that contains it within the core Mfn2 globular structure (FIGS. 3A-3B). Unfolding of the HR2 α-helix at amino acids 712-715 (QEIA) creates an analogous bend and permits antiparallel binding to HR1 at the Mfn core. This HR2-constrained configuration would not be conducive for mitochondrial tethering, which requires that HR2 be liberated from HR1 and extended into the canonical tethering-permissive structure (FIG. 3C).

Example 3

Modulatory Peptide Design and Synthesis

After modeling the structural interaction of the Mfn2 HR1 and HR2 domains as described in Example 1, three peptides were designed which contained an amino acid sequence derived from Mfn2 to test the concept of regulatory peptides which can affect HR1-HR2 interaction. Two peptides correspond to residues within the HR1 region of Mfn2 and flanking the HR1 REQQ bend: residues 367-384 (SEQ ID NO:13) and residues 398-418 (SEQ ID NO:17). A third peptide was designed based on the sequence of the adjacent C-terminal area between HR1 and the transmembrane domain, corresponding to residues 428-448 (SEQ ID NO:20). Because these peptides are derived from α-helical domains, the peptides were designed to have a length of about 20 amino acids in order to conserve their secondary structure. Peptides having about 20 amino acids were predicted to create a stable α-helix of about 5 turns. It was also considered that the native approximately 20 amino acid peptides might not effectively compete with the endogenous HR1-HR2 interactions as they each represent only a portion of the overall HR1 interacting domain.

Accordingly, two analogs were generated for each of the three peptides, substituting either glycine or proline for a mid-peptide leucine. It was predicted that substituting glycine for the central leucine residue would increase rotational flexibility of the peptide and enhance its ability to compete for and interfere with endogenous inter-domain interactions in intact Mfn2. Conversely, substitution with proline, which can break α-helical structure, were predicted to result in peptides which were less active as the α-helix structure would be kinked, thus limiting competition for endogenous interactions. The nine peptides were synthesized using routine chemical peptide synthesis methods and are summarized in Table 3 below. Bold font indicates the lysine residue which was substituted with either glycine or proline.

TABLE 3

| SEQ ID NO: | Description | Sequence |
|---|---|---|
| 13 | Mfn2 367-384 | QIAEAVRLIMDSLHMAAR |
| 14 | Mfn2 367-384 L→G | QIAEAVRGIMDSLHMAAR |
| 15 | Mfn2 367-384 L→P | QIAEAVRPIMDSLHMAAR |
| 17 | Mfn2 398-418 | QDRLKFIDKQLELLAQDYKLR |
| 18 | Mfn2 398-418 L→G | QDRLKFIDKQGELLAQDYKLR |

TABLE 3-continued

| SEQ ID NO: | Description | Sequence |
|---|---|---|
| 19 | Mfn2 398-418 L→P | QDRLKFIDKQPELLAQDYKLR |
| 20 | Mfn2 428-448 | RQVSTAMAEEIRRLSVLVDDY |
| 21 | Mfn2 428-448 L→G | RQVSTAMAEEIRRGSVLVDDY |
| 22 | Mfn2 428-448 L→P | RQVSTAMAEEIRRPSVLVDDY |

Example 4

Effects of Adenoviral-Expressed Modulatory Peptides on HR Interactions

Each of the nine peptides described in Table 3 were tested to study the concept of conformational reversibility for Mfn function, whether or not each peptide could mediate intra-molecular HR1-HR2 or inter-molecular HR2-HR2 binding, and their effects on mitochondrial fusion and function in the cell.

First, an adenovirus which recombinantly expressed the hMfn2 HR1 binding fragment (adeno HR1) was introduced into MEFs. It was reasoned that competition of the intra-molecular HR1-HR2 interaction by free HR1 fragment would increase mitochondrial fusion. Indeed, adeno-HR1 increased mitochondrial aspect ratio (length/width; an index of mitochondrial fusion) in both wildtype (WT) and Mfn2 null (Chen et al., 2003, J Cell Biol, 160:189-200) MEFs (FIGS. 4A-4B). FIG. 4A provides merged confocal images of the MEFs infected with adenoviri expressing β-gal (Ctrl), hMfn2 HR1 fragment, or intact fully functional hMfn2. MitoTracker Green (MitoGrn) stains mitochondria and red TMRE indicates mitochondrial polarization. Blue Hoechst stains nuclei. Scale bars are 10 microns. Quantitative results for the confocal images are presented in FIG. 4B. *=P>0.05 vs. Ctrl (ANOVA); #=P<0.05 vs. HR1 in 4 independent experiments for each condition. This result indicated that intra-molecular HR1-HR2 binding can be as important as inter-molecular HR2-HR2 binding for mitofusin functioning.

To identify specific regions within HR1 that interact with and constrain HR2 adenoviral vectors were created which encoded one of two ~20 amino acid mini-peptides flanking the REQQ bend of the parent HR1 fragment (corresponding to residues 367-384 and residues 398-418 of hMfn2). Additionally, an adenoviral vector encoding a third mini-peptide corresponding to adjacent carboxyl-terminal sequence (hMfn2 residues 428-448) that was not predicted to bind HR2 was created. The role of α-helices in the HR1-HR2 interaction was interrogated by engineering into each mini-peptide mutations substituting glycines (Gly, which increases flexibility in the secondary structure due to its small side chain) or prolines (Pro, which breaks the α-helix structure) for centrally positioned leucines (Leu) (see Table 3). The nine adenovirally-encoded peptides were expressed in wild type (WT) and Mfn2-deficient MEFs, and mitochondrial aspect ratio was compared to cells infected with empty adenovirus ("Ad-Null" negative control) or adeno-Mfn2 (Mfn2 positive control). Shown in FIG. 5A-5B are results of adenovirus expression in WT MEFs (FIG. 5A) and in Mfn2 KO MEFs (FIG. 5B) for each of negative control, WT control, HR1-367-384, HR1-398-418, and Mfn2-428-448 peptides and variants thereof. The non-HR1 peptide adeno428-448 and its mutants did not affect mitochondrial fusion. In contrast, adeno367-384Gly and adeno398-418Gly consistently altered mitochondrial aspect ratio. Remarkably, adeno367-384 Gly promoted fusion whereas adeno398-418 Gly potently suppressed fusion (FIGS. 5A-5B).

Figure 7A:
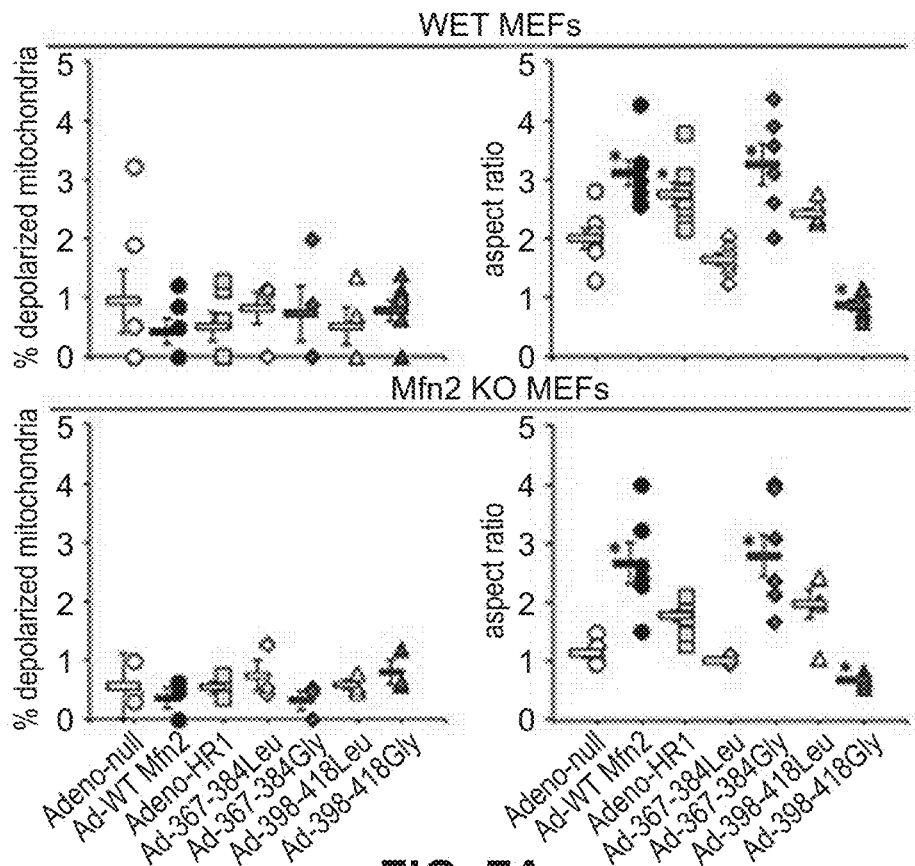
FIGS. 7A-7B show effects of mitochondrial fusion regulatory peptides on mitochondrial polarization and aspect ratio. Quantitative results are provided in FIG. 7A (mitochondrial polarization, left panel; aspect ratio, right panel) with the corresponding confocal microscopy images provided in FIG. 7B.
Figure 7B:
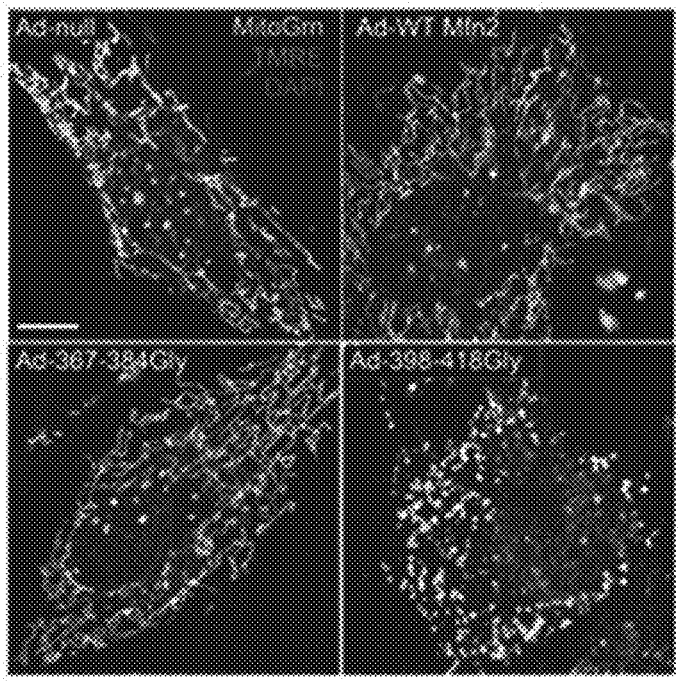

The consequences of adeno367-384 Gly and adeno398-418 Gly on a range of mitochondrial functions in MEFs having different Mfn expression profiles were examined. Also examined were the effects of the adenovirally expressed peptides compared to fully functional adeno-Mfn2 or the catalytically inactive parent adeno-HR1 fragment. Quantitative results for each of the adenoviral expression constructs are shown in FIGS. 6A-6D, in which the constructs were used to infect WT MEFs (FIG. 6A), Mfn1 KO MEFs (FIG. 6B), Mfn2 KO MEFs (FIG. 6C) or Mfn1/Mfn2 DKO MEFs (FIG. 6D). Each point is the aspect ratio of an individual mitochondrion (n~100 mitochondria from 4 or 5 separate experiments). Adeno-HR1 and its analog Gly-substituted peptides altered mitochondrial aspect ratio in MEFs expressing Mfn1 or Mfn2 in any combination. Mitochondrial elongation provoked by adeno367-384Gly was comparable to that produced by adeno-HR1 in each of the 4 expression systems, whereas mitochondrial shortening by adeno398-418Gly was similar to combined deletion of Mfn1 and Mfn2. Thus, Mfn2 HR1-derived Gly peptide modulated mitochondrial fusion mediated by either Mfn1 (in Mfn2 null MEFs) or Mfn2 (in Mfn1 null MEFs). An absence of peptide effects in cells lacking both Mfn1 and Mfn2 (FIG. 6D) demonstrates that fusion modulation by Mfn2 HR1-derived peptides is the specific consequence of their acting on endogenous mitofusins, and not off-target effects. Modulation of mitochondrial fusion by adeno367-384Gly and adeno398-418Gly did not adversely impact mitochondrial polarization status. Quantitative analysis data are provided in FIG. 7A showing the lack of adverse impact with representative merged confocal images of WT MEFs infected with ad-Mfn2 or the two biologically active Ad-peptides are shown in FIG. 7B (scale bar is 10 microns). Each point is the mean of ~20 mitochondria from ~5 cells in N=3 to 8 (polarization) and N=6 to 9 (aspect ratio) independent experiments (=P<0.05 vs ad-null Ctrl (ANOVA)).

Also studied were the effects of the adenoviral expression of WT Mfn2, HR1 peptide, adeno367-384 and its glycine variant and adeno398-418 and its glycine variant on Parkin recruitment and mitophagy induced by mitochondrial depolarization which are also impacted by the Mfn1 and Mfn2 proteins (Chen et al., 2013, Science, 340:471-475; Gong G. et al., 2015, Science, 350:aad2459). These studies were performed using WT MEFs and Mfn2 KO MEFs. No significant effects were observed due to expression of the various peptides (data not shown).

Example 5

Active Cellular Uptake of Mfn Modulatory Peptides

Based on these results of Example 4, fusion-promoting 367-384Gly and fusion-inhibiting 398-418Gly peptides were synthesized as C-terminal $TAT_{47-57}$ conjugates to study the effects of these peptides on mitochondrial and cellular function. $TAT_{47-57}$ is a well-characterized "carrier" peptide able to promote active cellular peptide uptake. Specifically, a linear peptide was constructed in which the hMfn2 modulatory peptide was linked by a peptide bond at its C-terminus to a Gly-Gly dipeptide linker whose C-terminus was linked by a peptide bond to the $TAT_{47-57}$ peptide having the sequence YGRKKRRQRRR (SEQ ID NO:25). The resultant linear fusion-promoting peptide conjugate comprises the sequence QIAEAVRGIMDSLHMAARGGYGRKKRRQRRR (SEQ ID NO:23). The fusion-inhibiting linear peptide has the sequence QDRLKFIDKQGELLAQDYKLRGGYGRKKRRQRRR (SEQ ID NO:24). Except for dose-response studies, stock concentrations of TAT-minipeptides in sterile water were applied to cultured MEFs at a dilution factor of 1:2000 to achieve final concentrations of 1 or 5 µM.

Figure 8A:
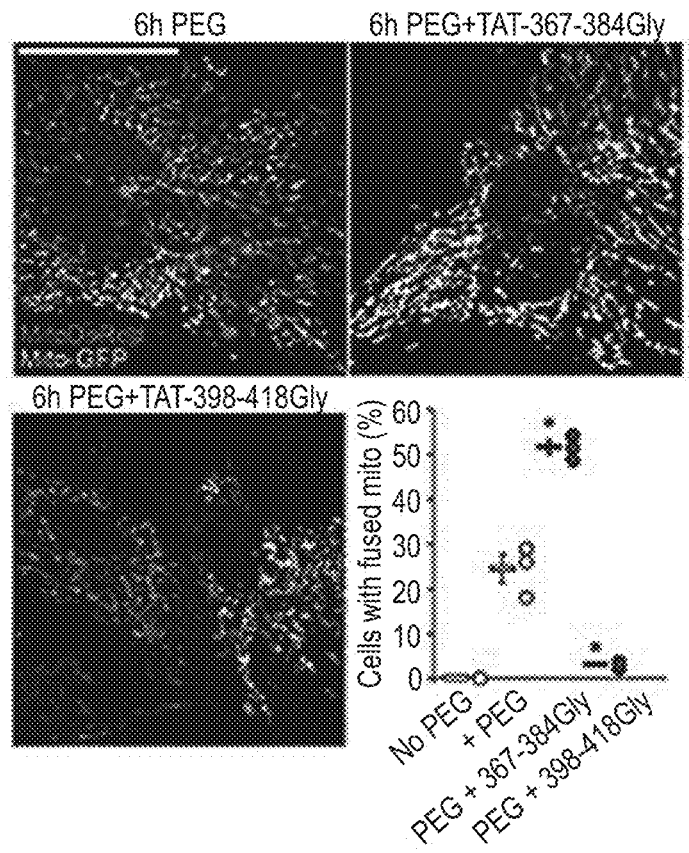
FIGS. 8A-8C show effects of mitochondrial fusion regulatory peptides on mitochondrial aspect ratio in a dose-response study. Mitochondrial fusion measured by organellar contents mixing is provided in the confocal microscopy images in FIG. 8A. Results of a dose-response study and a time-course study is illustrated in FIGS. 8B and 8C, respectively.

The functional consequences of the Mfn2 HR1-derived peptides were defined after synthesizing them as C-terminal $TAT_{47-57}$ conjugates to promote active cellular uptake. Mitochondrial fusion can be detected by mixing of organellar contents (Chen et al., 2005, J Biol Chem, 280:26185-26192). Treatment of MEFs with 1 µM TAT-367-384Gly for 6 hours more than doubled the rate of mitochondrial content mixing, whereas 1 µM TAT-398-418Gly completely suppressed mitochondrial fusion over the same time period, as determined by mitochondrial content exchange (red-green overlay). (FIG. 8A, scale bar is 20 microns). Mitochondrial aspect ratio changed in parallel with mitochondrial mixing (FIG. 8B). $EC_{50}$ values for TAT-367-384Gly mediated mitochondrial elongation (enhanced fusion) averaged 280±90 nM, and for TAT-398-418Gly mediated mitochondrial shortening (suppressed fusion) were 250±90 nM; half-times for mitochondrial shape change were approximately 2 hours for both TAT minipeptides (FIG. 8B). Immunoblot analysis of mitochrondrial dynamics proteins 4 hours after application of TAT-367-384Gly or TAT-398-418Gly to MEFs showed that these TAT minipeptides modulated mitochondrial fusion without altering Mfn2 GTPase activity or influencing the abundance of the proteins Optic atrophy 1 (Opa1, an inner mitochondrial membrane fusion protein) and Drp1 (data not shown). Even prolonged treatment of cells with the TAT minipeptides (1 µM for 24 hours) did not impair mitochondrial polarization or cell viability, including under conditions of metabolic stress provoked by substituting galactose for glucose in the culture media (Ghelli et al., 2003, J Biol Chem, 278:4145-4150) (data not shown).

Example 6

HR1 Minipeptides Alter Mfn2 Conformation

The above results support the premise that TAT-conjugated Mfn2 minipeptides affect mitochondrial fusion by modulating Mfn1 and Mfn2 conformation according to the dynamic structure model depicted in FIGS. 3A-3C. Additional studies were performed to validate this mechanism of action using the minipeptide-Mfn2 binding assay procedure. Confocal localization of FITC-labeled TAT-minipeptides in WT MEFs and Mfn null MEFs (Mfn1/Mfn2 DKO) was used for analysis of interaction between the minipeptides and mitochondrial mitofusins. Mitochondria were stained with MitoTracker Orange; nucleus was stained with Blue Hoechst. Line-scans were generated for the confocal photographs.

The results showed that FITC-labeled TAT-peptides decorated mitochondria in WT MEFs (FIG. 9A), but not to MEFs completely lacking mitofusins (Mfn1/Mfn2 DKO MEFs) (FIG. 9B). Top panel of each FIGS. 9A and 9B shows data for TAT-367-384Gly; bottom panel of each FIGS. 9A and 9B shows data for TAT-398-418Gly. Thus, cell-internalized TAT-conjugated Mfn2 HR1 minipeptides bind specifically to mitochondrial mitofusins.

The conformational shift model presented herein predicts that destabilization of fusion-constrained highly folded Mfn2 conformation by 367-384Gly should facilitate binding of 398-418Gly to the newly extended carboxyl-terminal HR2 domain and vice versa. That is, minipeptide binding to Mfn2 should exhibit cooperativity. Accordingly, experiments were performed to analyze binding of minipeptides to Mfn2. Mfn2 was bound to carboxylic acid sites of AGILE (Nanomedical Diagnostics, San Diego Calif.) graphene chips (Mackin et al., 2016, Analyst, 141:2704-2711) as previously described (Qvit et al., 2016, J Am Chem Soc, 138:7626-7635). Minipeptides were applied at varying concentrations (500 nM-1 mM) and the change in sensor chip charge recorded for 15 min. Responses of 25 sensors on a single assay chip were averaged. A Hill equation fit was used to derive $K_d$. All samples were identical prior to allocation of treatments and analyses were performed by an observer blinded to the experimental conditions.

Indeed, binding of either minipeptide to recombinant Mfn2 immobilized on a solid matrix was enhanced 40- to 70-fold by the other (FIG. 10; n=3 studies for baseline and 6-7 studies for cooperativity. *=P<0.05 vs same peptide alone (t-test)).

To show that TAT-367-384Gly and TAT-398-418Gly modulate Mfn2 HR2 unfolding and extension using complementary methods, carboxypeptidase protection assays were performed. Mitochondrial membranes were prepared (Song et al., 2015, Cell Metab, 21:273-285) from mouse hearts overexpressing human Mfn2 (Gong et al., 2015, Science, 350:aad2459) and digested with 200 ng/ml each carboxypeptidases A and B (Sigma-Aldrich) for increasing times at room temperature, followed by immunoblotting using an antibody (Abcam ab56889) specific to hMfn2 HR2.

The results revealed that TAT-367-384Gly accelerated carboxyl terminal-directed proteolytic digestion of Mfn2, demonstrating that this peptide physically exposes the Mfn2 C-terminal HR2 domain; TAT-398-418 Gly had the opposite effect (FIG. 11). In Mfn2 live cell studies, Forster resonance energy transfer (FRET) of hMfn2 tagged at the amino terminus with mCerulean1 and the carboxyl terminus with mVenus was increased by TAT-398-418Gly, demonstrating that this peptide promotes physical localization of HR2 at the core globular Mfn2 molecule; TAT-367-384Gly had the opposite effect (data not shown).

Collectively, the data show that the effects of Mfn2 HR1-derived minipeptides on mitochondrial fusion derive from their ability to promote or suppress Mfn2 unfolding and HR2 extension.

Example 7

Rescue of Mitochondrial Dysmorphology

Enhancing Mfn1- or Mfn2-mediated mitochondrial fusion with TAT-367-384 Gly has potential to alleviate mitochondrial morphological abnormalities like those evoked in CMT2A caused by nonsense or damaging non-synonymous Mfn2 mutations (Bombelli et al., 2014, JAMA Neurol, 71:1036-1042). It was reasoned that mitochondrial morphology would improve if endogenous normal Mfn1 or Mfn2 were assisted into their active conformations in which the D2 region is extended and/or available for interaction with the D2 region of a second Mfn protein (e.g., FIGS. 1B and 3B). This notion was tested in Mfn2 KO MEFs, a cell model of Mfn2 deficiency. WT MEFs and Mfn2 KO MEFs were treated with 1 μM or 5 μM TAT-367-384Gly peptide or TAT-398-418Gly peptide. TAT-367-384Gly normalized mitochondrial aspect ratio of Mfn2 KO MEFs in 24 hours (data not shown). As expected, TAT-398-418Gly exaggerated mitochondrial shortening in Mfn2 KO MEFs (data not shown). These results reveal potent minipeptide effects of the peptides on endogenous Mfn1 and hint at therapeutic potential of mitofusin conformation manipulation in diseases caused by impairments of mitochondrial fusion.

Figure 12A:
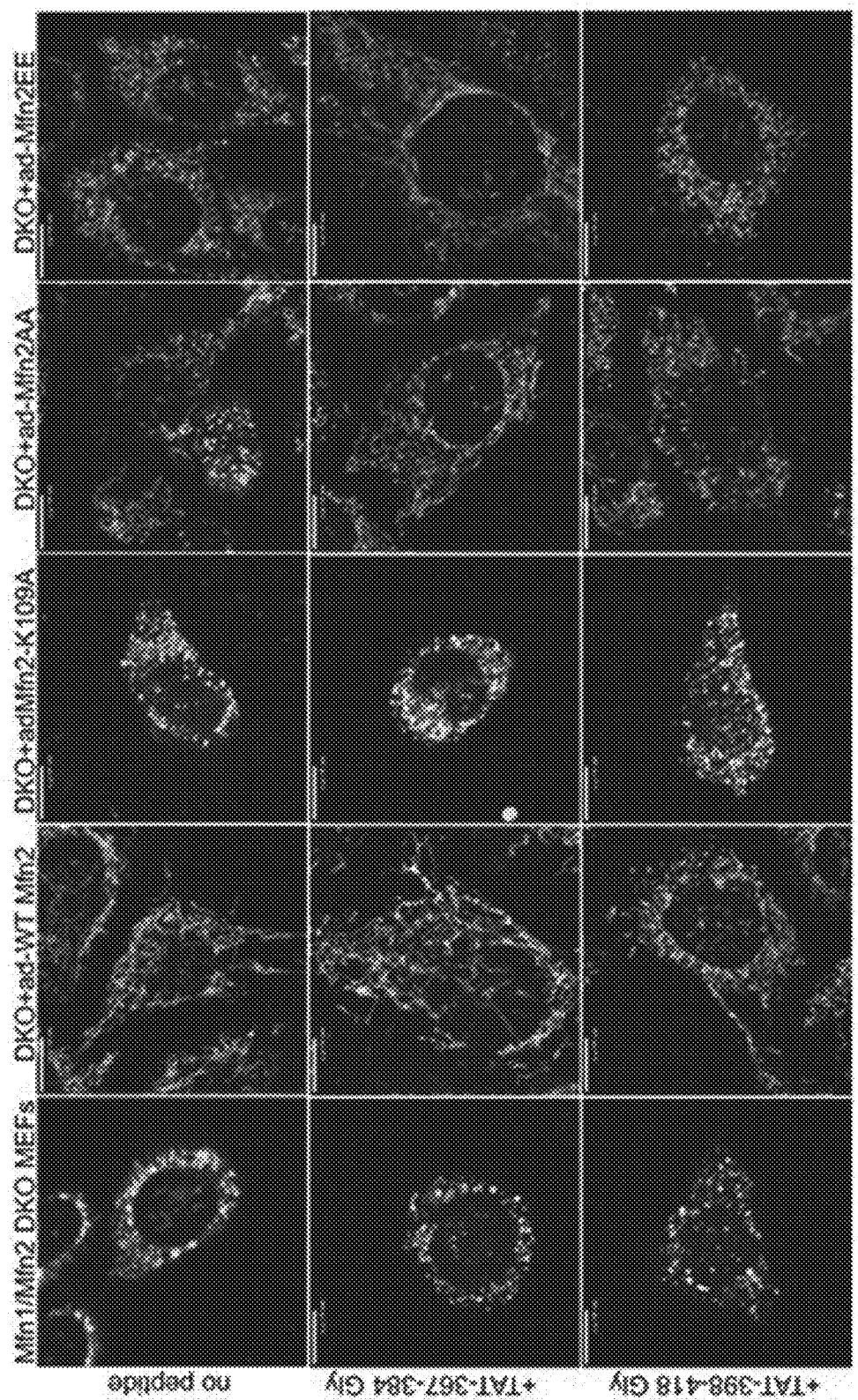
FIGS. 12A-12B show results of a study of the effects of mitochondrial fusion regulatory peptides on mitochondrial morphology.
Figure 12B:
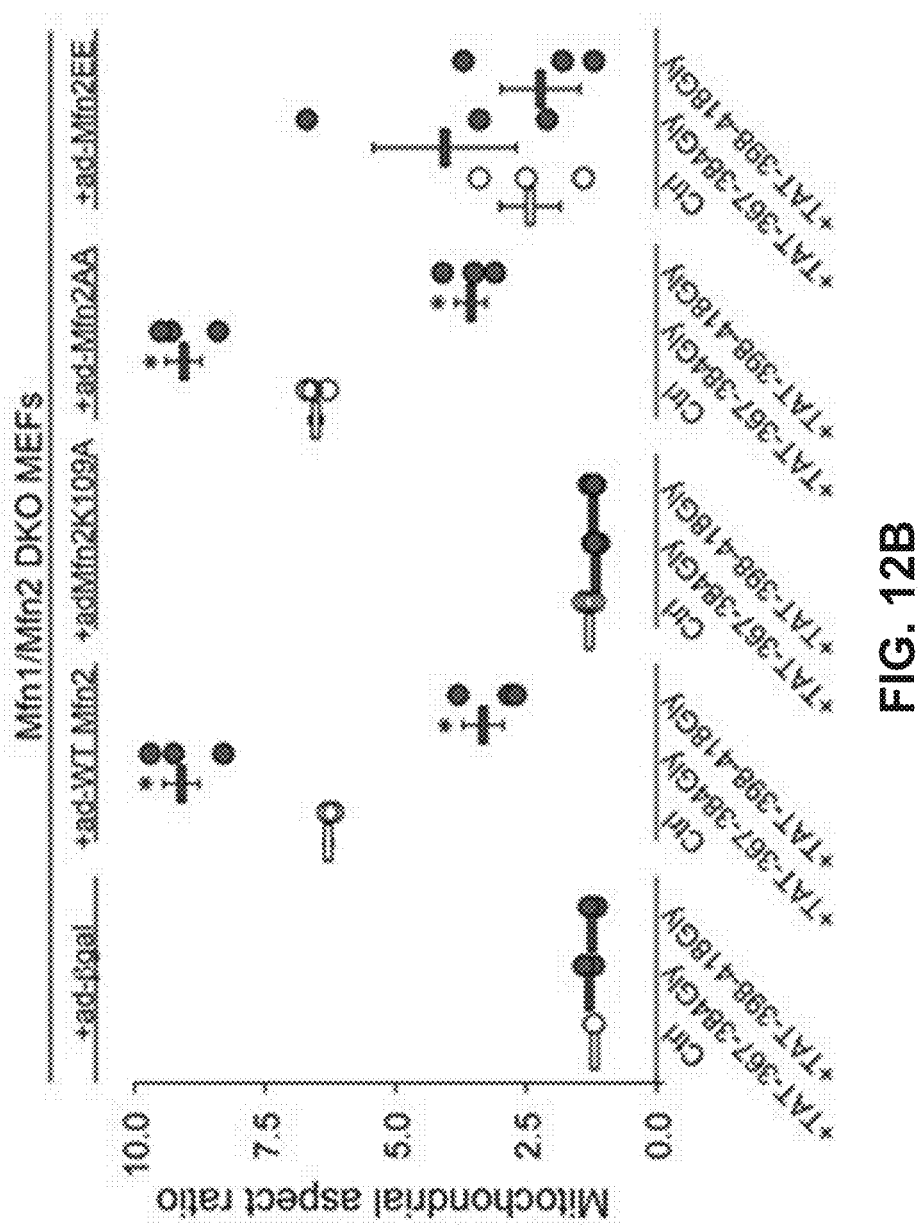

The efficacy of the minipeptides to correct mitochondrial abnormalities in Mfn null MEFs was further evaluated. In this experiment, several Mfn2 mutants having well-characterized and diverse functional profiles were introduced into Mfn null MEFs. As shown above, mitochondria of MEFs lacking Mfn1 and Mfn2 are highly fragmented. Adenoviral reintroduction of WT Mfn2 corrected dysmorphology in Mfn null MEFs and was required for TAT minipeptides to alter mitochondrial fusion in these cells (FIGS. 12A-12B). By contrast, adenoviral expression of mouse Mfn2 K109A, a GTPase defective mutant (Detmer and Chan, 2007, J Cell Biol, 176:405-414), had no effect on mitochondrial fragmentation in Mfn null MEFs. Moreover, the TAT minipeptides did not alter mitochondrial aspect ratio in MEFs expressing only Mfn2K109A, although mitochondrial clumping induced by TAT-367-384Gly suggested enhanced mitochondria-mitochondria tethering in the absence of complete organelle fusion (FIG. 12A-12B). Introduction into Mfn null MEFs of a Mfn2 mutant (Mfn2 AA) having alanine substitutions for phosphorylatable amino acids mediating mitophagic Mfn2-Parkin binding (T111 and S442 (Chen and Dorn, 2013, Science, 340:471-475; Gong et al., 2015, Science, 350:aad2459 13,14)) proved similar to WT Mfn2: Mfn2 AA normalized mitochondrial morphology in Mfn null MEFs, produced mitochondrial hyper-elongation in response to TAT-367-384Gly, and responded with mitochondrial shortening after application of TAT-398-418Gly (FIG. 12A-12B). Mitochondrial morphometry in Mfn null MEFs expressing fusion-impaired Mfn2 EE, which has glutamate substitutions to mimic phosphorylation at Mfn2 T111 and S442, was more variable (FIG. 12A-12B).

Figure 13A:
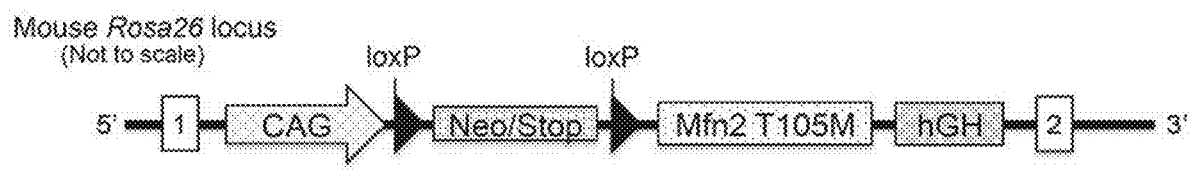
FIGS. 13A-13D illustrate generation of a Cre recombinase-inducible mutant Mfn2 system.
Figure 13B:
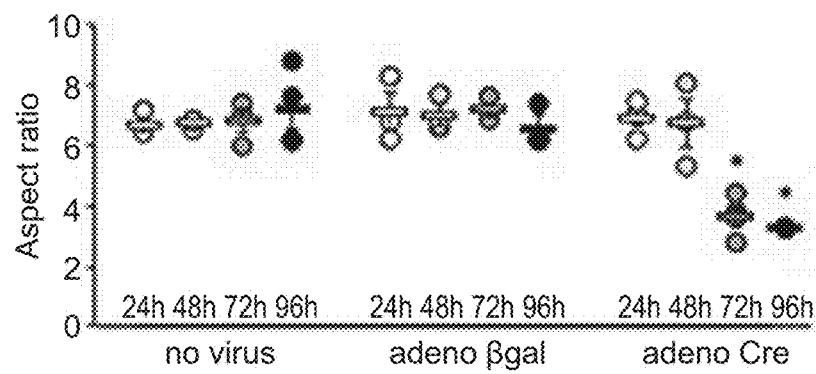
Figure 13C:
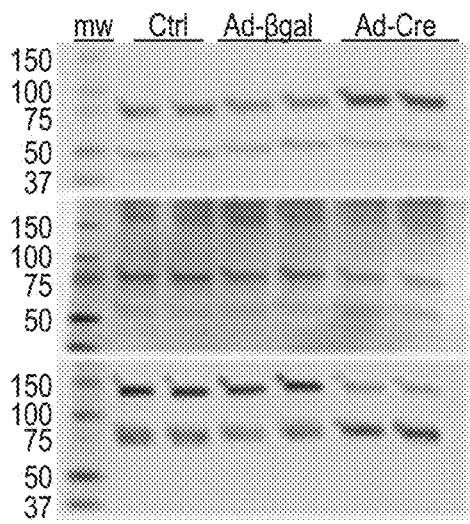
Figure 13D:
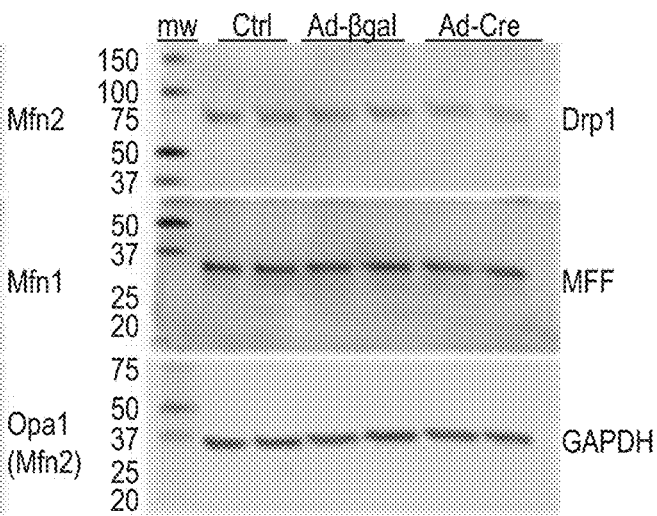

Autosomal dominant CMT2A Mfn2 mutations such as Mfn2 T105M (Calvo et al, 2009, Arch Neurol, 66:1511-1516; Detmer et al., 2008, Hum Mol Genet, 17:367-375) dominantly inhibit mitochondrial fusion and are therefore potentially resistant to therapeutic manipulation of Mfn1. Models cells harboring a Cre recombinase-inducible mutant human Mfn2 containing the T105M mutation were used (FIG. 13A) because they recapitulate fusion defects caused by compound functional null Mfn2 mutants in autosomal recessive CMT2A. A time course study of mitochondrial fragmentation after adeno-Cre mediated induction of Mfn2 T105M was performed and the results are shown in FIG. 13B. Immunoblot analysis of these cells to detect Mfn2 (FIG. 13C, left panel) and Mfn1 (FIG. 13D, right panel) shows induced expression of the Mfn2 T105M as expected.

Figure 14A:
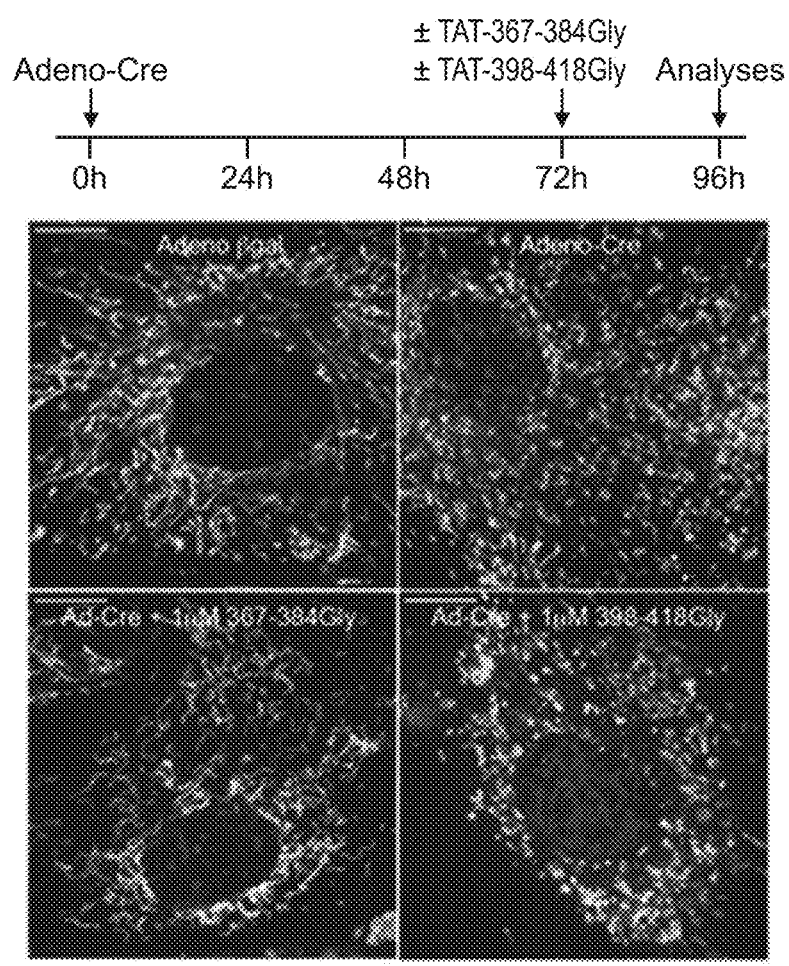
FIGS. 14A-14B show results of mitochondrial fusion regulatory peptides on mitochondrial fragmentation in Mfn2 T105M cells. Confocal micrographs of cells are shown in FIG. 14A with quantitative data for aspect ratio and depolarization provided in FIG. 14B.
Figure 14B:
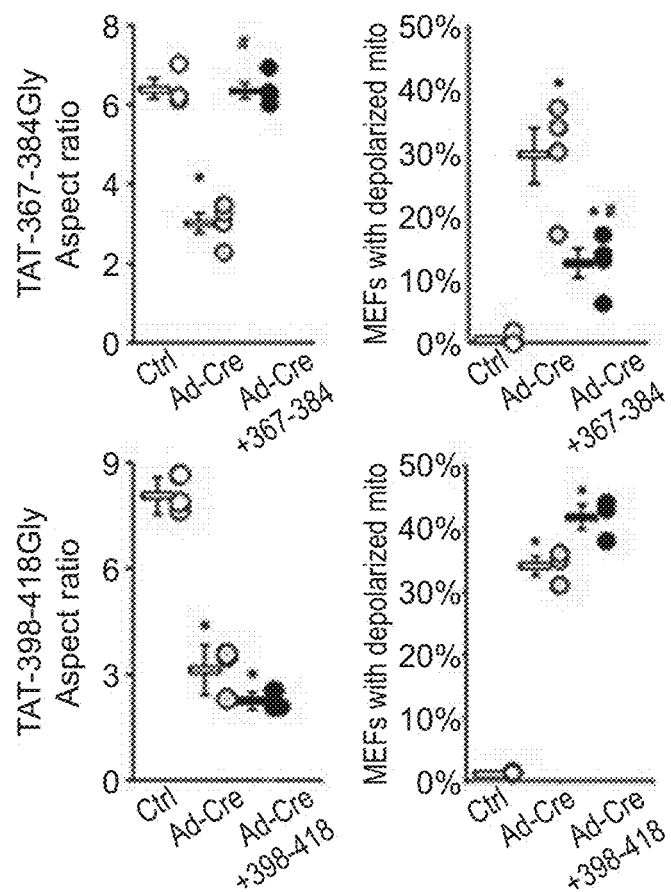

It was considered that mitochondrial dysmorphology created by genetic Mfn2 dysfunction in CMT2A might be improved by TAT-367-384Gly if endogenous normal Mfn1 or Mfn2 proteins could be compelled into their active unfolded conformations, thus overcoming dominant inhibition by GTPase Mfn2 mutants. This was tested in MEFs expressing the CMT2A-causal mutant hMfn2 T105M (Calvo et al., 2009, Arch Neurol, 66:1511-1516; Detmer et al., 2008, Hum Mol Genet, 17:367-375) as a conditional flox/stop (fl/st) transgene. Mitochondria of Mfn2 T105M fl/st MEFs fragmented and depolarized 72 hours after adenoviral-Cre application (FIGS. 13B and 14A), but application of 1 μM TAT-367-384Gly after mitochondrial abnormalities had fully manifested rapidly reversed mitochondrial fragmentation and improved mitochondrial polarization (FIG. 14B). By contrast, further suppressing mitochondrial fusion with TAT-398-418Gly aggravated mitochondrial dysmorphology and exacerbated mitochondrial depolarization induced by Mfn2 T105M (FIG. 14A-14B). Parallel adenoviral expression of WT Mfn2 at more than twice the levels of Mfn2 T105M (5-fold vs 2-fold) provoked neither mitochondrial nor cellular toxicity (data not shown). Representative micrographs are provided in FIG. 14A. Scale bars are 10 microns. Quantitative analysis of mitochondrial pathology provoked by T105M and corrected by TAT-367-384Gly is shown in FIG. 14B. N=3 or 4; *=P<0.05 vs. control, #=P<0.05 vs. Ad-Cre (ANOVA).

Example 8

Repairing Neuronal CMT2A Pathology

The efficacy of TAT-367-384Gly to correct mitochondrial pathology induced by a GTPase-defective Mfn2 mutant was examined in the CMT2A-relevant cell type, motor neurons. Motor neurons were isolated from E17 Sprague-Dawley rats and cultured as described in Wang et al., 2013, Hum Mol Genet 22:4706-4719. After 10 days in culture, neurons were infected twice, 8 hours apart, with 50 MOI of adenoviral WT-Mfn2 or K109A Mfn2 and treated with 1 µM TAT-367-384 Gly or control TAT peptide for 24 hours. Mitochondria of formalin-fixed nerons were labeled with anti-TOM20 (Santa Cruz Biotechnology). Neurons were stained with Hoechst 33342. Laser confocal imaging using a 63× oil objective was used to identify isolated mitochondria for determination of aspect ratio.

Figures 15A, 15B:
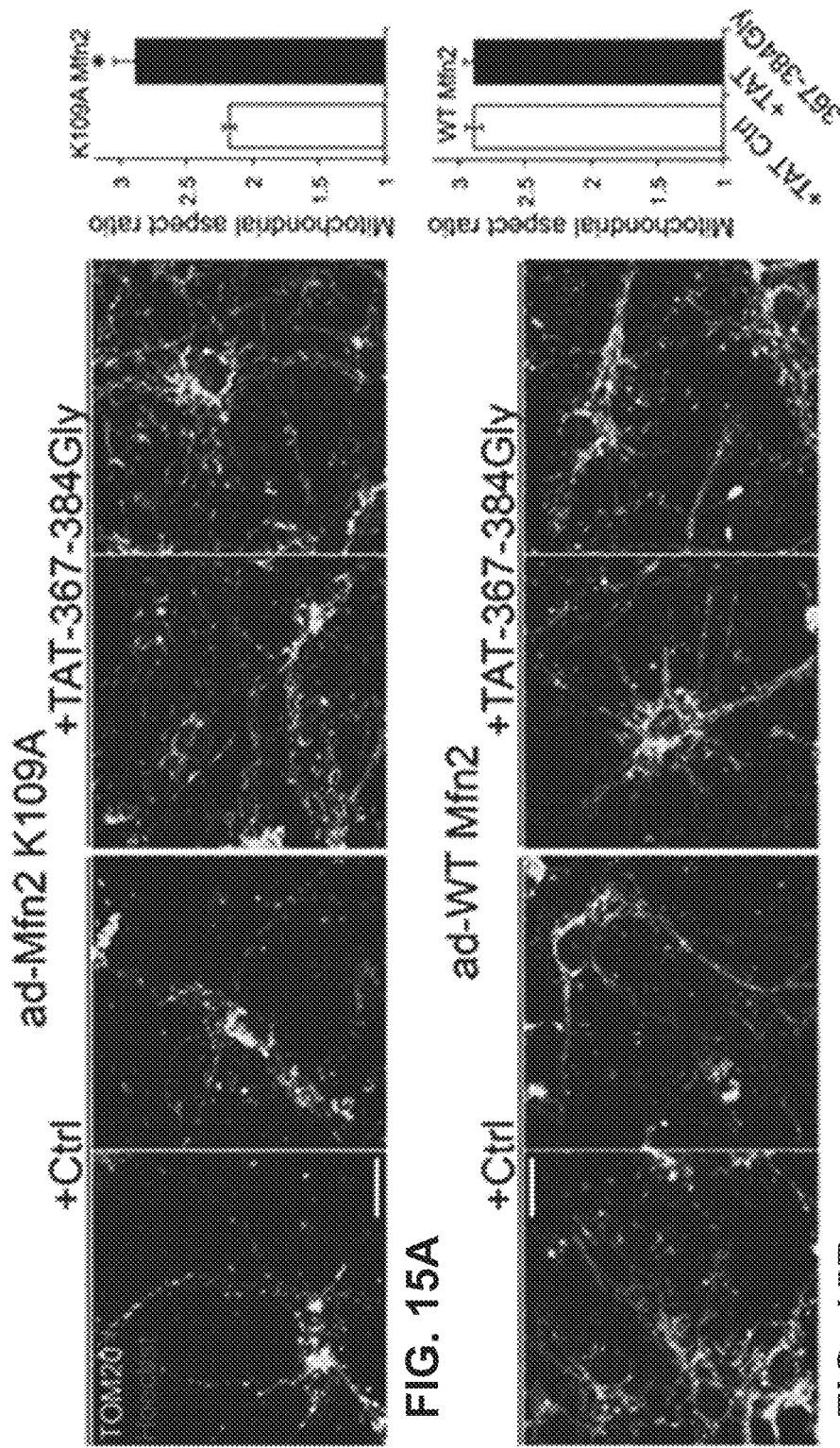
FIGS. 15A-15B show results of experiments to test the ability of mitochondrial fusion regulatory peptides to correct mitochondrial pathology using cultured neuronal cells. Results are shown for neurons infected with adeno-Mfn2K109A (FIG. 15A) or adeno-WT Mfn2 (FIG. 15B).

Representative anti-TOM20/Hoechst images of formalin-fixed cultured neurons infected with adeno-Mfn2K109A (FIG. 15A) or adeno-WT Mfn2 (FIG. 15B) and treated for 24 h with 1 µM TAT control (Ctrl) or TAT-367-384Gly minipeptide. Scale bars are 10 microns. N=20-23 per treatment group; *=P<0.05 vs Ctrl (Student's t-test).

The data (FIGS. 15A-15B) show that cultured rat motor neurons infected with adeno-Mfn2 K109A developed mitochondrial fragmentation that was fully normalized by TAT-367-384Gly. In parallel studies, adeno-WT Mfn2 produced no adverse neuronal effects.

Finally, to test the efficacy of fusion promotion by conformational manipulation in a model of a naturally-occurring human CMT2A mutation, hippocampal and cortical neurons were cultured from mouse pups carrying the conditional Mfn2 T105M fl/st expression allele.

Hippocampal and cortical neurons were prepared from individual P0-P1 mouse pups using a modification of methods described for rat neuronal culture (Mennerick et al., 1995, J Neurophysiol, 73:320-332). Mouse pups were genotyped after the fact to determine presence or absence of the MFN2*T105M transgene; neurons derived from mice lacking the transgene were designated as normal controls. The study design is illustrated in FIG. 16A with the inset showing the PCR genotyping of a Mfn2 T105M fl/st transgene (arrow) mouse litter whose pups were used for neuron harvesting and culture. Immunoblot of Mfn2 expression in T105M fl/st cortical neurons 72 h after adeno-Cre or adeno-β-gal (Ctrl) is shown in FIG. 16B with quantitative data to the right (n=4). After 10 days of culture neurons were infected with Adeno-Cre or Adeno-β gal control (50 MOI). 72 hours later 1 µM TAT-367-384Gly or vehicle was added. Live neurons were imaged as described below.

Figure 16D:
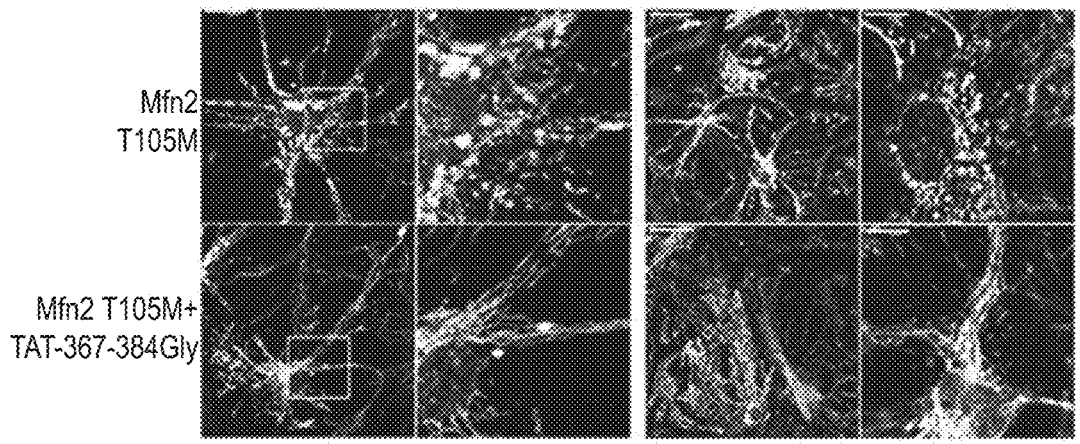

Merged live confocal images of cultured neurons without (no Cre) and with (+Cre) Mfn2 T105M induction, and in Mfn2 T105M-induced neurons 24 h after addition of 1 µM TAT-367-384Gly are shown in FIG. 16C. Scale bars are 10 microns. FIG. 16D shows Mfn2 T105M expressing neurons without (top) and with (bottom) after 24 h treatment with 1 µM TAT-367-384Gly. Ad-MitoGFP was used at low MOI for these images to enhance visualization of individual neurons. Scale bars are 40 microns in low power images and 10 microns in high power images. Quantitative data are provided in FIG. 16E; each point is result from one of 3 independently-established Mfn2 T105M neuronal cultures, each with 3 biological replicates of ~20 neurons. *=P<0.01 vs no Cre; #=P<0.01 vs T105M+Cre.

Figure 16E:
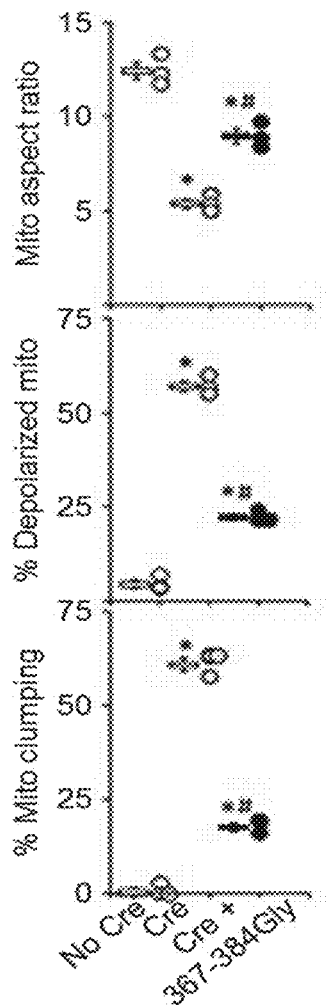

Live cell analyses demonstrated that adeno-Cre induction of Mfn2 T105M (FIG. 16B) evoked widespread neuronal mitochondrial dysmorphology with fragmentation and partial depolarization (FIGS. 16C-16E). Mitochondrial clumping in neuronal cell bodies was prevalent after Mfn2 T105M induction, consistent with interruption of GTP-dependent mitochondrial fusion in the context of sustained GTPase-independent mitochondrial tethering (FIG. 16D), or "mitochondrial aggregation" (Detmer et al., 2008, Hum Mol Genet, 17:367-375; Baloh et al., 2007, J Neurosci, 27:422-430). TAT-367-384Gly (1 µM) application for 24 hours largely reversed these abnormalities (FIGS. 16C-16E).

Example 9

Engineering Smaller Fusion-Promoting and Fusion-Inhibiting Peptides

Studies were done to determine the effects of shortening the peptides identified herein as having fusion-promoting or fusion-inhibiting activity. Peptides were engineered to reduce the length of the GoFuse1 and TetherX1 peptide sequences. Specifically, a fusion-promoting peptide comprising the GoFuse1 sequence, linker and carrier peptide, QIAEAVR<u>G</u>IMDSLHMAARGGYGRKKRRQRRR (SEQ ID NO:23), and a fusion-inhibiting peptide comprising the TetherX1 sequence, linker and carrier peptide, QDRLKFIDKQ<u>G</u>ELLAQDYKLRGGYGRKKRRQRRR (SEQ ID NO:24), were modified by shortening the peptide sequences flanking the essential mid-peptide Gly in each (G shown in bold and underlined). The sequences of the modified peptides are shown in Table 4 below.

Figure 17A:
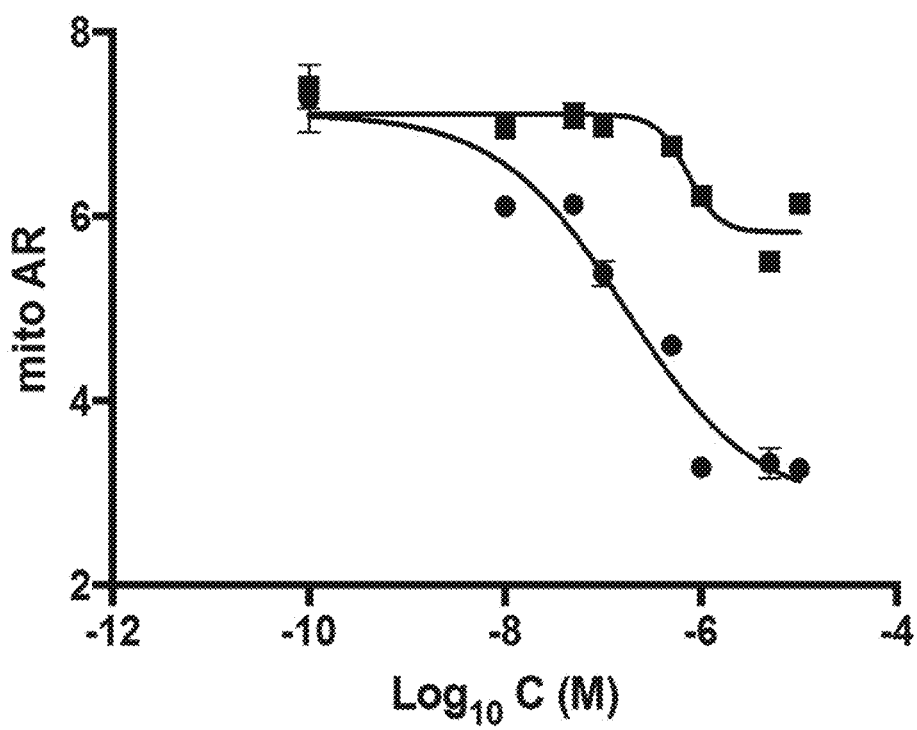
FIGS. 17A-17B show results of TetherX-1 (FIG. 17A; squares=TetherX-N; circles=TetherX-C) and GoFuse1 (FIG. 17B; squares=GoFuse-N; circles=GoFuse-C) mitochondrial fusion regulatory peptides on mitochondrial fragmentation in MEFs completely lacking Mfn1 and Mfn2.
Figure 17B:
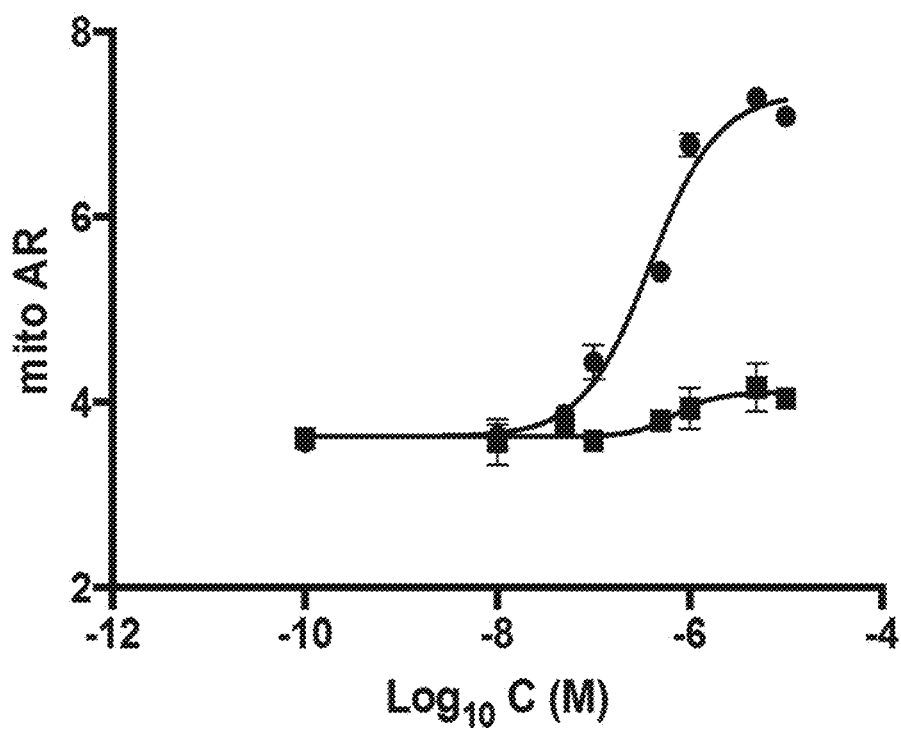

Experiments were performed with these shortened variants fused to a carrier peptide via a linker according to the methods described in Example 5 above. Wildtype MEFs were treated with varying concentrations of peptide fusion constructs described in Table 4 and mitochondrial aspect ratios determined. A dose response curve for TetherX-N and -C variants are shown in FIG. 17A (squares are data for TetherX-N and circles are for TetherX-C). The dose response curve for GoFuse-N and -C variants are shown in FIG. 17B (squares are for GoFuse-N and circles are for GoFuse-C).

The linear construct comprising the C-terminal fragment of the TetherX-1 peptide, designated TetherX-C (GELLAQDYKLR; SEQ ID NO:43), fused via a linker to a carrier peptide (SEQ ID NO:45 in Table 4), provoked mitochondrial fragmentation, reflecting inhibition of mitochondrial tethering/fusion, and had similar potency to the full-length TetherX-1 peptide (QDRLKFIDKQGEL-LAQDYKLR; SEQ ID NO:18) fused via linker to a carrier peptide (SEQ ID NO:24). The N-terminal variant, however, exhibited little activity. Likewise, the linear construct comprising the C-terminal variant of GoFuse-1, designated GoFuse-C (GIMDSLHMAAR; SEQ ID NO:48), induced mitochondrial elongation and reflected enhanced mitochondrial fusion with similar potency to the full-length GoFuse-1 peptide (QIAEAVRGIMDSLHMAAR; SEQ ID NO:14) whereas the N-terminal variant lacked fusion-promoting activity. The $EC_{50}$ value for the GoFuse-C mediated mitochondrial elongation (enhanced fusion) was 389 nM, and the $EC_{50}$ value for TetherX-C mediated mitochondrial shortening (suppressed fusion) was 171 nM.

TABLE 4

| SEQ ID NO: | Description | Sequence |
|---|---|---|
| 43 | TetherX-C | GELLAQDYKLR |
| 44 | TetherX-N | QDRLKFIDKQG |
| 24 | TetherX-1 fusion construct | QDRLKFIDKQGELLAQDYKLR-GG-YGRKKRRQRRR |
| 46 | TetherX-N fusion construct | QDRLKFIDKQG-G-YGRKKRRQRRR |
| 45 | TetherX-C fusion construct | GELLAQDYKLR-GG-YGRKKRRQRRR |
| 47 | GoFuse-N | QIAEAVRG |
| 48 | GoFuse-C | GIMDSLHMAAR |
| 23 | GoFuse1 fusion construct | QIAEAVRGIMDSLHMAAR-GG-YGRKKRRQRRR |
| 49 | GoFuse-N fusion construct | QIAEAVRG-G-YGRKKRRQRRR |
| 50 | GoFuse-C fusion construct | GIMDSLHMAAR-GG-YGRKKRRQRRR |

Example 10

Use of TetherX-1 to Reduce Stroke Size

Figure 18A:
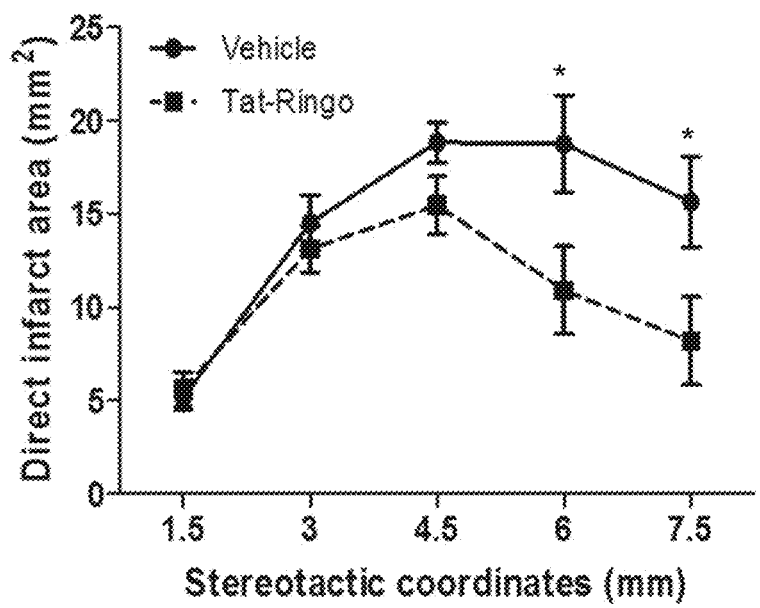
FIGS. 18A-18B show results of administering TetherX-1 to mice subjected to cerebral ischemia.
Figure 18B:
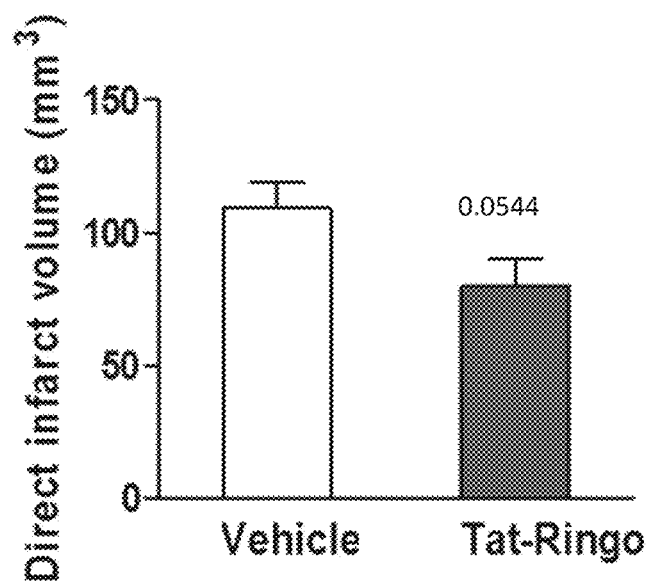
Figure 19A:
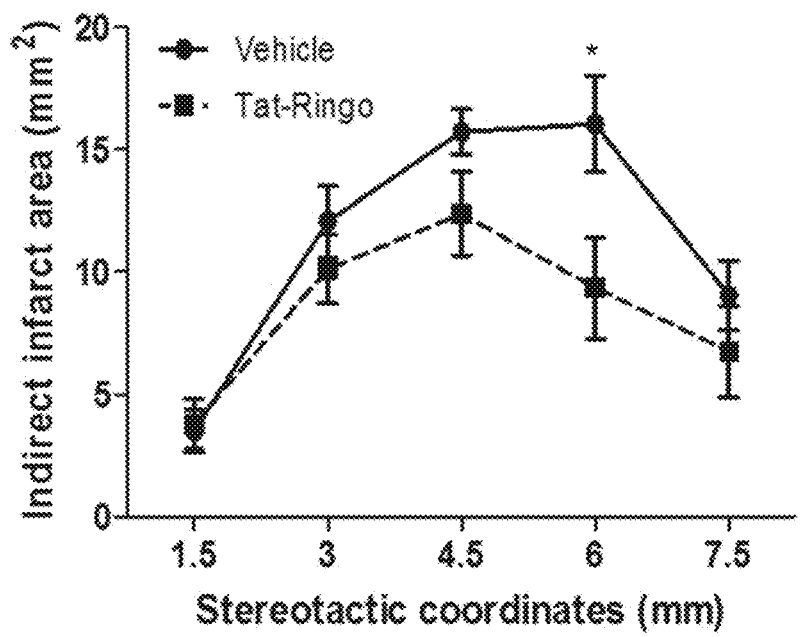
FIGS. 19A-19B show results of administering TetherX-1 to mice subjected to cerebral ischemia.
Figure 19B:
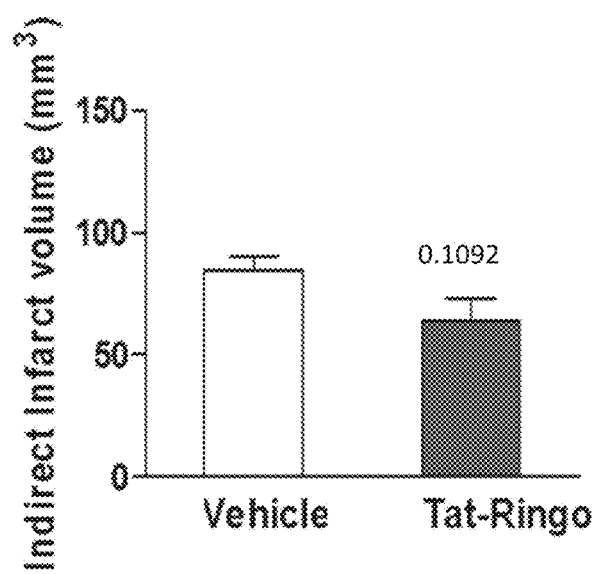
Figure 20:
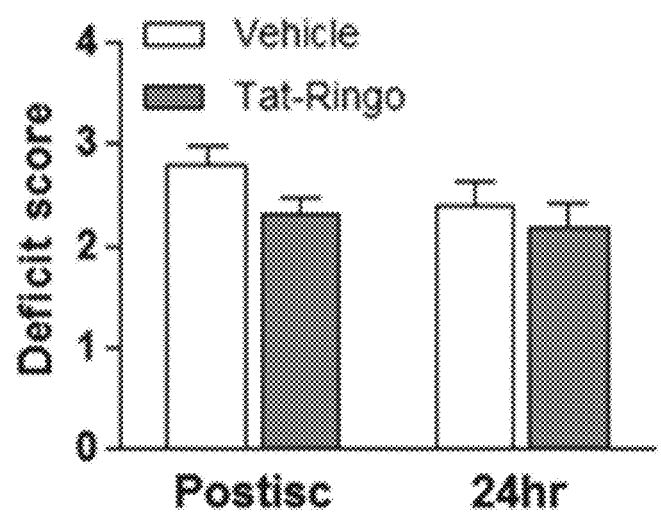
FIG. 20 shows effects on cerebral deficit of TetherX-1 administration to mice subjected to cerebral ischemia.
Figure 21:
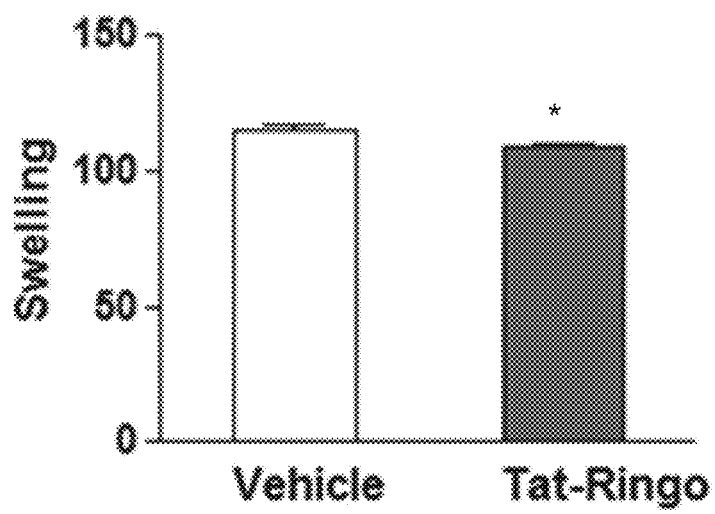
FIG. 21 shows effects on cerebral swelling of TetherX-1 administration to mice subjected to cerebral ischemia.

Studies were done to study the effects of TetherX-1 (SEQ ID NO:24) administration on cerebral tissue damage in mice in which ischemia was induced. In this blinded and placebo-controlled studies, 40 mice were subjected to temporary (40 minutes) middle cerebral artery (MCA) occlusion followed by reperfusion for 24 hours. Brains were removed and analyzed for direct and indirect infarct area and volume. As shown in FIGS. 18A-18B, administration of 3 mg/kg TetherX-1 intravenously 1 hour before ischemia and immediately prior to reperfusion resulted in a decrease in direct infarct area and volume as well as a decrease in indirect infarct area and volume (FIGS. 19A-19B) relative to administration intravenously of vehicle only (water) as a comparator (control). Moreover, TetherX-1 administration reduced cerebral deficit (FIG. 20) and cerebral swelling (FIG. 21). Measurements of cerebral blood flow, cerebral weight change, and body temperature showed no difference between animals treated with TetherX-1 and animals treated with placebo (data not shown). Accordingly, modulatory peptides according to the present disclosure which possess a function similar to that of TetherX-1, i.e., inhibit mitochondrial fusion, can be useful in reducing ischemic tissue damage in subjects.

Example 11

Alanine Scanning of the TetherX-1 and Go-Fuse Peptides

Alanine scanning mutagenesis experiments were performed in order to identify amino acids critical for the function of the TetherX-1 and Go-Fuse peptides. Alanine was individually substituted for each amino acid in the Tetherx-1 and Go-Fuse peptides and the modified peptides, linked to the TAT carrier peptide via a GG linker, were administered to cells and the effect on mitochondrial fusion measured. Results are provided in Tables 5-8 below. Table 5 lists Go-Fuse variants which maintained fusion-promoting activity (activity similar to that of SEQ ID NO:48 or 50) while Table 6 lists variant Go-Fuse peptides in which substitutions had no effect (substitution of a non-critical amino acid).

TABLE 5

| SEQ ID NO | Sequence | Substitution |
|---|---|---|
| 50 | GIMDSLHMAAR-GG-YGRKKRRQRRR | No amino acid substitution (control) |
| 53 | GIMDDLHMAAR-GG-YGRKKRRQRRR | S378D |
| 54 | GIMD(p)SLHMAAR-GG-YGRKKRRQRRR | phosphoS378 |
| 55 | GIMASLHMAAR-GG-YGRKKRRQRRR | D377A |
| 56 | GIMDSAHMAAR-GG-YGRKKRRQRRR | L379A |
| 57 | GIMDSLAMAAR-GG-YGRKKRRQRRR | H380A |

TABLE 6

| SEQ ID NO | Sequence | Substitution |
|---|---|---|
| 58 | GIADSLHMAAR-GG-YGRKKRRQRRR | M376A |
| 59 | GIMDALHMAAR-GG-YGRKKRRQRRR | S378A |
| 60 | GIMDCLHMAAR-GG-YGRKKRRQRRR | S378C |
| 61 | GIMDNLHMAAR-GG-YGRKKRRQRRR | S378N |
| 62 | GIMDGLHMAAR-GG-YGRKKRRQRRR | S378G |
| 63 | GIMDSLHAAAR-GG-YGRKKRRQRRR | M381A |

Table 7 lists TetherX-1 variants which maintained fusion-suppressing activity while Table 8 lists variant TetherX-1 peptides in which substitutions had no effect (substitution of a non-critical amino acid).

TABLE 7

| SEQ ID NO | Sequence | Substitution |
|---|---|---|
| 45 | GELLAQDYKLR-GG-YGRKKRRQRRR | No amino acid substitution (control) |
| 64 | GELLAQAYKLR-GG-YGRKKRRQRRR | D414A |
| 65 | GELLAQDYKAR-GG-YGRKKRRQRRR | L417A |

TABLE 8

| SEQ ID NO | Sequence | Substitution |
|---|---|---|
| 66 | GALLAQDYKLR-GG-YGRKKRRQRRR | E409A |
| 67 | GEALAQDYKLR-GG-YGRKKRRQRRR | L410A |
| 68 | GELAAQDYKLR-GG-YGRKKRRQRRR | L411A |
| 69 | GELLAADYKLR-GG-YGRKKRRQRRR | Q413A |
| 70 | GELLAQDAKLR-GG-YGRKKRRQRRR | Y415A |
| 71 | GELLAQDYALR-GG-YGRKKRRQRRR | K416A |
| 72 | GELLAQDYKLA-GG-YGRKKRRQRRR | R418A |

Figure 22:
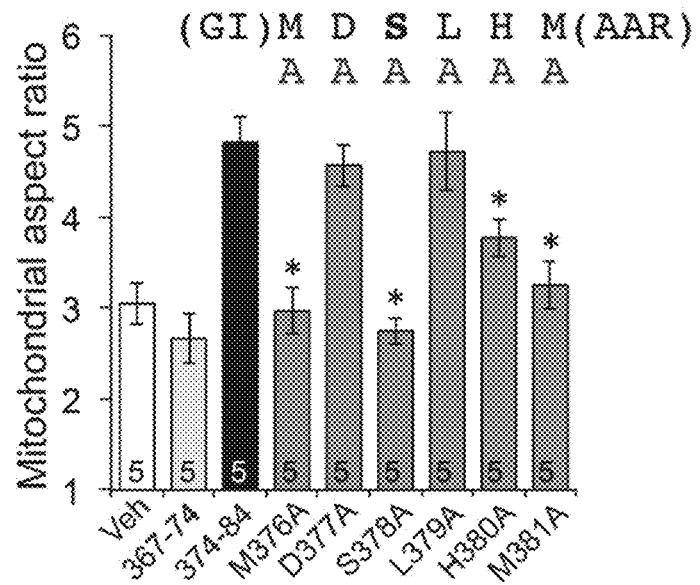
FIG. 22 shows results from alanine scanning characterization of the GoFuse-C peptide.
Figure 23:
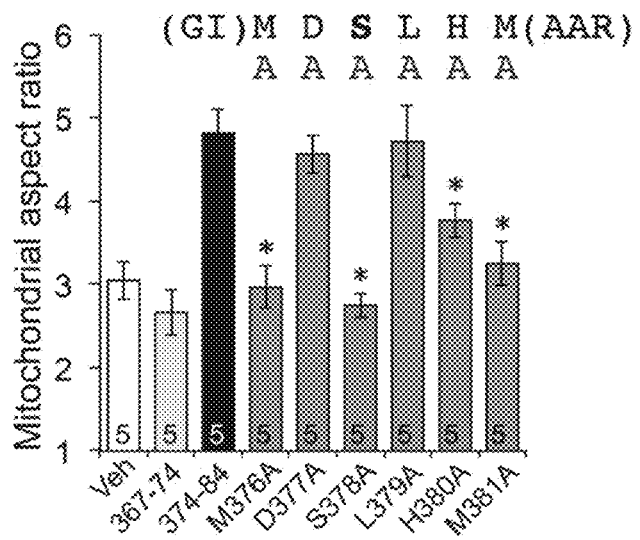
FIG. 23 shows results from alanine scanning characterization of the TetherX-C peptide.

The results from this study are shown in the bar graphs of FIGS. 22-23, where FIG. 22 shows results from alanine scanning characterization of the GoFuse-C peptide and FIG. 23 shows results from alanine scanning characterization of the TetherX-C peptide.

Figure 24:
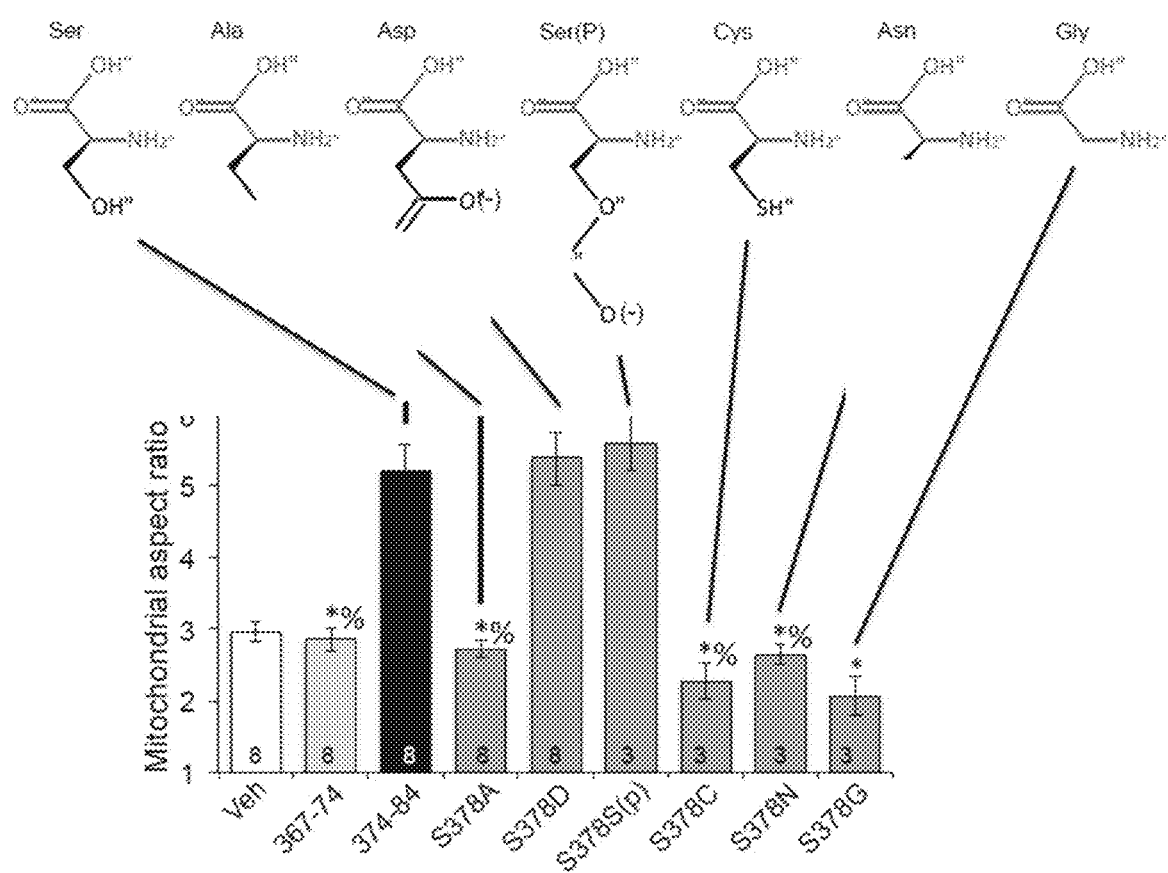
FIG. 24 is a bar graph showing that certain residues are involved in Mfn agonist activity.

FIG. 24 is a bar graph showing additional results from this study that indicate phosphorylation of Ser 378 (SEQ ID NO: 54) determines mini-peptide Mfn agonist activity. In the graph, the number in each bar indicates the number of samples tested (i.e., n), and the results show that Ser, Asp, and (p)Ser were statistically active (ANOVA) compared to the other residues.

While this disclosure has been particularly shown and described with references to example embodiments thereof, it will be understood by those skilled in the art that various changes in form and details may be made therein without departing from the scope of the invention encompassed by the appended claims.

What is claimed is:

1. A composition, comprising:
a modulatory peptide having the an amino acid sequence selected from the sequences identified as SEQ ID NO: 14, SEQ ID NO: 48, and SEQ ID NO: 75; and a pharmaceutically acceptable carrier.

2. The composition of claim 1, wherein the modulatory peptide comprises the sequence QIAEAVRGIMDSLH-MAAR (SEQ ID NO:14).

3. The composition of claim 2, wherein the modulatory peptide increases the mitochondrial aspect ratio in a cell exposed to the modulatory peptide.

4. The composition of claim 1, wherein the modulatory peptide is linked to a carrier moiety.

5. The composition of claim 4, wherein the carrier moiety is a carrier peptide and wherein the carrier peptide is a Tat peptide comprising the sequence of SEQ ID NO:22.

6. The composition of claim 5, wherein the carrier peptide is linked to the modulatory peptide by a peptide bond to form a linear peptide.

7. The composition of claim 5, wherein the composition further comprises a linker peptide, wherein the linker peptide is positioned between the modulatory peptide and the carrier peptide.

8. The composition of claim 7, wherein the peptide linker comprises 2, 3, 4 or 5 amino acids.

9. The composition according to claim 8, wherein the peptide linker comprises GG, GGG or GGGG (SEQ ID NO:34).

10. The composition of claim 5, wherein the carrier peptide is C-terminal to the modulatory peptide or wherein the carrier peptide is N-terminal to the modulatory peptide.

11. The composition of claim 4, wherein the carrier moiety is a carrier peptide and wherein each of the modulatory peptide and the carrier peptide further comprises a terminal cysteine residue on its N-terminus or its C-terminus and wherein the terminal cysteine on the modulatory peptide is linked to the terminal cysteine on the carrier peptide by a disulfide bond.

12. A modulatory peptide consisting of a sequence selected from the sequences identified as SEQ ID NO: 14, SEQ ID NO: 48, and SEQ ID NO: 75.

* * * * *

SEQUENCE LISTING

<160> NUMBER OF SEQ ID NOS: 94

<210> SEQ ID NO 1
<211> LENGTH: 741
<212> TYPE: PRT
<213> ORGANISM: Homo sapiens

<400> SEQUENCE: 1

Met Ala Glu Pro Val Ser Pro Leu Lys His Phe Val Leu Ala Lys Lys
1               5                   10                  15

Ala Ile Thr Ala Ile Phe Asp Gln Leu Leu Glu Phe Val Thr Glu Gly
            20                  25                  30

Ser His Phe Val Glu Ala Thr Tyr Lys Asn Pro Glu Leu Asp Arg Ile
        35                  40                  45

Ala Thr Glu Asp Asp Leu Val Glu Met Gln Gly Tyr Lys Asp Lys Leu
    50                  55                  60

Ser Ile Ile Gly Glu Val Leu Ser Arg Arg His Met Lys Val Ala Phe
65                  70                  75                  80

Phe Gly Arg Thr Ser Ser Gly Lys Ser Ser Val Ile Asn Ala Met Leu
                85                  90                  95

Trp Asp Lys Val Leu Pro Ser Gly Ile Gly His Ile Thr Asn Cys Phe
            100                 105                 110

Leu Ser Val Glu Gly Thr Asp Gly Asp Lys Ala Tyr Leu Met Thr Glu
        115                 120                 125

Gly Ser Asp Glu Lys Lys Ser Val Lys Thr Val Asn Gln Leu Ala His
    130                 135                 140

Ala Leu His Met Asp Lys Asp Leu Lys Ala Gly Cys Leu Val Arg Val
145                 150                 155                 160

Phe Trp Pro Lys Ala Lys Cys Ala Leu Leu Arg Asp Asp Leu Val Leu
                165                 170                 175

Val Asp Ser Pro Gly Thr Asp Val Thr Thr Glu Leu Asp Ser Trp Ile
            180                 185                 190

Asp Lys Phe Cys Leu Asp Ala Asp Val Phe Val Leu Val Ala Asn Ser
        195                 200                 205

Glu Ser Thr Leu Met Asn Thr Glu Lys His Phe Phe His Lys Val Asn
    210                 215                 220

Glu Arg Leu Ser Lys Pro Asn Ile Phe Ile Leu Asn Asn Arg Trp Asp
225                 230                 235                 240

Ala Ser Ala Ser Glu Pro Glu Tyr Met Glu Asp Val Arg Arg Gln His

```
                    245                 250                 255
Met Glu Arg Cys Leu His Phe Leu Val Glu Glu Leu Lys Val Val Asn
                260                 265                 270

Ala Leu Glu Ala Gln Asn Arg Ile Phe Phe Val Ser Ala Lys Glu Val
            275                 280                 285

Leu Ser Ala Arg Lys Gln Lys Ala Gln Gly Met Pro Glu Ser Gly Val
        290                 295                 300

Ala Leu Ala Glu Gly Phe His Ala Arg Leu Gln Glu Phe Gln Asn Phe
305                 310                 315                 320

Glu Gln Ile Phe Glu Glu Cys Ile Ser Gln Ser Ala Val Lys Thr Lys
                325                 330                 335

Phe Glu Gln His Thr Ile Arg Ala Lys Gln Ile Leu Ala Thr Val Lys
                340                 345                 350

Asn Ile Met Asp Ser Val Asn Leu Ala Ala Glu Asp Lys Arg His Tyr
                355                 360                 365

Ser Val Glu Glu Arg Glu Asp Gln Ile Asp Arg Leu Asp Phe Ile Arg
        370                 375                 380

Asn Gln Met Asn Leu Leu Thr Leu Asp Val Lys Lys Ile Lys Glu
385                 390                 395                 400

Val Thr Glu Glu Val Ala Asn Lys Val Ser Cys Ala Met Thr Asp Glu
                405                 410                 415

Ile Cys Arg Leu Ser Val Leu Val Asp Glu Phe Cys Ser Glu Phe His
                420                 425                 430

Pro Asn Pro Asp Val Leu Lys Ile Tyr Lys Ser Glu Leu Asn Lys His
            435                 440                 445

Ile Glu Asp Gly Met Gly Arg Asn Leu Ala Asp Arg Cys Thr Asp Glu
        450                 455                 460

Val Asn Ala Leu Val Leu Gln Thr Gln Gln Ile Ile Glu Asn Leu
465                 470                 475                 480

Lys Pro Leu Leu Pro Ala Gly Ile Gln Asp Lys Leu His Thr Leu Ile
                485                 490                 495

Pro Cys Lys Lys Phe Asp Leu Ser Tyr Asn Leu Asn Tyr His Lys Leu
                500                 505                 510

Cys Ser Asp Phe Gln Glu Asp Ile Val Phe Arg Phe Ser Leu Gly Trp
            515                 520                 525

Ser Ser Leu Val His Arg Phe Leu Gly Pro Arg Asn Ala Gln Arg Val
        530                 535                 540

Leu Leu Gly Leu Ser Glu Pro Ile Phe Gln Leu Pro Arg Ser Leu Ala
545                 550                 555                 560

Ser Thr Pro Thr Ala Pro Thr Thr Pro Ala Thr Pro Asp Asn Ala Ser
                565                 570                 575

Gln Glu Glu Leu Met Ile Thr Leu Val Thr Gly Leu Ala Ser Val Thr
                580                 585                 590

Ser Arg Thr Ser Met Gly Ile Ile Ile Val Gly Gly Val Ile Trp Lys
            595                 600                 605

Thr Ile Gly Trp Lys Leu Leu Ser Val Ser Leu Thr Met Tyr Gly Ala
        610                 615                 620

Leu Tyr Leu Tyr Glu Arg Leu Ser Trp Thr Thr His Ala Lys Glu Arg
625                 630                 635                 640

Ala Phe Lys Gln Gln Phe Val Asn Tyr Ala Thr Glu Lys Leu Arg Met
                645                 650                 655

Ile Val Ser Ser Thr Ser Ala Asn Cys Ser His Gln Val Lys Gln Gln
                660                 665                 670
```

-continued

```
Ile Ala Thr Thr Phe Ala Arg Leu Cys Gln Gln Val Asp Ile Thr Gln
            675                 680                 685
Lys Gln Leu Glu Glu Ile Ala Arg Leu Pro Lys Glu Ile Asp Gln
690                 695                 700
Leu Glu Lys Ile Gln Asn Asn Ser Lys Leu Leu Arg Asn Lys Ala Val
705                 710                 715                 720
Gln Leu Glu Asn Glu Leu Glu Asn Phe Thr Lys Gln Phe Leu Pro Ser
            725                 730                 735
Ser Asn Glu Glu Ser
            740

<210> SEQ ID NO 2
<211> LENGTH: 757
<212> TYPE: PRT
<213> ORGANISM: Homo sapiens

<400> SEQUENCE: 2

Met Ser Leu Leu Phe Ser Arg Cys Asn Ser Ile Val Thr Val Lys Lys
1               5                   10                  15
Asn Lys Arg His Met Ala Glu Val Asn Ala Ser Pro Leu Lys His Phe
            20                  25                  30
Val Thr Ala Lys Lys Lys Ile Asn Gly Ile Phe Glu Gln Leu Gly Ala
        35                  40                  45
Tyr Ile Gln Glu Ser Ala Thr Phe Leu Glu Asp Thr Tyr Arg Asn Ala
    50                  55                  60
Glu Leu Asp Pro Val Thr Thr Glu Glu Gln Val Leu Asp Val Lys Gly
65                  70                  75                  80
Tyr Leu Ser Lys Val Arg Gly Ile Ser Glu Val Leu Ala Arg His
                85                  90                  95
Met Lys Val Ala Phe Phe Gly Arg Thr Ser Asn Gly Lys Ser Thr Val
            100                 105                 110
Ile Asn Ala Met Leu Trp Asp Lys Val Leu Pro Ser Gly Ile Gly His
            115                 120                 125
Thr Thr Asn Cys Phe Leu Arg Val Glu Gly Thr Asp Gly His Glu Ala
130                 135                 140
Phe Leu Leu Thr Glu Gly Ser Glu Glu Lys Arg Ser Ala Lys Thr Val
145                 150                 155                 160
Asn Gln Leu Ala His Ala Leu His Gln Asp Lys Gln Leu His Ala Gly
                165                 170                 175
Ser Leu Val Ser Val Met Trp Pro Asn Ser Lys Cys Pro Leu Leu Lys
            180                 185                 190
Asp Asp Leu Val Leu Met Asp Ser Pro Gly Ile Asp Val Thr Thr Glu
            195                 200                 205
Leu Asp Ser Trp Ile Asp Lys Phe Cys Leu Asp Ala Asp Val Phe Val
    210                 215                 220
Leu Val Ala Asn Ser Glu Ser Thr Leu Met Gln Thr Glu Lys His Phe
225                 230                 235                 240
Phe His Lys Val Ser Glu Arg Leu Ser Arg Pro Asn Ile Phe Ile Leu
                245                 250                 255
Asn Asn Arg Trp Asp Ala Ser Ala Ser Glu Pro Glu Tyr Met Glu Glu
            260                 265                 270
Val Arg Arg Gln His Met Glu Arg Cys Thr Ser Phe Leu Val Asp Glu
            275                 280                 285
Leu Gly Val Val Asp Arg Ser Gln Ala Gly Asp Arg Ile Phe Phe Val
```

-continued

```
                290                 295                 300
Ser Ala Lys Glu Val Leu Asn Ala Arg Ile Gln Lys Ala Gln Gly Met
305                 310                 315                 320

Pro Glu Gly Gly Ala Leu Ala Glu Gly Phe Gln Val Arg Met Phe
                325                 330                 335

Glu Phe Gln Asn Phe Glu Arg Arg Phe Glu Glu Cys Ile Ser Gln Ser
                340                 345                 350

Ala Val Lys Thr Lys Phe Glu Gln His Thr Val Arg Ala Lys Gln Ile
                355                 360                 365

Ala Glu Ala Val Arg Leu Ile Met Asp Ser Leu His Met Ala Ala Arg
            370                 375                 380

Glu Gln Gln Val Tyr Cys Glu Glu Met Arg Glu Glu Arg Gln Asp Arg
385                 390                 395                 400

Leu Lys Phe Ile Asp Lys Gln Leu Glu Leu Leu Ala Gln Asp Tyr Lys
                405                 410                 415

Leu Arg Ile Lys Gln Ile Thr Glu Glu Val Glu Arg Gln Val Ser Thr
                420                 425                 430

Ala Met Ala Glu Glu Ile Arg Arg Leu Ser Val Leu Val Asp Asp Tyr
            435                 440                 445

Gln Met Asp Phe His Pro Ser Pro Val Val Leu Lys Val Tyr Lys Asn
            450                 455                 460

Glu Leu His Arg His Ile Glu Glu Gly Leu Gly Arg Asn Met Ser Asp
465                 470                 475                 480

Arg Cys Ser Thr Ala Ile Thr Asn Ser Leu Gln Thr Met Gln Gln Asp
                485                 490                 495

Met Ile Asp Gly Leu Lys Pro Leu Leu Pro Val Ser Val Arg Ser Gln
                500                 505                 510

Ile Asp Met Leu Val Pro Arg Gln Cys Phe Ser Leu Asn Tyr Asp Leu
            515                 520                 525

Asn Cys Asp Lys Leu Cys Ala Asp Phe Gln Glu Asp Ile Glu Phe His
530                 535                 540

Phe Ser Leu Gly Trp Thr Met Leu Val Asn Arg Phe Leu Gly Pro Lys
545                 550                 555                 560

Asn Ser Arg Arg Ala Leu Met Gly Tyr Asn Asp Gln Val Gln Arg Pro
                565                 570                 575

Ile Pro Leu Thr Pro Ala Asn Pro Ser Met Pro Pro Leu Pro Gln Gly
            580                 585                 590

Ser Leu Thr Gln Glu Glu Phe Met Val Ser Met Val Thr Gly Leu Ala
            595                 600                 605

Ser Leu Thr Ser Arg Thr Ser Met Gly Ile Leu Val Val Gly Gly Val
            610                 615                 620

Val Trp Lys Ala Val Gly Trp Arg Leu Ile Ala Leu Ser Phe Gly Leu
625                 630                 635                 640

Tyr Gly Leu Leu Tyr Val Tyr Glu Arg Leu Thr Trp Thr Thr Lys Ala
                645                 650                 655

Lys Glu Arg Ala Phe Lys Arg Gln Phe Val Glu His Ala Ser Glu Lys
                660                 665                 670

Leu Gln Leu Val Ile Ser Tyr Thr Gly Ser Asn Cys Ser His Gln Val
                675                 680                 685

Gln Gln Glu Leu Ser Gly Thr Phe Ala His Leu Cys Gln Gln Val Asp
            690                 695                 700

Val Thr Arg Glu Asn Leu Glu Gln Glu Ile Ala Ala Met Asn Lys Lys
705                 710                 715                 720
```

```
Ile Glu Val Leu Asp Ser Leu Gln Ser Lys Ala Lys Leu Leu Arg Asn
                725                 730                 735

Lys Ala Gly Trp Leu Asp Ser Glu Leu Asn Met Phe Thr His Gln Tyr
            740                 745                 750

Leu Gln Pro Ser Arg
        755

<210> SEQ ID NO 3
<211> LENGTH: 695
<212> TYPE: PRT
<213> ORGANISM: Nostoc punctiforme

<400> SEQUENCE: 3

Met Val Asn Gln Val Ala Thr Asp Arg Phe Ile Gln Asp Leu Glu Arg
1               5                   10                  15

Val Ala Gln Val Arg Ser Glu Met Ser Val Cys Leu Asn Lys Leu Ala
            20                  25                  30

Glu Thr Ile Asn Lys Ala Glu Leu Ala Gly Asp Ser Ser Gly Lys
        35                  40                  45

Leu Ser Leu Glu Arg Asp Ile Glu Asp Ile Thr Ile Ala Ser Lys Asn
50                  55                  60

Leu Gln Gln Gly Val Phe Arg Leu Val Leu Gly Asp Met Lys Arg
65                  70                  75                  80

Gly Lys Ser Thr Phe Leu Asn Ala Leu Ile Gly Glu Asn Leu Leu Pro
                85                  90                  95

Ser Asp Val Asn Pro Cys Thr Ala Val Leu Thr Val Leu Arg Tyr Gly
            100                 105                 110

Pro Glu Lys Lys Val Thr Ile His Phe Asn Asp Gly Lys Ser Pro Gln
        115                 120                 125

Gln Leu Asp Phe Gln Asn Phe Lys Tyr Lys Tyr Thr Ile Asp Pro Ala
130                 135                 140

Glu Ala Lys Lys Leu Glu Gln Glu Lys Gln Ala Phe Pro Asp Val
145                 150                 155                 160

Asp Tyr Ala Val Val Glu Tyr Pro Leu Thr Leu Leu Gln Lys Gly Ile
                165                 170                 175

Glu Ile Val Asp Ser Pro Gly Leu Asn Asp Thr Glu Ala Arg Asn Glu
            180                 185                 190

Leu Ser Leu Gly Tyr Val Asn Asn Cys His Ala Ile Leu Phe Val Met
        195                 200                 205

Arg Ala Ser Gln Pro Cys Thr Leu Gly Glu Arg Tyr Leu Glu Asn
210                 215                 220

Tyr Ile Lys Gly Arg Gly Leu Thr Val Phe Phe Leu Val Asn Ala Trp
225                 230                 235                 240

Asp Gln Val Arg Glu Ser Leu Ile Asp Pro Asp Val Glu Glu Leu
                245                 250                 255

Gln Ala Ser Glu Asn Arg Leu Arg Gln Val Phe Asn Ala Asn Leu Ala
            260                 265                 270

Glu Tyr Cys Thr Val Glu Gly Gln Asn Ile Tyr Asp Glu Arg Val Phe
        275                 280                 285

Glu Leu Ser Ser Ile Gln Ala Leu Arg Arg Leu Lys Asn Pro Gln
290                 295                 300

Ala Asp Leu Asp Gly Thr Gly Phe Pro Lys Phe Met Asp Ser Leu Asn
305                 310                 315                 320

Thr Phe Leu Thr Arg Glu Arg Ala Ile Ala Glu Leu Arg Gln Val Arg
```

```
                    325                 330                 335
Thr Leu Ala Arg Leu Ala Cys Asn His Thr Arg Glu Ala Val Ala Arg
                340                 345                 350
Arg Ile Pro Leu Leu Glu Gln Asp Val Asn Glu Leu Lys Lys Arg Ile
            355                 360                 365
Asp Ser Val Glu Pro Glu Phe Asn Lys Leu Thr Gly Ile Arg Asp Glu
        370                 375                 380
Phe Gln Lys Glu Ile Ile Asn Thr Arg Asp Thr Gln Ala Arg Thr Ile
385                 390                 395                 400
Ser Glu Ser Phe Arg Ser Tyr Val Leu Asn Leu Gly Asn Thr Phe Glu
                405                 410                 415
Asn Asp Phe Leu Arg Tyr Gln Pro Glu Leu Asn Leu Phe Asp Phe Leu
                420                 425                 430
Ser Ser Gly Lys Arg Glu Ala Phe Asn Ala Ala Leu Gln Lys Ala Phe
            435                 440                 445
Glu Gln Tyr Ile Thr Asp Lys Ser Ala Ala Trp Thr Leu Thr Ala Glu
        450                 455                 460
Lys Asp Ile Asn Ala Ala Phe Lys Glu Leu Ser Arg Ser Ala Ser Gln
465                 470                 475                 480
Tyr Gly Ala Ser Tyr Asn Gln Ile Thr Asp Gln Ile Thr Glu Lys Leu
                485                 490                 495
Thr Gly Lys Asp Val Lys Val His Thr Thr Thr Ala Glu Glu Asp
            500                 505                 510
Asn Ser Pro Gly Trp Ala Lys Trp Ala Met Gly Leu Leu Ser Leu Ser
            515                 520                 525
Lys Gly Asn Leu Ala Gly Phe Ala Leu Ala Gly Ala Gly Phe Asp Trp
        530                 535                 540
Lys Asn Ile Leu Leu Asn Tyr Phe Thr Val Ile Gly Ile Gly Gly Ile
545                 550                 555                 560
Ile Thr Ala Val Thr Gly Ile Leu Leu Gly Pro Ile Gly Phe Ala Leu
                565                 570                 575
Leu Gly Leu Gly Val Gly Phe Leu Gln Ala Asp Gln Ala Arg Arg Glu
            580                 585                 590
Leu Val Lys Thr Ala Lys Lys Glu Leu Val Lys His Leu Pro Gln Val
        595                 600                 605
Ala His Glu Gln Ser Gln Val Val Tyr Asn Ala Val Lys Glu Cys Phe
        610                 615                 620
Asp Ser Tyr Glu Arg Glu Val Ser Lys Arg Ile Asn Asp Asp Ile Val
625                 630                 635                 640
Ser Arg Lys Ser Glu Leu Asp Asn Leu Val Lys Gln Lys Gln Thr Arg
                645                 650                 655
Glu Ile Asn Arg Glu Ser Glu Phe Asn Arg Leu Lys Asn Leu Gln Glu
            660                 665                 670
Asp Val Ile Ala Gln Leu Gln Lys Ile Glu Ala Ala Tyr Ser Asn Leu
        675                 680                 685
Leu Ala Tyr Tyr Ser His His
690                 695

<210> SEQ ID NO 4
<211> LENGTH: 18
<212> TYPE: PRT
<213> ORGANISM: Artificial
<220> FEATURE:
<223> OTHER INFORMATION: Synthetic
<220> FEATURE:
```

```
<221> NAME/KEY: misc_feature
<222> LOCATION: (1)..(2)
<223> OTHER INFORMATION: Xaa can be any naturally occurring amino acid
<220> FEATURE:
<221> NAME/KEY: misc_feature
<222> LOCATION: (4)..(5)
<223> OTHER INFORMATION: Xaa can be any naturally occurring amino acid
<220> FEATURE:
<221> NAME/KEY: misc_feature
<222> LOCATION: (7)..(7)
<223> OTHER INFORMATION: Xaa can be any naturally occurring amino acid
<220> FEATURE:
<221> NAME/KEY: misc_feature
<222> LOCATION: (9)..(9)
<223> OTHER INFORMATION: Xaa can be any naturally occurring amino acid
<220> FEATURE:
<221> NAME/KEY: misc_feature
<222> LOCATION: (11)..(12)
<223> OTHER INFORMATION: Xaa can be any naturally occurring amino acid
<220> FEATURE:
<221> NAME/KEY: misc_feature
<222> LOCATION: (14)..(16)
<223> OTHER INFORMATION: Xaa can be any naturally occurring amino acid
<220> FEATURE:
<221> NAME/KEY: misc_feature
<222> LOCATION: (18)..(18)
<223> OTHER INFORMATION: Xaa can be any naturally occurring amino acid

<400> SEQUENCE: 4

Xaa Xaa Ala Xaa Xaa Val Xaa Gly Xaa Met Xaa Xaa Leu Xaa Xaa Xaa
1               5                   10                  15

Ala Xaa

<210> SEQ ID NO 5
<211> LENGTH: 18
<212> TYPE: PRT
<213> ORGANISM: Artificial
<220> FEATURE:
<223> OTHER INFORMATION: Synthetic
<220> FEATURE:
<221> NAME/KEY: misc_feature
<222> LOCATION: (1)..(2)
<223> OTHER INFORMATION: Xaa can be any naturally occurring amino acid
<220> FEATURE:
<221> NAME/KEY: misc_feature
<222> LOCATION: (4)..(5)
<223> OTHER INFORMATION: Xaa can be any naturally occurring amino acid
<220> FEATURE:
<221> NAME/KEY: misc_feature
<222> LOCATION: (7)..(7)
<223> OTHER INFORMATION: Xaa can be any naturally occurring amino acid
<220> FEATURE:
<221> NAME/KEY: misc_feature
<222> LOCATION: (11)..(12)
<223> OTHER INFORMATION: Xaa can be any naturally occurring amino acid
<220> FEATURE:
<221> NAME/KEY: misc_feature
<222> LOCATION: (14)..(16)
<223> OTHER INFORMATION: Xaa can be any naturally occurring amino acid
<220> FEATURE:
<221> NAME/KEY: misc_feature
<222> LOCATION: (18)..(18)
<223> OTHER INFORMATION: Xaa can be any naturally occurring amino acid

<400> SEQUENCE: 5

Xaa Xaa Ala Xaa Xaa Val Xaa Gly Ile Met Xaa Xaa Leu Xaa Xaa Xaa
1               5                   10                  15

Ala Xaa

<210> SEQ ID NO 6
<211> LENGTH: 17
<212> TYPE: PRT
<213> ORGANISM: Artificial
```

```
<220> FEATURE:
<223> OTHER INFORMATION: Synthetic
<220> FEATURE:
<221> NAME/KEY: misc_feature
<222> LOCATION: (1)..(2)
<223> OTHER INFORMATION: Xaa can be any naturally occurring amino acid
<220> FEATURE:
<221> NAME/KEY: misc_feature
<222> LOCATION: (4)..(5)
<223> OTHER INFORMATION: Xaa can be any naturally occurring amino acid
<220> FEATURE:
<221> NAME/KEY: misc_feature
<222> LOCATION: (7)..(7)
<223> OTHER INFORMATION: Xaa can be any naturally occurring amino acid
<220> FEATURE:
<221> NAME/KEY: misc_feature
<222> LOCATION: (10)..(11)
<223> OTHER INFORMATION: Xaa can be any naturally occurring amino acid
<220> FEATURE:
<221> NAME/KEY: misc_feature
<222> LOCATION: (13)..(15)
<223> OTHER INFORMATION: Xaa can be any naturally occurring amino acid
<220> FEATURE:
<221> NAME/KEY: misc_feature
<222> LOCATION: (17)..(17)
<223> OTHER INFORMATION: Xaa can be any naturally occurring amino acid

<400> SEQUENCE: 6

Xaa Xaa Ala Xaa Xaa Val Xaa Gly Met Xaa Xaa Leu Xaa Xaa Xaa Ala
1               5                   10                  15

Xaa

<210> SEQ ID NO 7
<211> LENGTH: 70
<212> TYPE: PRT
<213> ORGANISM: Homo sapiens

<400> SEQUENCE: 7

Phe Gln Asn Phe Glu Gln Ile Phe Glu Glu Cys Ile Ser Gln Ser Ala
1               5                   10                  15

Val Lys Thr Lys Phe Glu Gln His Thr Ile Arg Ala Lys Gln Ile Leu
            20                  25                  30

Ala Thr Val Lys Asn Ile Met Asp Ser Val Asn Leu Ala Ala Glu Asp
        35                  40                  45

Lys Arg His Tyr Ser Val Glu Arg Glu Asp Gln Ile Asp Arg Leu
    50                  55                  60

Asp Phe Ile Arg Asn Gln
65                  70

<210> SEQ ID NO 8
<211> LENGTH: 84
<212> TYPE: PRT
<213> ORGANISM: Homo sapiens

<400> SEQUENCE: 8

Phe Gln Asn Phe Glu Arg Arg Phe Glu Glu Cys Ile Ser Gln Ser Ala
1               5                   10                  15

Val Lys Thr Lys Phe Glu Gln His Thr Val Arg Ala Lys Gln Ile Ala
            20                  25                  30

Glu Ala Val Arg Leu Ile Met Asp Ser Leu His Met Ala Ala Arg Glu
        35                  40                  45

Gln Gln Val Tyr Cys Glu Glu Met Arg Glu Arg Gln Asp Arg Leu
    50                  55                  60

Lys Phe Ile Asp Lys Gln Leu Glu Leu Leu Ala Gln Asp Tyr Lys Leu
65                  70                  75                  80
```

Arg Ile Lys Gln

```
<210> SEQ ID NO 9
<211> LENGTH: 47
<212> TYPE: PRT
<213> ORGANISM: Homo sapiens

<400> SEQUENCE: 9
```

Phe Gln Asn Phe Glu Gln Ile Phe Glu Cys Ile Ser Gln Ser Ala
1               5                   10                  15

Val Lys Thr Lys Phe Glu Gln His Thr Ile Arg Ala Lys Gln Ile Leu
            20                  25                  30

Ala Thr Val Lys Asn Ile Met Asp Ser Val Asn Leu Ala Ala Glu
        35                  40                  45

```
<210> SEQ ID NO 10
<211> LENGTH: 31
<212> TYPE: PRT
<213> ORGANISM: Homo sapiens

<400> SEQUENCE: 10
```

His Tyr Ser Val Glu Glu Arg Glu Asp Gln Ile Asp Arg Leu Asp Phe
1               5                   10                  15

Ile Arg Asn Gln Met Asn Leu Leu Thr Leu Asp Val Lys Lys Lys
            20                  25                  30

```
<210> SEQ ID NO 11
<211> LENGTH: 47
<212> TYPE: PRT
<213> ORGANISM: Homo sapiens

<400> SEQUENCE: 11
```

Phe Gln Asn Phe Glu Arg Arg Phe Glu Glu Cys Ile Ser Gln Ser Ala
1               5                   10                  15

Val Lys Thr Lys Phe Glu Gln His Thr Val Arg Ala Lys Gln Ile Ala
            20                  25                  30

Glu Ala Val Arg Leu Ile Met Asp Ser Leu His Met Ala Ala Arg
        35                  40                  45

```
<210> SEQ ID NO 12
<211> LENGTH: 32
<212> TYPE: PRT
<213> ORGANISM: Homo sapiens

<400> SEQUENCE: 12
```

Val Tyr Cys Glu Glu Met Arg Glu Arg Gln Asp Arg Leu Lys Phe
1               5                   10                  15

Ile Asp Lys Gln Gln Leu Glu Leu Leu Ala Gln Asp Tyr Lys Leu Arg
            20                  25                  30

```
<210> SEQ ID NO 13
<211> LENGTH: 18
<212> TYPE: PRT
<213> ORGANISM: Homo sapiens

<400> SEQUENCE: 13
```

Gln Ile Ala Glu Ala Val Arg Leu Ile Met Asp Ser Leu His Met Ala
1               5                   10                  15

Ala Arg

-continued

```
<210> SEQ ID NO 14
<211> LENGTH: 18
<212> TYPE: PRT
<213> ORGANISM: Artificial
<220> FEATURE:
<223> OTHER INFORMATION: Synthetic

<400> SEQUENCE: 14

Gln Ile Ala Glu Ala Val Arg Gly Ile Met Asp Ser Leu His Met Ala
1               5                   10                  15

Ala Arg

<210> SEQ ID NO 15
<211> LENGTH: 18
<212> TYPE: PRT
<213> ORGANISM: Artificial
<220> FEATURE:
<223> OTHER INFORMATION: Synthetic

<400> SEQUENCE: 15

Gln Ile Ala Glu Ala Val Arg Pro Ile Met Asp Ser Leu His Met Ala
1               5                   10                  15

Ala Arg

<210> SEQ ID NO 16
<211> LENGTH: 17
<212> TYPE: PRT
<213> ORGANISM: Artificial
<220> FEATURE:
<223> OTHER INFORMATION: Synthetic

<400> SEQUENCE: 16

Gln Ile Ala Glu Ala Val Arg Gly Met Asp Ser Leu His Met Ala Ala
1               5                   10                  15

Arg

<210> SEQ ID NO 17
<211> LENGTH: 21
<212> TYPE: PRT
<213> ORGANISM: Homo sapiens

<400> SEQUENCE: 17

Gln Asp Arg Leu Lys Phe Ile Asp Lys Gln Leu Glu Leu Leu Ala Gln
1               5                   10                  15

Asp Tyr Lys Leu Arg
            20

<210> SEQ ID NO 18
<211> LENGTH: 21
<212> TYPE: PRT
<213> ORGANISM: Artificial
<220> FEATURE:
<223> OTHER INFORMATION: Synthetic

<400> SEQUENCE: 18

Gln Asp Arg Leu Lys Phe Ile Asp Lys Gln Gly Glu Leu Leu Ala Gln
1               5                   10                  15

Asp Tyr Lys Leu Arg
            20

<210> SEQ ID NO 19
<211> LENGTH: 21
<212> TYPE: PRT
<213> ORGANISM: Artificial
```

```
<220> FEATURE:
<223> OTHER INFORMATION: Synthetic

<400> SEQUENCE: 19

Gln Asp Arg Leu Lys Phe Ile Asp Lys Gln Pro Glu Leu Leu Ala Gln
1               5                   10                  15

Asp Tyr Lys Leu Arg
            20

<210> SEQ ID NO 20
<211> LENGTH: 21
<212> TYPE: PRT
<213> ORGANISM: Homo sapiens

<400> SEQUENCE: 20

Arg Gln Val Ser Thr Ala Met Ala Glu Glu Ile Arg Arg Leu Ser Val
1               5                   10                  15

Leu Val Asp Asp Tyr
            20

<210> SEQ ID NO 21
<211> LENGTH: 21
<212> TYPE: PRT
<213> ORGANISM: Artificial
<220> FEATURE:
<223> OTHER INFORMATION: Synthetic

<400> SEQUENCE: 21

Arg Gln Val Ser Thr Ala Met Ala Glu Glu Ile Arg Arg Gly Ser Val
1               5                   10                  15

Leu Val Asp Asp Tyr
            20

<210> SEQ ID NO 22
<211> LENGTH: 21
<212> TYPE: PRT
<213> ORGANISM: Artificial
<220> FEATURE:
<223> OTHER INFORMATION: Synthetic

<400> SEQUENCE: 22

Arg Gln Val Ser Thr Ala Met Ala Glu Glu Ile Arg Arg Pro Ser Val
1               5                   10                  15

Leu Val Asp Asp Tyr
            20

<210> SEQ ID NO 23
<211> LENGTH: 31
<212> TYPE: PRT
<213> ORGANISM: Artificial
<220> FEATURE:
<223> OTHER INFORMATION: Synthetic

<400> SEQUENCE: 23

Gln Ile Ala Glu Ala Val Arg Gly Ile Met Asp Ser Leu His Met Ala
1               5                   10                  15

Ala Arg Gly Gly Tyr Gly Arg Lys Lys Arg Arg Gln Arg Arg Arg
            20                  25                  30

<210> SEQ ID NO 24
<211> LENGTH: 34
<212> TYPE: PRT
<213> ORGANISM: Artificial
<220> FEATURE:
```

<223> OTHER INFORMATION: Synthetic

<400> SEQUENCE: 24

Gln Asp Arg Leu Lys Phe Ile Asp Lys Gln Gly Glu Leu Leu Ala Gln
1               5                   10                  15
Asp Tyr Lys Leu Arg Gly Gly Tyr Gly Arg Lys Lys Arg Arg Gln Arg
            20                  25                  30
Arg Arg

<210> SEQ ID NO 25
<211> LENGTH: 11
<212> TYPE: PRT
<213> ORGANISM: HIV-1

<400> SEQUENCE: 25

Tyr Gly Arg Lys Lys Arg Arg Gln Arg Arg Arg
1               5                   10

<210> SEQ ID NO 26
<211> LENGTH: 11
<212> TYPE: PRT
<213> ORGANISM: Artificial
<220> FEATURE:
<223> OTHER INFORMATION: Synthetic

<400> SEQUENCE: 26

Arg Arg Arg Gln Arg Arg Lys Lys Arg Gly Tyr
1               5                   10

<210> SEQ ID NO 27
<211> LENGTH: 9
<212> TYPE: PRT
<213> ORGANISM: HIV-1

<400> SEQUENCE: 27

Arg Lys Lys Arg Arg Gln Arg Arg Arg
1               5

<210> SEQ ID NO 28
<211> LENGTH: 11
<212> TYPE: PRT
<213> ORGANISM: Artificial
<220> FEATURE:
<223> OTHER INFORMATION: Synthetic

<400> SEQUENCE: 28

Thr His Arg Leu Pro Arg Arg Arg Arg Arg Arg
1               5                   10

<210> SEQ ID NO 29
<211> LENGTH: 11
<212> TYPE: PRT
<213> ORGANISM: Artificial
<220> FEATURE:
<223> OTHER INFORMATION: Synthetic

<400> SEQUENCE: 29

Gly Gly Arg Arg Ala Arg Arg Arg Arg Arg Arg
1               5                   10

<210> SEQ ID NO 30
<211> LENGTH: 12
<212> TYPE: PRT
<213> ORGANISM: Artificial
<220> FEATURE:

<223> OTHER INFORMATION: Synthetic

<400> SEQUENCE: 30

Arg Arg Gln Arg Arg Thr Ser Lys Leu Met Lys Arg
1               5                   10

<210> SEQ ID NO 31
<211> LENGTH: 27
<212> TYPE: PRT
<213> ORGANISM: Artificial
<220> FEATURE:
<223> OTHER INFORMATION: Synthetic

<400> SEQUENCE: 31

Gly Trp Thr Leu Asn Ser Ala Gly Tyr Leu Leu Gly Lys Ile Asn Leu
1               5                   10                  15

Lys Ala Leu Ala Ala Leu Ala Lys Lys Ile Leu
            20                  25

<210> SEQ ID NO 32
<211> LENGTH: 29
<212> TYPE: PRT
<213> ORGANISM: Artificial
<220> FEATURE:
<223> OTHER INFORMATION: Synthetic

<400> SEQUENCE: 32

Trp Glu Ala Lys Leu Ala Lys Ala Leu Ala Lys Ala Leu Ala Lys His
1               5                   10                  15

Leu Ala Lys Ala Leu Ala Lys Ala Leu Lys Cys Glu Ala
            20                  25

<210> SEQ ID NO 33
<211> LENGTH: 16
<212> TYPE: PRT
<213> ORGANISM: Drosophilia sp.

<400> SEQUENCE: 33

Arg Gln Ile Lys Ile Trp Phe Gln Asn Arg Arg Met Lys Trp Lys Lys
1               5                   10                  15

<210> SEQ ID NO 34
<211> LENGTH: 4
<212> TYPE: PRT
<213> ORGANISM: Artificial
<220> FEATURE:
<223> OTHER INFORMATION: Synthetic

<400> SEQUENCE: 34

Gly Gly Gly Gly
1

<210> SEQ ID NO 35
<211> LENGTH: 5
<212> TYPE: PRT
<213> ORGANISM: Artificial
<220> FEATURE:
<223> OTHER INFORMATION: Synthetic

<400> SEQUENCE: 35

Gly Ser Gly Gly Ser
1               5

<210> SEQ ID NO 36
<211> LENGTH: 4

```
<212> TYPE: PRT
<213> ORGANISM: Artificial
<220> FEATURE:
<223> OTHER INFORMATION: Synthetic

<400> SEQUENCE: 36

Gly Gly Gly Ser
1

<210> SEQ ID NO 37
<211> LENGTH: 5
<212> TYPE: PRT
<213> ORGANISM: Artificial
<220> FEATURE:
<223> OTHER INFORMATION: Synthetic

<400> SEQUENCE: 37

Gly Gly Ser Gly Gly
1               5

<210> SEQ ID NO 38
<211> LENGTH: 5
<212> TYPE: PRT
<213> ORGANISM: Artificial
<220> FEATURE:
<223> OTHER INFORMATION: Synthetic

<400> SEQUENCE: 38

Gly Ser Gly Ser Gly
1               5

<210> SEQ ID NO 39
<211> LENGTH: 5
<212> TYPE: PRT
<213> ORGANISM: Artificial
<220> FEATURE:
<223> OTHER INFORMATION: Synthetic

<400> SEQUENCE: 39

Gly Ser Gly Gly Gly
1               5

<210> SEQ ID NO 40
<211> LENGTH: 5
<212> TYPE: PRT
<213> ORGANISM: Artificial
<220> FEATURE:
<223> OTHER INFORMATION: Synthetic

<400> SEQUENCE: 40

Gly Gly Gly Ser Gly
1               5

<210> SEQ ID NO 41
<211> LENGTH: 5
<212> TYPE: PRT
<213> ORGANISM: Artificial
<220> FEATURE:
<223> OTHER INFORMATION: Synthetic

<400> SEQUENCE: 41

Gly Ser Ser Ser Gly
1               5

<210> SEQ ID NO 42
<211> LENGTH: 4
<212> TYPE: PRT
```

```
<213> ORGANISM: Artificial
<220> FEATURE:
<223> OTHER INFORMATION: Synthetic

<400> SEQUENCE: 42

Gly Gly Ser Gly
1

<210> SEQ ID NO 43
<211> LENGTH: 11
<212> TYPE: PRT
<213> ORGANISM: Artificial
<220> FEATURE:
<223> OTHER INFORMATION: Synthetic

<400> SEQUENCE: 43

Gly Glu Leu Leu Ala Gln Asp Tyr Lys Leu Arg
1               5                   10

<210> SEQ ID NO 44
<211> LENGTH: 11
<212> TYPE: PRT
<213> ORGANISM: Artificial
<220> FEATURE:
<223> OTHER INFORMATION: Synthetic

<400> SEQUENCE: 44

Gln Asp Arg Leu Lys Phe Ile Asp Lys Gln Gly
1               5                   10

<210> SEQ ID NO 45
<211> LENGTH: 24
<212> TYPE: PRT
<213> ORGANISM: Artificial
<220> FEATURE:
<223> OTHER INFORMATION: Synthetic

<400> SEQUENCE: 45

Gly Glu Leu Leu Ala Gln Asp Tyr Lys Leu Arg Gly Gly Tyr Gly Arg
1               5                   10                  15

Lys Lys Arg Arg Gln Arg Arg Arg
            20

<210> SEQ ID NO 46
<211> LENGTH: 23
<212> TYPE: PRT
<213> ORGANISM: Artificial
<220> FEATURE:
<223> OTHER INFORMATION: Synthetic

<400> SEQUENCE: 46

Gln Asp Arg Leu Lys Phe Ile Asp Lys Gln Gly Gly Tyr Gly Arg Lys
1               5                   10                  15

Lys Arg Arg Gln Arg Arg Arg
            20

<210> SEQ ID NO 47
<211> LENGTH: 8
<212> TYPE: PRT
<213> ORGANISM: Artificial
<220> FEATURE:
<223> OTHER INFORMATION: Synthetic

<400> SEQUENCE: 47

Gln Ile Ala Glu Ala Val Arg Gly
1               5
```

```
<210> SEQ ID NO 48
<211> LENGTH: 11
<212> TYPE: PRT
<213> ORGANISM: Artificial
<220> FEATURE:
<223> OTHER INFORMATION: Synthetic

<400> SEQUENCE: 48

Gly Ile Met Asp Ser Leu His Met Ala Ala Arg
1               5                   10

<210> SEQ ID NO 49
<211> LENGTH: 21
<212> TYPE: PRT
<213> ORGANISM: Artificial
<220> FEATURE:
<223> OTHER INFORMATION: Synthetic

<400> SEQUENCE: 49

Gln Ile Ala Glu Ala Val Arg Gly Gly Tyr Gly Arg Lys Lys Arg Arg
1               5                   10                  15

Gln Arg Arg Arg Arg
            20

<210> SEQ ID NO 50
<211> LENGTH: 24
<212> TYPE: PRT
<213> ORGANISM: Artificial
<220> FEATURE:
<223> OTHER INFORMATION: Synthetic

<400> SEQUENCE: 50

Gly Ile Met Asp Ser Leu His Met Ala Ala Arg Gly Gly Tyr Gly Arg
1               5                   10                  15

Lys Lys Arg Arg Gln Arg Arg Arg
            20

<210> SEQ ID NO 51
<211> LENGTH: 11
<212> TYPE: PRT
<213> ORGANISM: Artificial
<220> FEATURE:
<223> OTHER INFORMATION: Synthetic
<220> FEATURE:
<221> NAME/KEY: misc_feature
<222> LOCATION: (4)..(5)
<223> OTHER INFORMATION: Xaa can be any naturally occurring amino acid
<220> FEATURE:
<221> NAME/KEY: misc_feature
<222> LOCATION: (7)..(9)
<223> OTHER INFORMATION: Xaa can be any naturally occurring amino acid
<220> FEATURE:
<221> NAME/KEY: misc_feature
<222> LOCATION: (11)..(11)
<223> OTHER INFORMATION: Xaa can be any naturally occurring amino acid

<400> SEQUENCE: 51

Gly Ile Met Xaa Xaa Leu Xaa Xaa Xaa Ala Xaa
1               5                   10

<210> SEQ ID NO 52
<211> LENGTH: 10
<212> TYPE: PRT
<213> ORGANISM: Artificial
<220> FEATURE:
<223> OTHER INFORMATION: Synthetic
<220> FEATURE:
```

```
<221> NAME/KEY: misc_feature
<222> LOCATION: (3)..(4)
<223> OTHER INFORMATION: Xaa can be any naturally occurring amino acid
<220> FEATURE:
<221> NAME/KEY: misc_feature
<222> LOCATION: (6)..(8)
<223> OTHER INFORMATION: Xaa can be any naturally occurring amino acid
<220> FEATURE:
<221> NAME/KEY: misc_feature
<222> LOCATION: (10)..(10)
<223> OTHER INFORMATION: Xaa can be any naturally occurring amino acid

<400> SEQUENCE: 52

Gly Met Xaa Xaa Leu Xaa Xaa Xaa Ala Xaa
1               5                   10

<210> SEQ ID NO 53
<211> LENGTH: 24
<212> TYPE: PRT
<213> ORGANISM: Artificial
<220> FEATURE:
<223> OTHER INFORMATION: Synthetic

<400> SEQUENCE: 53

Gly Ile Met Asp Asp Leu His Met Ala Ala Arg Gly Gly Tyr Gly Arg
1               5                   10                  15

Lys Lys Arg Arg Gln Arg Arg Arg
            20

<210> SEQ ID NO 54
<211> LENGTH: 24
<212> TYPE: PRT
<213> ORGANISM: Artificial
<220> FEATURE:
<223> OTHER INFORMATION: Synthetic
<220> FEATURE:
<221> NAME/KEY: MOD_RES
<222> LOCATION: (5)..(5)
<223> OTHER INFORMATION: PHOSPHORYLATION

<400> SEQUENCE: 54

Gly Ile Met Asp Ser Leu His Met Ala Ala Arg Gly Gly Tyr Gly Arg
1               5                   10                  15

Lys Lys Arg Arg Gln Arg Arg Arg
            20

<210> SEQ ID NO 55
<211> LENGTH: 24
<212> TYPE: PRT
<213> ORGANISM: Artificial
<220> FEATURE:
<223> OTHER INFORMATION: Synthetic

<400> SEQUENCE: 55

Gly Ile Met Ala Ser Leu His Met Ala Ala Arg Gly Gly Tyr Gly Arg
1               5                   10                  15

Lys Lys Arg Arg Gln Arg Arg Arg
            20

<210> SEQ ID NO 56
<211> LENGTH: 24
<212> TYPE: PRT
<213> ORGANISM: Artificial
<220> FEATURE:
<223> OTHER INFORMATION: Synthetic

<400> SEQUENCE: 56
```

-continued

Gly Ile Met Asp Ser Ala His Met Ala Ala Arg Gly Gly Tyr Gly Arg
1               5                   10                  15

Lys Lys Arg Arg Gln Arg Arg Arg
            20

<210> SEQ ID NO 57
<211> LENGTH: 24
<212> TYPE: PRT
<213> ORGANISM: Artificial
<220> FEATURE:
<223> OTHER INFORMATION: Synthetic

<400> SEQUENCE: 57

Gly Ile Met Asp Ser Leu Ala Met Ala Ala Arg Gly Gly Tyr Gly Arg
1               5                   10                  15

Lys Lys Arg Arg Gln Arg Arg Arg
            20

<210> SEQ ID NO 58
<211> LENGTH: 24
<212> TYPE: PRT
<213> ORGANISM: Artificial
<220> FEATURE:
<223> OTHER INFORMATION: Synthetic

<400> SEQUENCE: 58

Gly Ile Ala Asp Ser Leu His Met Ala Ala Arg Gly Gly Tyr Gly Arg
1               5                   10                  15

Lys Lys Arg Arg Gln Arg Arg Arg
            20

<210> SEQ ID NO 59
<211> LENGTH: 24
<212> TYPE: PRT
<213> ORGANISM: Artificial
<220> FEATURE:
<223> OTHER INFORMATION: Synthetic

<400> SEQUENCE: 59

Gly Ile Met Asp Ala Leu His Met Ala Ala Arg Gly Gly Tyr Gly Arg
1               5                   10                  15

Lys Lys Arg Arg Gln Arg Arg Arg
            20

<210> SEQ ID NO 60
<211> LENGTH: 24
<212> TYPE: PRT
<213> ORGANISM: Artificial
<220> FEATURE:
<223> OTHER INFORMATION: Synthetic

<400> SEQUENCE: 60

Gly Ile Met Asp Cys Leu His Met Ala Ala Arg Gly Gly Tyr Gly Arg
1               5                   10                  15

Lys Lys Arg Arg Gln Arg Arg Arg
            20

<210> SEQ ID NO 61
<211> LENGTH: 24
<212> TYPE: PRT
<213> ORGANISM: Artificial
<220> FEATURE:
<223> OTHER INFORMATION: Synthetic

<400> SEQUENCE: 61

```
Gly Ile Met Asp Asn Leu His Met Ala Ala Arg Gly Gly Tyr Gly Arg
1               5                   10                  15

Lys Lys Arg Arg Gln Arg Arg Arg
            20
```

<210> SEQ ID NO 62
<211> LENGTH: 24
<212> TYPE: PRT
<213> ORGANISM: Artificial
<220> FEATURE:
<223> OTHER INFORMATION: Synthetic

<400> SEQUENCE: 62

```
Gly Ile Met Asp Gly Leu His Met Ala Ala Arg Gly Gly Tyr Gly Arg
1               5                   10                  15

Lys Lys Arg Arg Gln Arg Arg Arg
            20
```

<210> SEQ ID NO 63
<211> LENGTH: 24
<212> TYPE: PRT
<213> ORGANISM: Artificial
<220> FEATURE:
<223> OTHER INFORMATION: Synthetic

<400> SEQUENCE: 63

```
Gly Ile Met Asp Ser Leu His Ala Ala Ala Arg Gly Gly Tyr Gly Arg
1               5                   10                  15

Lys Lys Arg Arg Gln Arg Arg Arg
            20
```

<210> SEQ ID NO 64
<211> LENGTH: 24
<212> TYPE: PRT
<213> ORGANISM: Artificial
<220> FEATURE:
<223> OTHER INFORMATION: Synthetic

<400> SEQUENCE: 64

```
Gly Glu Leu Leu Ala Gln Ala Tyr Lys Leu Arg Gly Gly Tyr Gly Arg
1               5                   10                  15

Lys Lys Arg Arg Gln Arg Arg Arg
            20
```

<210> SEQ ID NO 65
<211> LENGTH: 24
<212> TYPE: PRT
<213> ORGANISM: Artificial
<220> FEATURE:
<223> OTHER INFORMATION: Synthetic

<400> SEQUENCE: 65

```
Gly Glu Leu Leu Ala Gln Asp Tyr Lys Ala Arg Gly Gly Tyr Gly Arg
1               5                   10                  15

Lys Lys Arg Arg Gln Arg Arg Arg
            20
```

<210> SEQ ID NO 66
<211> LENGTH: 24
<212> TYPE: PRT
<213> ORGANISM: Artificial
<220> FEATURE:
<223> OTHER INFORMATION: Synthetic -continued

```
<400> SEQUENCE: 66

Gly Ala Leu Leu Ala Gln Asp Tyr Lys Leu Arg Gly Gly Tyr Gly Arg
1               5                   10                  15

Lys Lys Arg Arg Gln Arg Arg Arg
            20

<210> SEQ ID NO 67
<211> LENGTH: 24
<212> TYPE: PRT
<213> ORGANISM: Artificial
<220> FEATURE:
<223> OTHER INFORMATION: Synthetic

<400> SEQUENCE: 67

Gly Glu Ala Leu Ala Gln Asp Tyr Lys Leu Arg Gly Gly Tyr Gly Arg
1               5                   10                  15

Lys Lys Arg Arg Gln Arg Arg Arg
            20

<210> SEQ ID NO 68
<211> LENGTH: 24
<212> TYPE: PRT
<213> ORGANISM: Artificial
<220> FEATURE:
<223> OTHER INFORMATION: Synthetic

<400> SEQUENCE: 68

Gly Glu Leu Ala Ala Gln Asp Tyr Lys Leu Arg Gly Gly Tyr Gly Arg
1               5                   10                  15

Lys Lys Arg Arg Gln Arg Arg Arg
            20

<210> SEQ ID NO 69
<211> LENGTH: 24
<212> TYPE: PRT
<213> ORGANISM: Artificial
<220> FEATURE:
<223> OTHER INFORMATION: Synthetic

<400> SEQUENCE: 69

Gly Glu Leu Leu Ala Ala Asp Tyr Lys Leu Arg Gly Gly Tyr Gly Arg
1               5                   10                  15

Lys Lys Arg Arg Gln Arg Arg Arg
            20

<210> SEQ ID NO 70
<211> LENGTH: 24
<212> TYPE: PRT
<213> ORGANISM: Artificial
<220> FEATURE:
<223> OTHER INFORMATION: Synthetic

<400> SEQUENCE: 70

Gly Glu Leu Leu Ala Gln Asp Ala Lys Leu Arg Gly Gly Tyr Gly Arg
1               5                   10                  15

Lys Lys Arg Arg Gln Arg Arg Arg
            20

<210> SEQ ID NO 71
<211> LENGTH: 24
<212> TYPE: PRT
<213> ORGANISM: Artificial
<220> FEATURE:
<223> OTHER INFORMATION: Synthetic
```

```
<400> SEQUENCE: 71

Gly Glu Leu Leu Ala Gln Asp Tyr Ala Leu Arg Gly Gly Tyr Gly Arg
1               5                   10                  15

Lys Lys Arg Arg Gln Arg Arg Arg
            20

<210> SEQ ID NO 72
<211> LENGTH: 24
<212> TYPE: PRT
<213> ORGANISM: Artificial
<220> FEATURE:
<223> OTHER INFORMATION: Synthetic

<400> SEQUENCE: 72

Gly Glu Leu Leu Ala Gln Asp Tyr Lys Leu Ala Gly Gly Tyr Gly Arg
1               5                   10                  15

Lys Lys Arg Arg Gln Arg Arg Arg
            20

<210> SEQ ID NO 73
<211> LENGTH: 11
<212> TYPE: PRT
<213> ORGANISM: Artificial
<220> FEATURE:
<223> OTHER INFORMATION: Synthetic
<220> FEATURE:
<221> NAME/KEY: misc_feature
<222> LOCATION: (4)..(7)
<223> OTHER INFORMATION: Xaa can be any naturally occurring amino acid

<400> SEQUENCE: 73

Gly Ile Met Xaa Xaa Xaa Xaa Met Ala Ala Arg
1               5                   10

<210> SEQ ID NO 74
<211> LENGTH: 11
<212> TYPE: PRT
<213> ORGANISM: Artificial
<220> FEATURE:
<223> OTHER INFORMATION: Synthetic
<220> FEATURE:
<221> NAME/KEY: misc_feature
<222> LOCATION: (7)..(7)
<223> OTHER INFORMATION: Xaa can be any naturally occurring amino acid
<220> FEATURE:
<221> NAME/KEY: misc_feature
<222> LOCATION: (10)..(10)
<223> OTHER INFORMATION: Xaa can be any naturally occurring amino acid

<400> SEQUENCE: 74

Gly Glu Leu Leu Ala Gln Xaa Tyr Lys Xaa Arg
1               5                   10

<210> SEQ ID NO 75
<211> LENGTH: 11
<212> TYPE: PRT
<213> ORGANISM: Artificial
<220> FEATURE:
<223> OTHER INFORMATION: Synthetic

<400> SEQUENCE: 75

Gly Ile Met Asp Asp Leu His Met Ala Ala Arg
1               5                   10

<210> SEQ ID NO 76
<211> LENGTH: 11
```

```
<212> TYPE: PRT
<213> ORGANISM: Artificial
<220> FEATURE:
<223> OTHER INFORMATION: Synthetic
<220> FEATURE:
<221> NAME/KEY: MOD_RES
<222> LOCATION: (5)..(5)
<223> OTHER INFORMATION: PHOSPHORYLATION

<400> SEQUENCE: 76

Gly Ile Met Asp Ser Leu His Met Ala Ala Arg
1               5                   10

<210> SEQ ID NO 77
<211> LENGTH: 11
<212> TYPE: PRT
<213> ORGANISM: Artificial
<220> FEATURE:
<223> OTHER INFORMATION: Synthetic

<400> SEQUENCE: 77

Gly Ile Met Ala Ser Leu His Met Ala Ala Arg
1               5                   10

<210> SEQ ID NO 78
<211> LENGTH: 11
<212> TYPE: PRT
<213> ORGANISM: Artificial
<220> FEATURE:
<223> OTHER INFORMATION: Synthetic

<400> SEQUENCE: 78

Gly Ile Met Asp Ser Ala His Met Ala Ala Arg
1               5                   10

<210> SEQ ID NO 79
<211> LENGTH: 11
<212> TYPE: PRT
<213> ORGANISM: Artificial
<220> FEATURE:
<223> OTHER INFORMATION: Synthetic

<400> SEQUENCE: 79

Gly Ile Met Asp Ser Leu Ala Met Ala Ala Arg
1               5                   10

<210> SEQ ID NO 80
<211> LENGTH: 11
<212> TYPE: PRT
<213> ORGANISM: Artificial
<220> FEATURE:
<223> OTHER INFORMATION: Synthetic

<400> SEQUENCE: 80

Gly Ile Ala Asp Ser Leu His Met Ala Ala Arg
1               5                   10

<210> SEQ ID NO 81
<211> LENGTH: 11
<212> TYPE: PRT
<213> ORGANISM: Artificial
<220> FEATURE:
<223> OTHER INFORMATION: Synthetic

<400> SEQUENCE: 81

Gly Ile Met Asp Ala Leu His Met Ala Ala Arg
1               5                   10
```

<210> SEQ ID NO 82
<211> LENGTH: 11
<212> TYPE: PRT
<213> ORGANISM: Artificial
<220> FEATURE:
<223> OTHER INFORMATION: Synthetic

<400> SEQUENCE: 82

Gly Ile Met Asp Cys Leu His Met Ala Ala Arg
1               5                   10

<210> SEQ ID NO 83
<211> LENGTH: 11
<212> TYPE: PRT
<213> ORGANISM: Artificial
<220> FEATURE:
<223> OTHER INFORMATION: Synthetic

<400> SEQUENCE: 83

Gly Ile Met Asp Asn Leu His Met Ala Ala Arg
1               5                   10

<210> SEQ ID NO 84
<211> LENGTH: 11
<212> TYPE: PRT
<213> ORGANISM: Artificial
<220> FEATURE:
<223> OTHER INFORMATION: Synthetic

<400> SEQUENCE: 84

Gly Ile Met Asp Gly Leu His Met Ala Ala Arg
1               5                   10

<210> SEQ ID NO 85
<211> LENGTH: 11
<212> TYPE: PRT
<213> ORGANISM: Artificial
<220> FEATURE:
<223> OTHER INFORMATION: Synthetic

<400> SEQUENCE: 85

Gly Ile Met Asp Ser Leu His Ala Ala Ala Arg
1               5                   10

<210> SEQ ID NO 86
<211> LENGTH: 11
<212> TYPE: PRT
<213> ORGANISM: Artificial
<220> FEATURE:
<223> OTHER INFORMATION: Synthetic

<400> SEQUENCE: 86

Gly Glu Leu Leu Ala Gln Ala Tyr Lys Leu Arg
1               5                   10

<210> SEQ ID NO 87
<211> LENGTH: 11
<212> TYPE: PRT
<213> ORGANISM: Artificial
<220> FEATURE:
<223> OTHER INFORMATION: Synthetic

<400> SEQUENCE: 87

Gly Glu Leu Leu Ala Gln Asp Tyr Lys Ala Arg
1               5                   10

```
<210> SEQ ID NO 88
<211> LENGTH: 11
<212> TYPE: PRT
<213> ORGANISM: Artificial
<220> FEATURE:
<223> OTHER INFORMATION: Synthetic

<400> SEQUENCE: 88

Gly Ala Leu Leu Ala Gln Asp Tyr Lys Leu Arg
1               5                   10

<210> SEQ ID NO 89
<211> LENGTH: 11
<212> TYPE: PRT
<213> ORGANISM: Artificial
<220> FEATURE:
<223> OTHER INFORMATION: Synthetic

<400> SEQUENCE: 89

Gly Glu Ala Leu Ala Gln Asp Tyr Lys Leu Arg
1               5                   10

<210> SEQ ID NO 90
<211> LENGTH: 11
<212> TYPE: PRT
<213> ORGANISM: Artificial
<220> FEATURE:
<223> OTHER INFORMATION: Synthetic

<400> SEQUENCE: 90

Gly Glu Leu Ala Ala Gln Asp Tyr Lys Leu Arg
1               5                   10

<210> SEQ ID NO 91
<211> LENGTH: 11
<212> TYPE: PRT
<213> ORGANISM: Artificial
<220> FEATURE:
<223> OTHER INFORMATION: Synthetic

<400> SEQUENCE: 91

Gly Glu Leu Leu Ala Ala Asp Tyr Lys Leu Arg
1               5                   10

<210> SEQ ID NO 92
<211> LENGTH: 11
<212> TYPE: PRT
<213> ORGANISM: Artificial
<220> FEATURE:
<223> OTHER INFORMATION: Synthetic

<400> SEQUENCE: 92

Gly Glu Leu Leu Ala Gln Asp Ala Lys Leu Arg
1               5                   10

<210> SEQ ID NO 93
<211> LENGTH: 11
<212> TYPE: PRT
<213> ORGANISM: Artificial
<220> FEATURE:
<223> OTHER INFORMATION: Synthetic

<400> SEQUENCE: 93

Gly Glu Leu Leu Ala Gln Asp Tyr Ala Leu Arg
1               5                   10

<210> SEQ ID NO 94
```

```
<211> LENGTH: 11
<212> TYPE: PRT
<213> ORGANISM: Artificial
<220> FEATURE:
<223> OTHER INFORMATION: Synthetic

<400> SEQUENCE: 94

Gly Glu Leu Leu Ala Gln Asp Tyr Lys Leu Ala
1               5                   10
```